(12) United States Patent
Dalal et al.

(10) Patent No.: US 11,664,108 B2
(45) Date of Patent: May 30, 2023

(54) SYSTEMS, METHODS, AND DEVICES FOR BIOPHYSICAL MODELING AND RESPONSE PREDICTION

(71) Applicant: January, Inc., Menlo Park, CA (US)

(72) Inventors: Parin Bhadrik Dalal, Palo Alto, CA (US); Salar Rahili, Menlo Park, CA (US); Solmaz Shariat Torbaghan, Burlingame, CA (US); Mehrdad Yazdani, Santa Clara, CA (US)

(73) Assignee: January, Inc., Menlo Park, CA (US)

( * ) Notice: Subject to any disclaimer, the term of this patent is extended or adjusted under 35 U.S.C. 154(b) by 244 days.

(21) Appl. No.: 16/714,209

(22) Filed: Dec. 13, 2019

(65) Prior Publication Data

US 2020/0176121 A1    Jun. 4, 2020

Related U.S. Application Data

(63) Continuation of application No. PCT/US2019/063788, filed on Nov. 27, 2019.

(60) Provisional application No. 62/773,117, filed on Nov. 29, 2018, provisional application No. 62/773,134, (Continued)

(51) Int. Cl.
| | | |
|---|---|---|
| *G16H 50/50* | (2018.01) | |
| *G16H 20/60* | (2018.01) | |
| *G06N 3/08* | (2023.01) | |
| *G16H 20/30* | (2018.01) | |
| *G06F 18/214* | (2023.01) | |
| *G06F 18/21* | (2023.01) | |

(Continued)

(52) U.S. Cl.
CPC ........... *G16H 20/60* (2018.01); *G06F 18/214* (2023.01); *G06F 18/217* (2023.01); *G06N 3/08* (2013.01); *G06V 10/776* (2022.01); *G06V 10/82* (2022.01); *G16H 20/30* (2018.01); *G16H 50/50* (2018.01)

(58) Field of Classification Search
CPC ...................................................... G16H 50/50
See application file for complete search history.

(56) References Cited

U.S. PATENT DOCUMENTS

| | | |
|---|---|---|
| 8,870,766 B2 | 10/2014 | Stivoric et al. |
| 2004/0030584 A1 | 2/2004 | Harris |
| 2004/0138920 A1 | 7/2004 | Sawanaga et al. |

(Continued)

FOREIGN PATENT DOCUMENTS

| | | |
|---|---|---|
| CN | 206729369 U | 12/2017 |
| EP | 3888103 A1 | 10/2021 |

(Continued)

OTHER PUBLICATIONS

PCT/US2019/063788 International Search Report dated Apr. 24, 2020.

(Continued)

*Primary Examiner* — Reginald R Reyes
(74) *Attorney, Agent, or Firm* — Wilson Sonsini Goodrich & Rosati

(57) ABSTRACT

Various systems and methods are disclosed. One or more of the methods disclosed uses machine learning algorithms to predict biophysical responses from biophysical data, such as heart rate monitor data, food logs, or glucose measurements. Biophysical responses may include behavioral responses. Additional systems and methods extract nutritional information from food items by parsing strings containing names of food items.

23 Claims, 45 Drawing Sheets

Related U.S. Application Data filed on Nov. 29, 2018, provisional application No. 62/773,125, filed on Nov. 29, 2018.

(51) Int. Cl.
*G06V 10/776* (2022.01)
*G06V 10/82* (2022.01)

(56) References Cited

U.S. PATENT DOCUMENTS

| | | | |
|---|---|---|---|
| 2005/0091084 A1 | 4/2005 | McGuigan et al. | |
| 2008/0051679 A1 | 2/2008 | Maljanian | |
| 2010/0179930 A1 | 7/2010 | Teller et al. | |
| 2010/0280531 A1* | 11/2010 | Kalpin | A61M 5/14276 606/148 |
| 2011/0047108 A1 | 2/2011 | Chakrabarty et al. | |
| 2012/0158633 A1 | 6/2012 | Eder | |
| 2012/0203573 A1* | 8/2012 | Mayer | G16H 40/63 705/3 |
| 2014/0117080 A1 | 5/2014 | Schwarz et al. | |
| 2014/0310025 A1* | 10/2014 | Sayada | G16B 50/00 705/2 |
| 2015/0120317 A1* | 4/2015 | Mayou | G16H 40/63 705/2 |
| 2015/0213232 A1* | 7/2015 | Walker, II | G16H 50/30 702/19 |
| 2016/0029931 A1 | 2/2016 | Salas-Boni et al. | |
| 2016/0374625 A1 | 12/2016 | Mulligan et al. | |
| 2017/0049383 A1 | 2/2017 | McMahon et al. | |
| 2017/0053552 A1* | 2/2017 | Zhong | A61B 5/7405 |
| 2017/0100635 A1 | 4/2017 | Takeuchi et al. | |
| 2017/0206464 A1 | 7/2017 | Clayton et al. | |
| 2018/0032871 A1 | 2/2018 | Holt et al. | |
| 2018/0096253 A1 | 4/2018 | Goldstein et al. | |
| 2018/0256103 A1 | 9/2018 | Cole et al. | |
| 2018/0272063 A1 | 9/2018 | Neemuchwala et al. | |
| 2018/0277246 A1 | 9/2018 | Zhong et al. | |
| 2018/0330824 A1 | 11/2018 | Athey et al. | |
| 2019/0163270 A1* | 5/2019 | Da Silva | A61B 5/744 |
| 2019/0252079 A1* | 8/2019 | Constantin | A61B 5/0024 |
| 2019/0267121 A1 | 8/2019 | De Sousa Moura et al. | |
| 2020/0245913 A1 | 8/2020 | Dalal et al. | |
| 2020/0349448 A1 | 11/2020 | Dalal et al. | |
| 2021/0158378 A1* | 5/2021 | Jones | G16H 20/30 |
| 2022/0039758 A1* | 2/2022 | Jennings | A61B 5/7275 |

FOREIGN PATENT DOCUMENTS

| | | |
|---|---|---|
| WO | WO-2017094267 A1 | 6/2017 |
| WO | WO-2017175608 A1 | 10/2017 |
| WO | WO-2020113128 A1 | 6/2020 |

OTHER PUBLICATIONS

EP19888687.1 Extended European Search Report dated Oct. 24, 2022.

Luo Yan: "Machine Learning of Lifestyle Data for Diabetes",Electronic Thesis and Dissertation Repository, Jan. 1, 2016 (Jan. 1, 2016), pp. 1-109, XP055664687, Retrieved from the Internet:URL:https://ir.lib.uwo.ca/etd/3650 [retrieved on Feb. 4, 2020].

Rigla, M. et al., Artificial Intelligence Methodologies and Their Application toDiabetes, Journal of Diabetes science and technology, 2018, vol. 12(2) 303-310; available at:www.ncbi.nlm.nih.gov/pmc/articles/PMC5851211/ [Accessed Jul. 1, 2022].

U.S. Appl. No. 16/785,436 Office Action dated Aug. 2, 2022.

U.S. Appl. No. 16/911,208 Office Action dated Jul. 21, 2022.

Vieira, G., "New App May Predict Diabetes Long Before Blood Sugar Levels Do", Health News, Aug. 20, 2018;4 Pages: available at: https://www.healthline.com/health-news/app-predictdiabetes-before-blood-sugar-levels, [Accessed Jul. 1, 2022].

U.S. Appl. No. 16/785,436 Office Action dated Mar. 28, 2023.

\* cited by examiner

```
1  def run_service(self, user_id, msg)
       # identify target
       if self.target is None:
           self.producer.send(user_id, msg)

# User based transformation target
       else:

# Create DB structure
2          in_mem_dir = self.in_memory_db_location
           random_dir = ''.join(random.choices(string.ascii_uppercase + string.digits, k=1))
           name_container_db = in_mem_dir + random_dir + 'cotainer.db'

# Write container to in-memory database
3          self._write_sqlite_blob(name_container_db=name container_db, user_id=user_id)

# Decorate target process to produce message output when complete
4          new_target = post_process_decorator(send_func=self.producer.send, user_id=user_id,
                                  target_func=self.target, ingress_msg=msg,
                                  db_name=name_container_db)

# Fork of separate asynchronous process
5          p = Process(target=new_target, args=())
           self.containers.append(Container (process=p, container_dir=name_container_db))
6          p.start()
           logging.info('Executed contain process pid: {}'.format(p.pid))
```

```
# Encapsulate Egress Message according to ML Service Protocol
def service_encode(query, results, db_name=""):

:type db_name: str
    :type query: dict
    :type results: dict
    :return:

query_json = query
    results['version'] = 1
    results['db_name'] = db_name
    query_json['results'] = results return query_json
```

```
# Decorator helper for container transformation
def post_process_decorator(send_func, user_id, target_func, ingress_msg, db_name):
    def new_target():
        send_func(user_id=user_id,
                  msg_json=service_encode(query=ingress_msg,
                              results=target_func(db_name, ingress_msg),
                              db_name=db_name))

return new_target
```

FIG. 12B

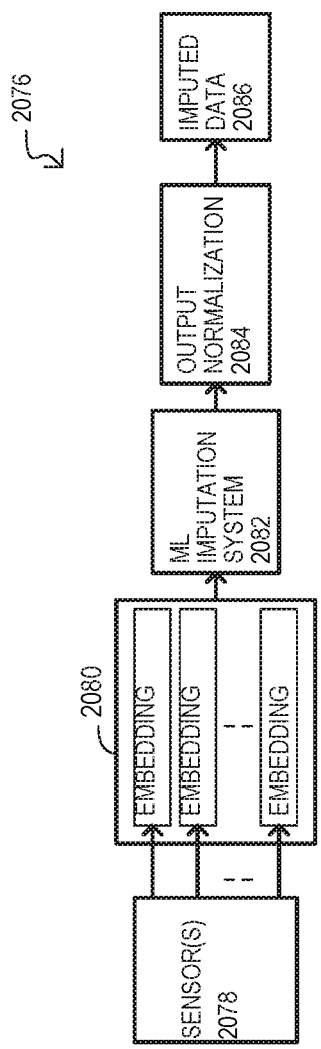

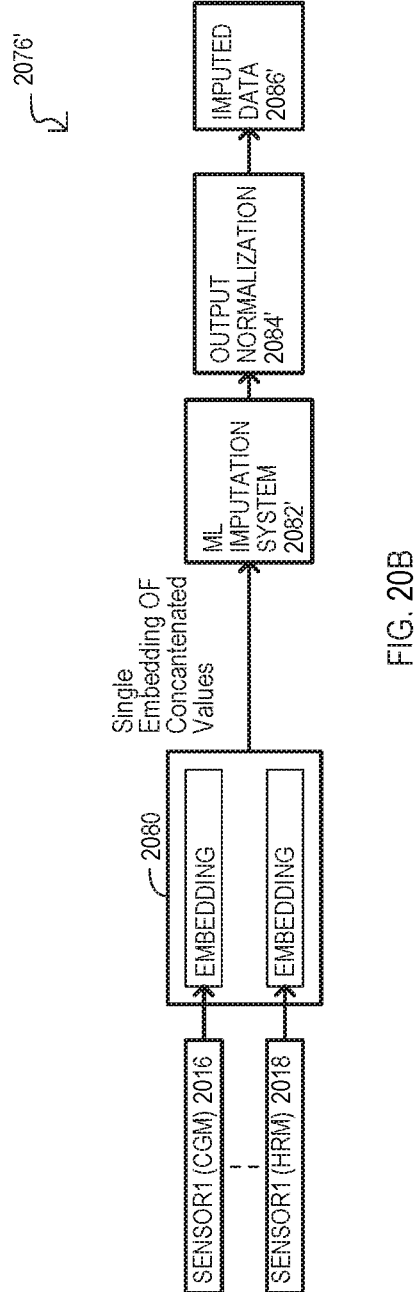
FIG. 20B
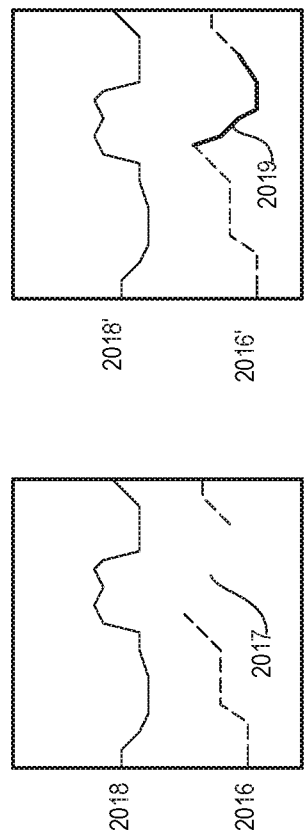
FIG. 20C
FIG. 20D

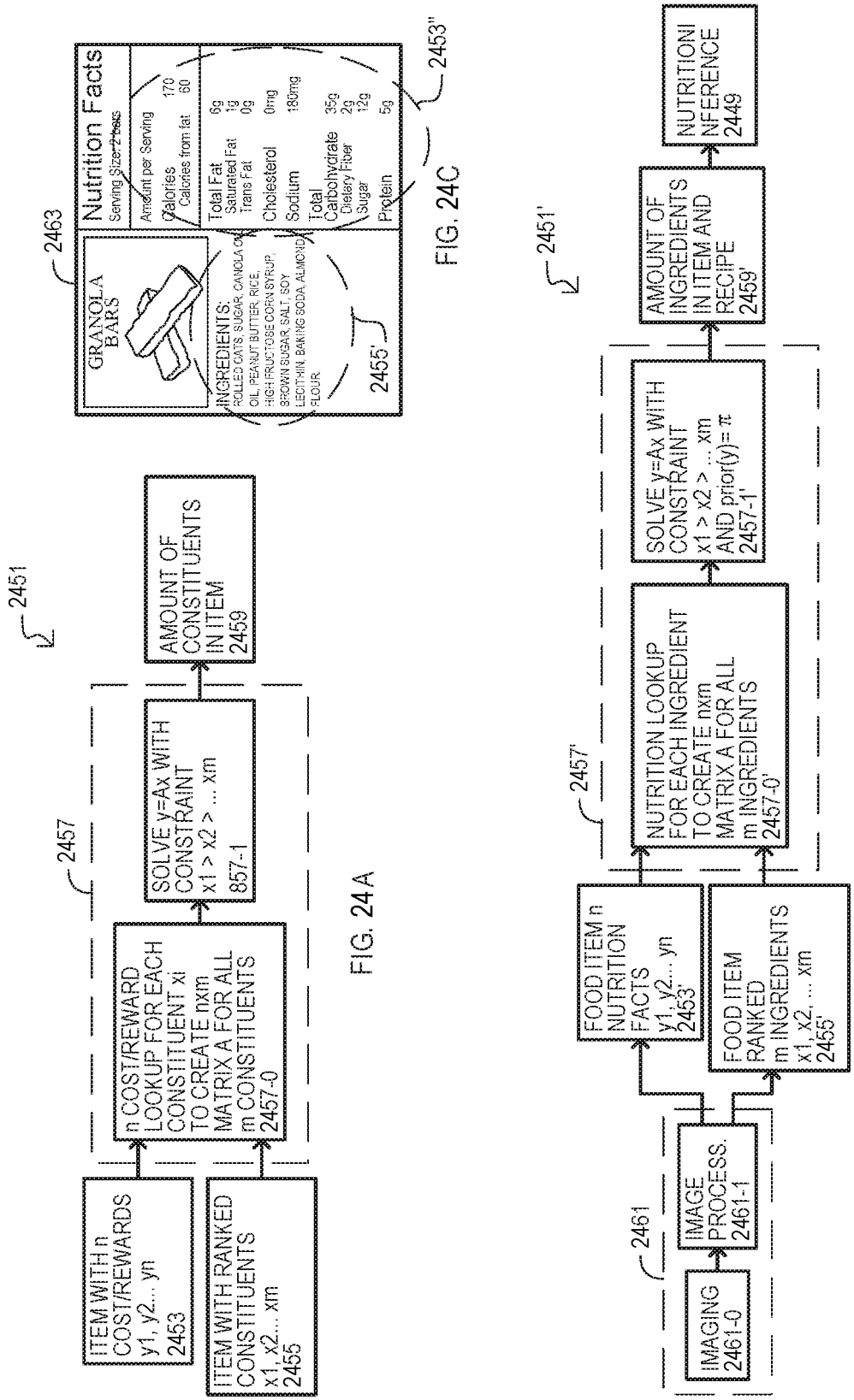

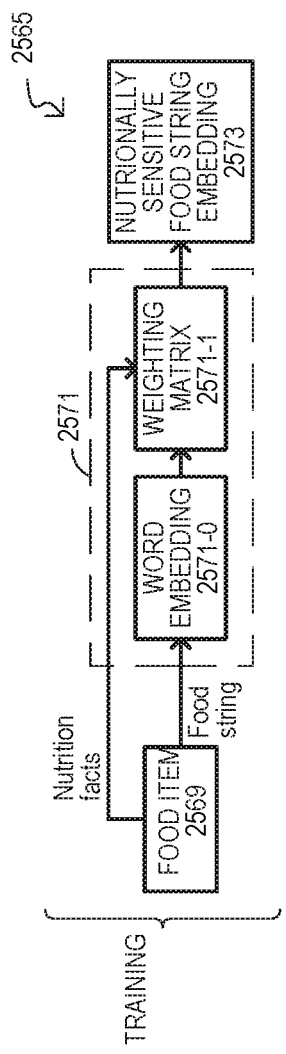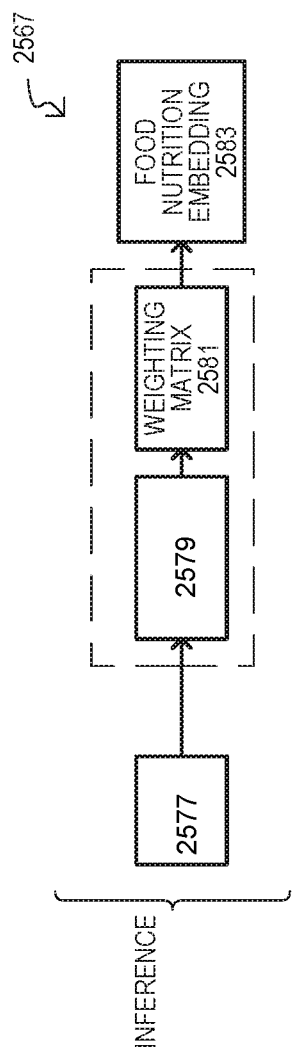
FIG. 25A
FIG. 25B

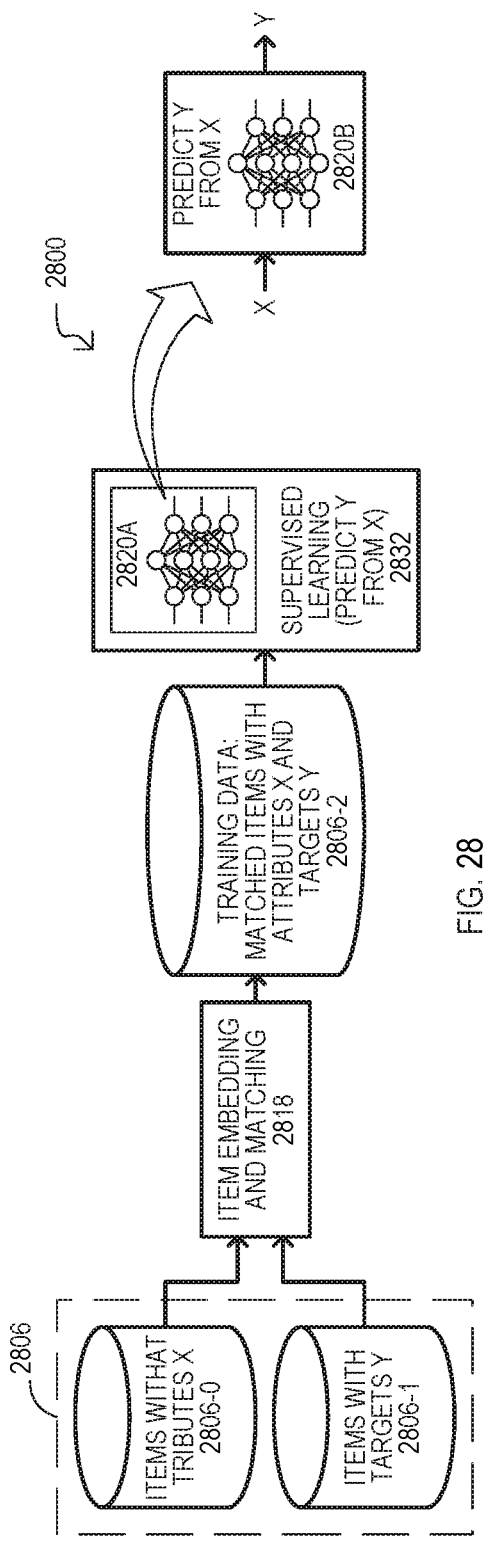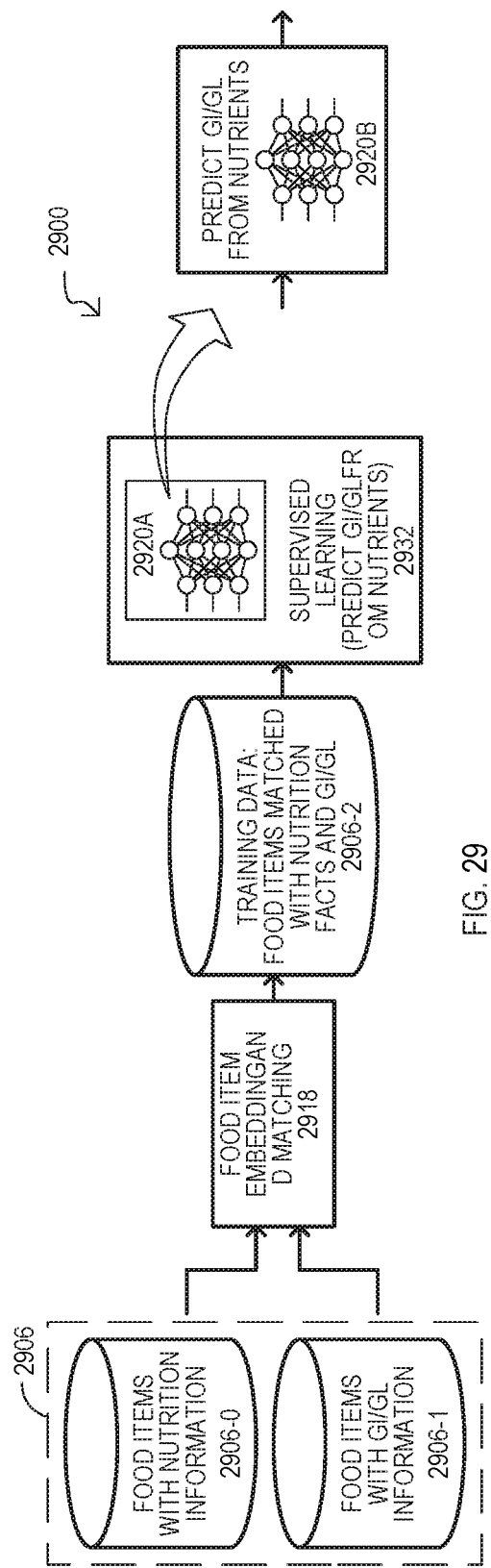
FIG. 28
FIG. 29

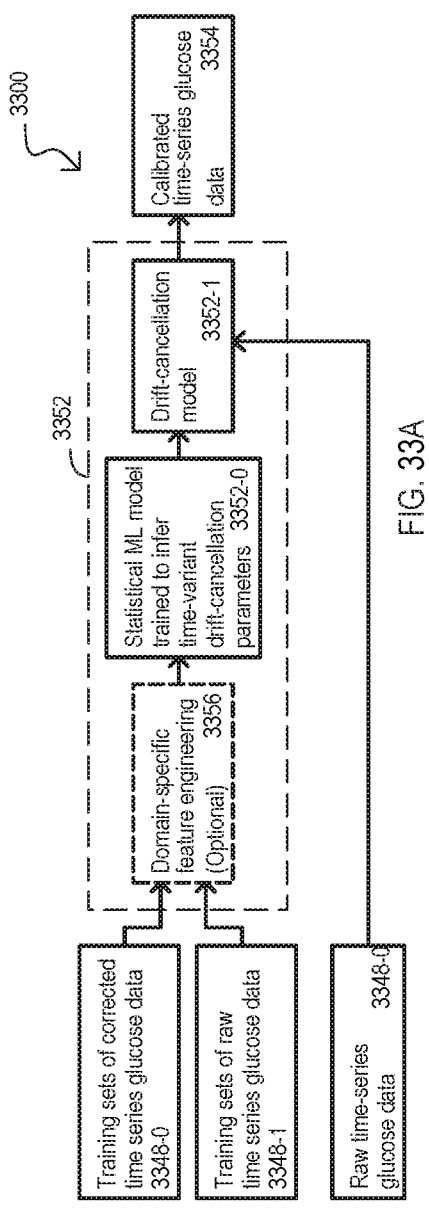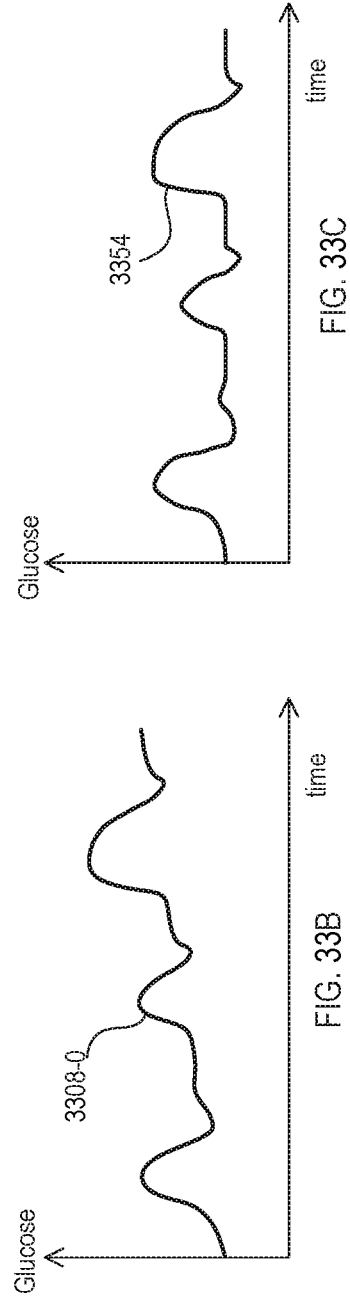
FIG. 33A
FIG. 33B
FIG. 33C

| TIME | DATA1 | DATA2 | DATA3 |
|---|---|---|---|
| 12 | 72 | 65 | Turkey Sandwich, Iced Tea |
| 13 | 76 | 82 | Nothing |
| 14 | 74 | 70 | Banana |
| 15 | 72 | 81 | Nothing |

QUERY(time=1-4, DATA1, DATA2, DATA3)

SYSTEMS, METHODS, AND DEVICES FOR BIOPHYSICAL MODELING AND RESPONSE PREDICTION

CROSS-REFERENCE

This application is a continuation application of International Application No. PCT/US19/63788, filed on Nov. 27, 2019, which claims priority to U.S. Provisional Patent Application No. 62/773,117, filed on Nov. 29, 2018, U.S. Provisional Patent Application No. 62/773,125, filed on Nov. 29, 2018, U.S. Provisional Patent Application No. 62/773,134, filed on Nov. 29, 2018, each of which is incorporated herein by reference in its entirety.

BACKGROUND

Many biological systems, including the human body, can function with a high degree of complexity. Further, while a single species can have an overall general likeness, there can be significant variability between individuals. Consequently, it can be difficult to understand, let alone predict various biological responses on an individual basis.

Understanding human biological responses on an individual basis can provide various health and quality-of-life benefits. Such an understanding can enable an individual to make better choices to improve their health. When such choices are made by a population, the overall health of society can benefit. In addition, such an understanding can empower an individual to better alter their lifestyle in the pursuit of personal goals.

One human biological response of increasing interest is nutrition, and blood glucose levels resulting from eating in particular. Failure to maintain blood glucose levels in acceptable levels over time may result in adverse consequences, including pre-diabetes or Type 2 diabetes. However, individuals can vary in blood glucose response, diet, behavior, and numerous other factors. Accordingly, conventional models (e.g., linear blood glucose response models) can be inadequate understanding an individual's personalized blood glucose response.

SUMMARY

The present disclosure provides systems and methods that can acquire sensor and other data that records subject actions and that utilize reinforcement learning to predict a subject response and the modify the subject's response to achieve a goal. The prediction can be a prediction of a biophysical response and/or behavioral response. Embodiments can utilize custom variational encoding to model subject actions and responses. In some embodiments, the systems described herein can generate a recommendation for a subject based on a reward function and the subject's historical actions.

In one aspect, the present disclosure provides a computer-implemented method for training and using a reinforcement learning algorithm to generate a recommendation that aids a subject in maintaining or adjusting or optimizing a glucose level of the subject with respect to a reward function. The method can comprise: until a convergence condition is achieved, iteratively: (i) generating the recommendation using the reinforcement learning algorithm, which recommendation comprises a recommended meal or physical activity, (ii) processing the recommendation using a biophysical reaction model to generate a predicted glucose response of the subject to following the recommendation, and (iii) applying a reward function to the predicted glucose response to generate a first reward and updating the reinforcement learning algorithm based on the first reward. The method can further comprise providing the recommendation to the subject; measuring a glucose response of the subject to following the recommendation; and applying a second reward function to the measured glucose response to generate a second reward and updating the reinforcement learning algorithm based on the second reward. In some embodiments, the method comprises using the glucose response of the subject to train the biophysical reaction model. In some embodiments, the method comprises encoding the glucose response of the subject into a low-dimension latent space for providing to the biophysical reaction model and to the second reward function. In some embodiments, the first reward function is the same as the second reward function. In some embodiments, the biophysical reaction model includes at least one body model configured to generate a simulated biophysical response of the subject in response to a plurality of inputs. In some embodiments, generating the predicted glucose response of the subject comprises: applying the glucose response of the subject to a predictor trained to infer a future glucose response; applying the recommendation to an adherence model configured to evaluate how closely the subjects will follow the recommendation; and selectively applying outputs of the predictor and the adherence model as the plurality of inputs to the body model. In some embodiments, generating the predicted glucose response further comprises applying the simulated biophysical response to an autoencoder and generative adversarial network to generate the predicted glucose response. In some embodiments, the convergence condition is based at least in part on the magnitude of the first reward.

In another aspect, the present disclosure provides a method that can comprise: training each of a plurality of different autoencoder (AE) temporal convolutional neural networks (CNNs) on historical time series data from one of a plurality of different data sources, wherein the plurality of different data sources comprises a continuous glucose monitor, a heart rate monitor, and a source of food data; generating a plurality of seed values using the plurality of AE temporal CNNs in response to current data from the plurality of different data sources, configuring each of a plurality of different CNN encoders with one of the plurality seed values from a corresponding AE temporal CNN; applying past the historical times series data from the corresponding data sources to the temporal CNN encoders to generate encoded data values; and applying the encoded data values to a forecast configured to generate predicted data values corresponding to one of the data sources. In some embodiments, training the plurality of AE temporal CNNs includes: training a first AE temporal CNN with data from a first type sensor that reads a first biophysical response, and training a second AE temporal CNN with data from a second type sensor that reads a second biophysical response; and applying the encoded data values to generate predicted first biophysical responses.

In another aspect, the present disclosure provides a method that can comprise: receiving reference values over time from a first biophysical sensor that represent at least one biophysical response of a subject, the time including a first time period followed by a second time period; receiving first data values from a second biophysical sensor; inferring first predicted values for the at least one biophysical response with a first subject model using at least first data from the second time period; inferring second predicted values for the at least one biophysical response with a second subject model using at least first data from the first time period; and comparing the first and second predicted values to the reference values to determine the accuracy of the subject models. In some embodiments, inferring second predicted values includes: inferring predicted first data values for the second time period from first data values of the first time period, and applying the first predicted data values for the second time period to the second subject model. In some embodiments, the method further comprises: receiving second data values; inferring first predicted values for the at least one biophysical response further includes using second data from the second time period; and inferring second predicted values for the at least one biophysical response further includes using second data from the first time period. In some embodiments, the method further comprises: in response to at least the reference values and first data values from the first time period, adjusting parameters in the second subject model. In some embodiments, the method further comprises: applying the first predicted values for the at least one biophysical response to a first generative adversarial network to generate first adjusted predicted values; applying the second predicted values for the at least one biophysical response to a second generative adversarial network to generate second adjusted predicted values; and comparing the first and second adjusted predicted values to the reference values to determine the accuracy of the generative adversarial networks. In some embodiments, the method further comprises: in response to comparing the first and second predicted values to the reference values updating at least the first and second body models. In another aspect, the present disclosure provides a system that can comprise: a first data prediction model configured to generate predicted first data values for a second time period from first data values for a first time period which precedes the second time period; a second data prediction model configured to generate predicted second data values for the second time period from second data values for the first time period; a first subject model comprising at least in part an artificial neural network (ANN) configured to infer a first predicted biophysical response from first and second data values from the second time period; a second subject model having a same structure as the first body model configured to infer a second predicted biophysical response from predicted first and second data values for the second time period; and a compare system configured to compare a reference biophysical response for the second time period to the first and second predicted biophysical responses. In some embodiments, the first and second data prediction models comprise long short-term memory networks. In some embodiments, the system further comprises: a third data prediction model configured to generate a predicted reference biophysical response for the second time period from the reference biophysical response for the first time period. In some embodiments, the system further comprises: a parameter estimator configured to update at least the second subject model in response to a reference biophysical response, and the first and second data values from the first time period. In some embodiments, the system further comprises: a feedback generator configured to selectively adjust any of the first data prediction model, a second data prediction model, the first subject model, the second subject model in response to comparison results from the compare system.

In another aspect, the present disclosure provides a method that can comprise: during a first time interval, training a biophysical model comprising an artificial neural network (ANN) to generate a simulated biophysical response of a subject from at least first sensor data and second sensor data, the first sensor data comprising continuous glucose monitoring data and the second sensor data comprising heart rate monitoring data, which training comprises estimating personalized time-varying parameters of the biophysical model; during a second time interval, generating the simulated biophysical response of the subject in real time using the trained biophysical model, the real-time data including the second sensor data but not including the first sensor data. In some embodiments, training the biophysical model includes: applying at least the first sensor data to the biophysical model, and updating the biophysical model using a parameter estimator that evaluates the simulated first biophysical response with respect to a subject's actual first biophysical response. In some embodiments, training the biophysical model includes applying the first sensor data and the second data to the first biophysical model, the second data being different than the first biophysical response. In some embodiments, the second data comprises data logged by the subject.

In another aspect, the present disclosure provides a system that can comprise: a first biophysical model comprising an artificial neural network (ANN) configured to derive network parameters in response to training with data from at least one type of sensor to output a simulated first type biophysical response; a parameter estimator configured to update parameters of the first biophysical model in response to the simulated first type biophysical response and an actual first type biophysical response of a subject; and a second biophysical model comprising an ANN, configured with the network parameters, operable to infer predicted first type biophysical responses in real-time for the subject in response to sensor data received from the at least one type of sensor in real-time. In some embodiments, the actual first type biophysical response is recorded with a first type sensor and the at least one type of sensor is different than the first type sensor. In some embodiments, the at least one type of sensor records a second type biophysical response different from the first type biophysical response. In some embodiments, the actual first type biophysical response is recorded with a first type sensor and the at least one type of sensor is different than the first type sensor. In some embodiments: the first biophysical model derives the network parameters in response to training with data from at least one type of sensor and data from a second source; and the second biophysical model infers predicted first type biophysical responses in response to sensor data received from the at least one type of sensor in real-time and data from the second source received in real-time. In some embodiments, the second source comprises data logged personally by the subject. In another aspect, the present disclosure provides a method that can comprise: receiving time series data from a plurality of different sources that each record data of a different type for at least one subject that performs actions, the different sources including a glucose sensor that records a glucose response of the at least one subject; executing unsupervised learning on the time series data with at least one encoding artificial neural network (ANN) to produce encoded values in a resulting latent space having a predetermined distance from one another; selecting orthogonal values based on the latent space; decoding the orthogonal values with an ANN having a corresponding decoding structure to the encoding ANN to generate decoded values; and mapping the decoded values to subject actions. In some embodiments, executing unsupervised learning includes autoencoding the time series data. In some embodiments, autoencoding the time series data includes autoencoding with a temporal convolutional neural network (NN) variational autoencoder. In some embodiments, the method further comprises filtering the decoded values based on relevance criteria for a particular subject. In some embodiments, the different sources further include a second type sensor that records a second type biophysical response of the at least one subject. In some embodiments, at least one subject action is selected from physical activities of the subject and the ingestion of food by the subject. In some embodiments, at least one of the different sources is selected from the group of accelerometer data, calendar data of the subject, and sleep state of the subject.

In another aspect, the present disclosure provides a system that can comprise: an encoder configured to encode time series data values into encoded values in a latent space having a predetermined metric distance from one another, the time series data being from a plurality of different data sources that record features of at least one subject, at least one time series data being for a first type biophysical response of the at least one subject; a value selector module configured to determine orthogonal values from the encoded values; a decoder having a decoding structure corresponding to the encoder and configured to generate decoded values from the orthogonal values; and an action mapping module configured to map the decoded values to actions of the at least one subject. In some embodiments, the autoencoder comprises a temporal convolutional NN variational autoencoder. In some embodiments, the system further comprises a filtering module configured to selectively discard some of the decoded values based on relevance criteria for a particular subject. In some embodiments, at least another of the time series data is for a second type biophysical response of the at least one subject. In some embodiments, the data sources include a continuous glucose meter, heart rate monitor and food data logged by the at least one subject.

In another aspect, the present disclosure provides a method that can comprise: creating a data object in a system memory of a computing system; copying data into the data object; by execution of a decorator function, transforming the data object into a data processing object having an egress messaging function; processing the data of the data processing object with one of a plurality of different machine learning processes; and upon completing the processing of the data, returning a processing result and executing the egress messaging function. In some embodiments, the plurality of different processes are asynchronous processes, and wherein the method further comprises, upon receiving a message for the egress messaging function: creating a next data object in the system memory; copying next data into data object; by execution of the decorator function, transforming the next data object into a next data processing object having the egress messaging function; and processing data of the next data processing object with one of the machine learning processes. In some embodiments, the processing result comprises a dictionary object that maps keys to values. In some embodiments, the data comprises input data to an artificial neural network (ANN) for learning operations on the ANN. In some embodiments, the data comprises input data to an artificial neural network (ANN) for inference operations on the ANN.

In another aspect, the present disclosure provides a system that can comprise: a data store configured to store data for processing; system memory; a multiprocessing module configured to execute a plurality of machine learning processes in parallel; and a data object decorating function comprising instructions executable by the multiprocessing module and configured to: create a data object in the system memory, copy data into the data object from the data store, transform the data object into a data processing object having an egress messaging function, and instantiate one of the machine learning processes to process the data of the data processing object and return processing results and execute the messaging function to return a message. In some embodiments, the multiprocessing module is resident on a server. In some embodiments, the multiprocessing module is distributed over a plurality of servers. In some embodiments, the machine learning processes include an artificial neural network (ANN). In some embodiments, the ANN is selected from the group consisting of autoencoders (AEs), generative adversarial networks (GANs), long short-term memory networks (LSTMs), convolutional neural networks (CNNs), and reinforcement learning (RL) algorithms.

In another aspect, the present disclosure provides a method that can comprise: creating a biophysical model with at least one machine learning architecture to predict a first biophysical response, wherein the biophysical model has been trained with at least primary sensor data and secondary sensor data, the primary sensor data capturing a first biophysical response, the secondary sensor data capturing a second biophysical response; in response to at least the secondary sensor data and not the primary sensor data, predicting a first biophysical response of the subject with the biophysical model; determining if the predicted first biophysical response is outside of predetermined limits; and if the predicted first biophysical response is outside of predetermined limits, transmitting at least one recommendation to the subject, the at least one recommendation selected to adjust the subject's actual biophysical response to be within the predetermined limits. In some embodiments, the method further comprises setting the predetermined limits according to the subject's health status. In some embodiments, the method further comprises setting the predetermined limits according to a subject's health goals. In some embodiments, the first biophysical response includes a glucose response of the subject. In some embodiments, the second biophysical response includes a heart rate of the subject. In some embodiments, the biophysical model is also trained with data logged by the subject. In some embodiments, the primary sensor data is generated from a continuous glucose monitor; the secondary sensor data is generated from a heart rate monitor; and the data logged by the subject is food eaten by the subject. In some embodiments, the at least one recommendation is selected from a physical activity recommendation and a food recommendation. In some embodiments, the biophysical model comprises an artificial neural network configured as an autoencoder. In some embodiments, the biophysical model comprises an artificial neural network configured as at least a long short-term memory (LSTM) configured to predict a first biophysical response from a recommendation. In some embodiments, the biophysical model comprises an artificial neural network configured as at least one temporal convolutional neural network configured to predict a first biophysical response of the subject. In some embodiments, the at least one recommendation is selected from a recommendation set including canonical actions derived by autoencoding heterogenous sensor data. In some embodiments, the method further comprises, if the predicted first biophysical response is not outside of predetermined limits, transmitting a predetermined message. In some embodiments, the predetermined message is selected from the group of: an encouragement message and a reward. In some embodiments, the method further comprises displaying the at least one recommendation on a subject device. In some embodiments, the method further comprises capturing at least the secondary sensor data with an application executable on a subject device. In some embodiments, the method further comprises capturing the primary data with the application.

In another aspect, the present disclosure provides a method that can comprise: training a glucose regulation model having at least one first parameter to predict glucose levels in response to at least food source data; in response to information on a subject, substituting the at least one first parameter with at least one personalized parameter in the glucose regulation model to create a personalized glucose regulation model; and applying food source data from the subject to the personalized glucose regulation model to predict a glucose level of the subject. In some embodiments, the glucose regulation model includes at least one neural network. In some embodiments, the glucose regulation model includes at least one statistical model selected form the group consisting of: a long short-term memory neural network and recurrent neural network. In some embodiments, the glucose regulation model includes at least one neural network trained with data of a predetermined population. In some embodiments, the at least one first parameter comprises an insulin resistance parameter. In some embodiments, the glucose regulation model includes at least one glucose model selected from the group consisting of: a differential equation model of glucose regulation and a glucose model comprising a set of coupled equations. In some embodiments, the at least one differential equation model of glucose regulation includes a food source function. In some embodiments, the method further comprises: training the food source function with at least training data selected from the group consisting of: glycemic responses of a population to predetermined foods, and glycemic responses calculated from data for predetermined foods. In some embodiments, the method further comprises generating the personalized parameters of the subject by recording a glucose response of the subject with a glucose meter. In some embodiments, the method further comprises generating the personalized parameters of the subject by classifying the subject into a demographic equivalent group based on characteristic data of the subject.

In another aspect, the present disclosure provides a system that can comprise: a computing system comprising a glucose prediction model comprising at least one model parameter operable to predict glucose levels in response to at least food source data; a model parameter input configured to receive at least one personalized parameter as the at least one model parameter, the at least one personalized parameter generated in response to data of a subject; and a food source data input configured to apply food source data to the glucose prediction model with the at least one personalized parameter to predict a glucose level of the subject. In some embodiments, the glucose regulation model comprises a neural network. In some embodiments, the glucose regulation model comprises a statistical model selected from the group consisting of: a long short-term memory neural network and recurrent neural network. In some embodiments, the glucose regulation model comprises at least at least one neural network trained with data from a predetermined population. In some embodiments, the at least one model parameter includes an insulin resistance parameter. In some embodiments, the glucose regulation model is derived with supervised training based on at least one model of glucose regulation selected from the group consisting of: a differential equation model of glucose regulation and a glucose model comprising a set of coupled equations. In some embodiments, the at least one differential equation model of glucose regulation includes a food source function. In some embodiments, the food source function comprises at least one neural network trained with training data selected from the group of: glycemic responses of a population to predetermined foods, and glycemic responses calculated from data for predetermined foods. In some embodiments, the system further comprises an electronic device configured to generate the food source data. In some embodiments, the system further comprises a memory coupled to the model parameter input and configured to store the personalized parameters.

In another aspect, the present disclosure provides a method that can comprise: training, on a plurality of attributes, a first neural network (NN) to impute a first subset of the plurality of attributes from a second subset of the plurality of attributes; training a second NN to predict a target value from the first subset of the attributes and the second subset of attributes; receiving a subset of input attributes of a plurality of input attributes from a subject; using the first NN to impute remaining input attributes in the plurality of input attributes; and processing the first subset of inputs attribute and the remaining input attributes with the second NN to predict a target value. In some embodiments, the first NN comprises an autoencoder. In some embodiments, the second NN comprises a bidirectional recurrent NN. In some embodiments, the recurrent NN is a long short-term memory NN. In some embodiments, the second subset of the plurality of attributes and the subset of input attributes comprise nutrition data for food; and the predicted target value is a glycemic value.

In another aspect, the present disclosure provides a system that can comprise: a subject data input configured to receive input attributes from a subject; a first neural network (NN) trained to impute related attributes from input attributes by randomly selecting attributes from sets of attributes having associated target values, and configured to sequentially receive the input attributes; a second NN trained to predict a target value from related attributes and the input attributes, and configured to receive the input attributes and the related attributes generated by the first NN; and a subject data output configured to output and update a predicted target value from the second NN in response to the application of each input attribute to the first and second NNs. In some embodiments, the system further comprises: a data store configured to store training input attributes and corresponding training target values for training the first and second NNs. In some embodiments, the first NN comprises an autoencoder. In some embodiments, the second NN comprises a bidirectional recurrent NN. In some embodiments, the recurrent NN is a long short-term memory NN.

In another aspect, the present disclosure provides a method that can comprise: receiving sensor data from at least one sensor that generates biophysical readings for a subject; by operation of a first neural network (NN), embedding the sensor data to generate embedded values; by operation of a second NN, generating imputed embedded values in response to the embedded values, the imputed embedded values including imputed values corresponding to one or more regions of the sensor data; and normalizing the embedded imputed values to generate imputed values. In some embodiments, the regions do not include data that is usable. In some embodiments, receiving sensor data includes receiving data from a first sensor and a second sensor different from the first sensor; and embedding the sensor data includes concatenating data from the first and second sensors. In some embodiments, the first sensor is a glucose monitor. In some embodiments, the second sensor is a heart rate monitor. In some embodiments, the second NN comprises an autoencoder.

In another aspect, the present disclosure provides a system that can comprise: at least one biophysical sensor that generates sensor data having missing regions where biophysical readings are determined to be invalid or missing; a first neural network (NN) configured to embed data values from the at least one sensor to generate embedded values; a second NN configured to generate imputed embedded values in response to the embedded values, the imputed embedded values including imputed values corresponding to the missing regions of the sensor data; and a normalizing system configured to normalize the embedded imputed values to generate imputed values. In some embodiments, the at least one sensor includes a first sensor and a second sensor different than the first sensor; and the first NN is configured to embed sensor data from the first and second sensors in a same time period into single values. In some embodiments, the first sensor is a glucose sensor. In some embodiments, the second sensor is a heart rate monitor. In some embodiments, the second NN comprises an autoencoder.

In another aspect, the present disclosure provides a method that can comprise: receiving a validated data set and a query data set, each data set including data values with labels; by operation of a neural network (NN), classifying the validated data set and query data sets with a probabilistic classifier conditioned on the data set values and target labels; and generating a quality score based on a classification result for all data values of one data set. In some embodiments, the method further comprises generating the query data set, including taking biometric sensor readings with corresponding actions as labels. In some embodiments, the biometric sensor comprises a glucose meter. In some embodiments, the labels comprise food log data. In some embodiments, a distribution of the data values has the form p(X, Y, Z) where X is the input distribution, Y is a categorical target of the probabilistic classifier, and Z varies according to which data set the values belong to. In some embodiments, a classification of the probabilistic classifier takes the form $h(x)=p(z=1|x, Y=1)$, and z equals 0 if x is from the data set with validated labels and Z equals 1 if x is from the query data set.

In another aspect, the present disclosure provides a system that can comprise: a data storage system configured to store data sets including data values with labels, the data sets including at least a validated data set and a query data set; and an electronic system in communication with the data storage system that includes at least one neural network configured as a probabilistic classifier configured to classifying the validated data set and query data sets with conditioned on the data set values and target labels, and a quality section configured to examine a classification value for all data values in the query or validated data set and generate a quality value in response thereto. In some embodiments, the system further comprises: at least one biometric sensor configured to generate data values for the query data set. In some embodiments, the biometric sensor comprises a glucose meter. In some embodiments, the validated and query data sets include blood glucose levels with food logs as labels. In some embodiments, a distribution of the data values has the form p(X, Y, Z) where X is the input distribution, Y is a categorical target of the probabilistic classifier, and Z varies according to which data set the values belong to. In some embodiments, a classification of the probabilistic classifier takes the form $h(x)=p(X=1|x, Y=1)$, and Z equals 0 or 1 depending upon whether x is from the validated data set or query data set.

In another aspect, the present disclosure provides a method that can comprise: storing biophysical sensor signals and logged behavior corresponding to the biophysical sensor signals in a data storage device, the stored data comprising training data; training a neural network on the training data to classify biophysical sensor signals as resulting in target behaviors; receiving input biophysical sensor data; and processing the input biophysical sensor data using the neural network to classify a target behavior that results from the input biophysical sensor data. In some embodiments, the biophysical sensor signals include glucose sensor signals and the logged behavior includes logged food data. In some embodiments, the biophysical sensor signals include heart rate monitor signals and the logged behavior includes logged food data. In some embodiments, the target behavior is predicted food consumption. In some embodiments, the method comprises: acquiring the input biophysical sensor signals with at least one sensor for a subject; transmitting the input biophysical sensor signals to the neural network; and transmitting the target behavior to a device of the subject.

In another aspect, the present disclosure provides a system that can comprise: a storage system configured to store training data comprising training sensor data and corresponding behavior data; at least one biophysical sensor configured to generate and transmit subject sensor data; and a behavior prediction system configured to receive the subject sensor data and comprising at least one electronic system comprising a neural network trained as a classifier that classifies the subject sensor data into a target behavior, the classifier trained with the training data. In some embodiments, the training data comprising training sensor data from a plurality of different biophysical sensors; and the at least one biophysical sensor includes the plurality of different biophysical sensors. In some embodiments, the training sensor data includes glucose levels and the behavior data includes logged food corresponding to the glucose level; the at least one biophysical sensor includes a glucose meter; and the target behavior is predicted food ingestion. In some embodiments, the training sensor data includes heart rate data and the behavior data includes logged food corresponding to the heart rate data; the at least one biophysical sensor includes a heart rate monitor; and the target behavior is predicted food ingestion. In some embodiments, the system further comprises: the behavior prediction system is further configured to transmit the target behavior; and a subject device configured to receive the target behavior.

In another aspect, the present disclosure provides a method that can comprise: receiving and storing string data corresponding to a description of a food item; applying the string data to a language processor configured to determine nominative words and non-nominative words from the string data; in response to the nominative words, querying an item database with the nominative words; in response to non-nominative words, querying the item database with the non-nominative words; and generating a list of query results in response to the querying, the list of query results comprising recipes for the food items. In some embodiments, the method further comprises: the language processor is further configured to determine nominative words as explicit ingredients; and filtering the responses to the querying with the explicit ingredients to generate the list of query results.

In another aspect, the present disclosure provides a system that can comprise: a storage device configured to store a database comprising descriptions of food items; a language processing system comprising at least one computing device configured to process text strings to determine nominative and non-nominative words; a query system comprising at least one computing device configured to apply first queries to the database in response to the nominative words generated by the language processing system and to apply second queries to the database in response to the non-nominative words to generate a list of query results in response to the queries, the list of query results comprising recipes for the food items. In some embodiments, the language processing system is further configured to determine nominative words as explicit ingredients; and the query system is further configured to filter responses to the first or second queries.

In another aspect, the present disclosure provides a method that can comprise: receiving and storing first data comprising properties of an item; receiving and storing second data comprising constituents of the item ranked in order of prevalence in the item; determining the properties for at least one of the ranked constituents in a database to generate look-up data; determining at least one amount of the at least one constituent in the item in response to the look-up data; and storing the at least one amount of the at least one constituent as output data. In some embodiments, receiving and storing first data includes receiving nutrition information for a food item; and receiving and storing second data includes receiving ranked ingredient data for the food item. In some embodiments, receiving and storing first and second data includes capturing and processing image data of a food label of the food item. In some embodiments, the first data includes n properties; second data includes m constituents; determining the properties for each constituent includes creating and storing an n×m matrix of constituents and their properties; and determining the amount of each constituent in the item includes solving a system of equations corresponding to y=Ax, where y is the amount of an ingredient, x is a constituent and A is the matrix. In some embodiments, determining the amount of each constituent includes applying the matrix A to a neural network configured for linear regression analysis.

In another aspect, the present disclosure provides a system that can comprise: a data pre-processing section coupled to receive first data comprising properties of an item and second data comprising constituents of the item having a ranked in order of prevalence in the item, and including a processing device configured to create a data structure that represents properties for each constituent; and an analysis section coupled to receive the data structure and including a processing device configured to determine determining the amount of each constituent in the item. In some embodiments, the system further comprises: an input device configured to capture the first and second data for the item. In some embodiments, the input device comprises an image capture device configured to capture the image of a label for the item. In some embodiments, the first data comprises nutrition information of a food item and the second data comprises ingredients of the food item. In some embodiments, the first data includes n properties; second data includes m constituents; the data structure comprises a topological mapping of constituents and their properties; and the analysis section is configured to solve a system of equations corresponding to y=Ax, where y is the amount of an ingredient, x is a constituent and A is the topological mapping. In some embodiments, the topological map is a matrix and the analysis section comprises a neural network configured for linear regression analysis.

In another aspect, the present disclosure provides a method that can comprise: receiving and storing first data comprising properties of an item; receiving and storing second data comprising constituents of the item ranked in order of prevalence in the item; determining the properties for at least one of the ranked constituents in a database to generate look-up data; determining at least one amount of the at least one constituent in the item in response to the look-up data; and storing the at least one amount of each constituent as output data.

In another aspect, the present disclosure provides a method that can comprise: training a word embedding system having a weighting matrix with training data comprising string descriptions of items and properties of the items to embed the string descriptions of items into an embedded space weighted according to the properties of the items; and applying an input string description of the item to the trained word embedding system to infer an output word embedding weighted according to the properties of the items. In some embodiments, training the word embedding system includes training with food string descriptions with nutrition information as the properties. In some embodiments, applying the input string includes applying a string description of a food item.

In another aspect, the present disclosure provides a system that can comprise: a storage system configured to store training data that includes string descriptions of items and properties of the items; a word embedding system using a neural network trained with the training data to embed words of the string descriptions into an embedded space with a weighting derived from the properties of an item corresponding to one of the string descriptions; and an input configured to receive an input string and apply it to the word embedding system to generate word embeddings weighted according to the properties. In some embodiments, the training data includes word description of food items and nutrition information for the food items. In some embodiments, the input string includes a description of the food item and the generated word embeddings are weighted according to the nutrition information.

In another aspect, the present disclosure provides a method that can comprise: training a word embedding system having a weighting matrix with training data comprising string description of items and properties of the items to embed the word string items into an embedded space weighted according to the properties of the corresponding item; and applying an input string description of the item to the trained word embedding system to infer output word embedding with the property weighting.

In another aspect, the present disclosure provides a system that can comprise: a storage system configured to store training data that includes string descriptions of items and properties of the items; a neural network configured as word embedding system trained with the training data to embed words of the strings descriptions into an embedded space with a weighting derived from the properties of the item corresponding to the string description; and an input configured to receive an input string and apply it to the trained word embedding system to generate word embeddings weighted according to the properties.

In another aspect, the present disclosure provides a method that can comprise (a) obtaining text-based descriptions of a plurality of food items and, for each of the plurality of food items, (i) nutrition data and a glycemic value or (ii) nutrition data or a glycemic value; (b) generating embeddings of the text-based descriptions of the plurality of food items; (c) inferring, based at least on the embeddings, a glycemic value for each food item in the plurality of food items for which a glycemic value was not obtained and nutrition data for each food item in the plurality of food items for which nutrition data was not obtained; (d) training a supervised machine learning algorithm on the nutrition data and the glycemic values of the plurality of food items to predict a glycemic value of a given food item from nutrition data of the given food item. In some embodiments, the method comprises providing the glycemic value of the given food item to the supervised machine learning algorithm to predict the glycemic value of the given food item. In some embodiments, the glycemic value is a glycemic index or a glycemic load. In some embodiments, (b) comprises applying an unsupervised learning algorithm to the text-based descriptions of the plurality of food items. In some embodiments, the unsupervised learning algorithm is a dimensionality reduction algorithm. In some embodiments, the unsupervised learning algorithm is an n-gram or bag-of-words model. In some embodiments, the supervised machine learning algorithm is a deep neural network.

In another aspect, the present disclosure provides a system that can comprise: a data storage system configured to store at least a first database and a second database, the first database including descriptions of first items with corresponding attributes, the second database including descriptions of second items with corresponding target values, at least some of the first items being different than the second items; an embedding system comprising at least a first computing device configured to merge the first and second databases to generate training data that includes merged item descriptions with corresponding attributes and target values; and at least a first inference system comprising a machine learning system trained with the training data to infer target values from attributes. In some embodiments, the descriptions of items comprise word descriptions. In some embodiments, the items are food items, the attributes are nutrition data of the food items, and the target values are glycemic response values. In some embodiments, the glycemic response values are selected from the group of: a glycemic index and a glycemic load. In some embodiments, the system can further comprise a data capture section configured to acquire nutrition data with at least a subject device, and wherein the at least first inference system is configured to infer a glycemic index value from at least the acquired nutrition data. In some embodiments, the system can further comprise at least a second inference system that is configured to determine a blood glucose value of a subject in response to at least glycemic response values of foods indicated as ingested by the subject. In some embodiments, the embedding system comprises at least one neural network configured to embed descriptions of first and second items into an embedded space.

In another aspect, the present disclosure provides a system that can comprise: a data acquisition system configured to acquire attribute values for items; and at least a first inference system configured to infer target values from the acquired attribute values, the first inference system including: at least one neural network trained with training data generated by embedding at least a first data set and second data set, the first data set including descriptions of items with corresponding attributes, the second data set including descriptions of items with corresponding target values. In some embodiments, the system further comprises a training agent configured to train the at least one neural network with the training data. In some embodiments, the system further comprises at least a second inference system configured to infer a response for a subject from at least inferred target values. In some embodiments, the target values are glycemic response values for food items, and wherein the attribute values are nutrition values of the food items. In some embodiments, at least the attribute values are text values embedded into a vector space. In some embodiments, the system further comprises an application server configured to transmit data to an application executed on a subject device in response to at least the inferred target values.

In another aspect, the present disclosure provides a method that can comprise: training a neural network with time series training data of a first modality and time series training data of a second modality to create a first model that generates time series data of the second modality from time series data of the first modality; training a second model with the generated time series of the second modality, time series training data of a third modality, and time series data of a fourth modality to generate time series data of the fourth modality; until a convergence condition is reached, iteratively testing the second model on the time series data of the first modality and the time series data of the third modality; and responsive to reaching the convergence condition, predicting second modality data by testing the second model with data of the first modality. In some embodiments, the method comprises: acquiring the time series training data of the first modality with a first type sensor, and acquiring the time series training data of the second modality with a second type sensor. In some embodiments, the second type sensor is a glucose meter, and wherein the time series data of the second modality includes glucose levels over time. In some embodiments, training the neural network to create the first model includes training with N sets of time series training data, and wherein training the first model with the estimated time series training data of the first modality and time series training data of at least the third modality includes training with M sets of time series data. In some embodiments, the method comprises testing the first model with the N sets of time series data and the M sets of time series data and updating the first model in response to error values of the testing, and wherein the trained first model is the first model with the smallest error. In some embodiments, reaching a convergence condition includes calculating an error value not greater than a threshold.

In another aspect, the present disclosure provides a system that can comprise: an initial model section that includes a first model trained to generate time series data of a second modality from time series data of a first modality with M sets of training data; a training section that includes: a second model derived from the first model and configured to generate time series data of at least a third modality from at least time series data of a fourth modality with N sets of training data, and a testing section configured to test the second model with the M and N sets of training data, and update the second model in response to test error values; and an inference model that is the second model with the lowest test error value, configured to infer time series data of the second modality from time series data of the first modality. In some embodiments, the first model, the second model and the inference model comprise neural networks. In some embodiments, the time series data of the first and second modalities are biophysical sensor data. In some embodiments, at least the time series data of the first and second modalities are glucose levels corresponding to glucose meters. In some embodiments, the third and fourth modalities are glucose levels. In some embodiments, the training section comprises: an inverse model that is an inverse of the first model and configured to generate estimated time series data of the first modality from the time series data of the third and a fourth modality; an estimator section configured to generate linear parameters from the estimated time series data of the first modality and the time series data of the third modality; section configured to generate mapped time series data of the first modality from time series data of the third modality using the linear parameters, wherein the second model is trained with the mapped time series data of the first modality.

In another aspect, the present disclosure provides a method that can comprise: training a neural network with time series training data of a first modality and time series training data of a second modality to create a first model that generates time series data of the second modality from time series data of the first modality; until a convergence condition is reached: using a second model to generate estimated time series data of the first modality from a mixture of time series data from a third modality and a fourth modality, wherein the second model is initiated as an inverse model of the first model; using the estimated time series data of the first modality and time series data of the third modality, training the second model to estimate linear fitting parameters; using the estimated linear fitting parameters to generate analogous time series data of the first modality from the time series data of the third modality; linearly mapping the analogous time series data of the first modality to the time series data of the third modality; training a third model using the linearly mapped analogous time series data from the first modality mixture of time series data of the third modality and time series data of the fourth modality to generate a mixture of time series data from the third modality and time series data from the fourth modality, wherein the third model is an inverse of the second model; modifying the second model to be an inverse model of the third model; and evaluating whether the convergence condition has been reached. In some embodiments, training the third model includes initializing the third model as the first model.

In another aspect, the present disclosure provides a method for training a neural network to calibrate time series data. The method can comprise receiving calibrated time series data for a biophysical response and corresponding raw time series data for the biophysical response; training, on the calibrated time series data and the corresponding raw time series data for the biophysical response, a neural network to generate calibrated time series data, which training comprises updating parameters of the neural network based on a difference between (i) an output of the neural network for a given raw time series and (ii) a corresponding calibrated times series; receiving raw input time series data generated by a biophysical sensor; and generating calibrated time series data by applying the raw input time series data to the neural network. In some embodiments, the raw input time series data is generated by a glucose meter. In some embodiments, the neural network is trained to cancel drift present in the raw input time series data. In some embodiments, the raw time series data and raw input time series data are generated by glucose meters. In some embodiments, training the neural network further comprises domain specific feature engineering. In some embodiments, training the neural network comprises unsupervised training.

In another aspect, the present disclosure provides a method that can comprise: building data structures from a plurality of data sets having an ordering, the data structures including interval trees based on the ordering; determining if any structures have missing intervals in the interval tree; if a data structure has a missing interval, creating data for the missing interval by imputing data values for the missing interval; accessing the data structures by at least searching the interval trees in response to query data; and forming a tabular data structure from the accessed data values that includes a column reflecting the ordering. In some embodiments, the data sets comprise actions ordered in time. In some embodiments, determining if any of the data structures have missing intervals includes classifying data structures into a first class if they have no missing intervals and a second class if they have missing intervals. In some embodiments, accessing data values from the data structures includes an operation selected from the group consisting of: selecting a data structure for a query operation; querying a region of a data structure dictated by the ordering; joining query results; and merging overlapping regions of different data structures. In some embodiments, forming the tabular data structure includes forming a dataframe from the accessed data values. In some embodiments, forming the tabular data structure includes forming a dataframe from the accessed data values. In some embodiments, the data sets comprise different subject events having an ordering, and wherein forming the tabular data structure includes forming a tabular data structure that includes different subject events over a queried time period. In some embodiments, at least one of the subject events is a biophysical response of the subject. In some embodiments, the biophysical response is a glucose level of the subject.

In another aspect, the present disclosure provides a system that can comprise: a data store configured to store tabular data sets, each having data values with an ordering; and memory comprising machine-executable instructions that when executed by a processor cause the processor to perform operations comprising: create data structures that include interval trees based on the ordering, determining if any of the interval trees includes missing intervals, if an interval tree has a missing interval, imputing data for the missing interval, accessing data values from the data structures by at least searching the interval trees of the data structures in response to query data, and forming a tabular data structure from the accessed data values that includes a column reflecting the ordering. In some embodiments, the data store is configured to store tabular data sets having time or date column corresponding to subject actions. In some embodiments, the processing section is configured to execute an operation selected from the group consisting of: selecting a data structure query operation; querying a region of a data structure dictated by the ordering; joining query results; and merging overlapping regions of structures. In some embodiments, the data store is configured to store tabular data sets comprising different subject events having an ordering, and wherein the processing section is configured to forming tabular data structures that includes different subject events over a queried time period. In some embodiments, at least one of the subject events is a biophysical response of the subject. In some embodiments, the biophysical response is a glucose level of the subject.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12B is code showing a method for decorating data objects for post process messaging according to an embodiment;

FIG. 20A is a block diagram showing a system and method for imputing data values for missing portions of a sensor data set according to an embodiment;

FIG. 20B is a block diagram showing a system and method for imputing data values for one sensor based a model created with multiple sensors according to an embodiment;

FIGS. 20C and 20D are diagrams showing one example of data imputation according to an embodiment;

FIG. 24A is a block diagram of a system and method for determining the formula of an item from a text description of the item according to an embodiment;

FIG. 24B is a block diagram of a system and method for determining the amount of ingredients in a food item based on ranked ingredients according to an embodiment. FIG. 24C is a diagram showing one example of food item data that can be acquired in an embodiment like that of FIG. 24B;

FIGS. 25A and 25B are block diagrams of a system and method for embedding food string data into space weighted with nutrition information according to an embodiment;

FIG. 28 is a block diagram showing a system and method for creating a model for predicting a target value from attribute values from data sets that match targets with items and attributes with items according to an embodiment;

FIG. 29 is a block diagram showing a system and method for creating a model for predicting glycemic values from nutrition facts from data sets that match food items with nutrition facts and food items with glycemic values according to an embodiment;

FIG. 33A is a block diagram showing a system and method for creating a drift cancellation model for calibrating time series glucose data. FIGS. 33B and 33C are diagrams of raw and calibrated time series data;

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The present disclosure provides systems and methods that can acquire sensor and other data that records subject actions and utilize reinforcement learning to predict a subject response. The prediction can be a prediction of a biophysical response and/or behavioral response. Embodiments can utilize custom variational encoding to model subject actions and responses. In some embodiments, the systems described herein can generate a recommendation for a subject based on a reward function and the subject's historical actions.

Figure 1:
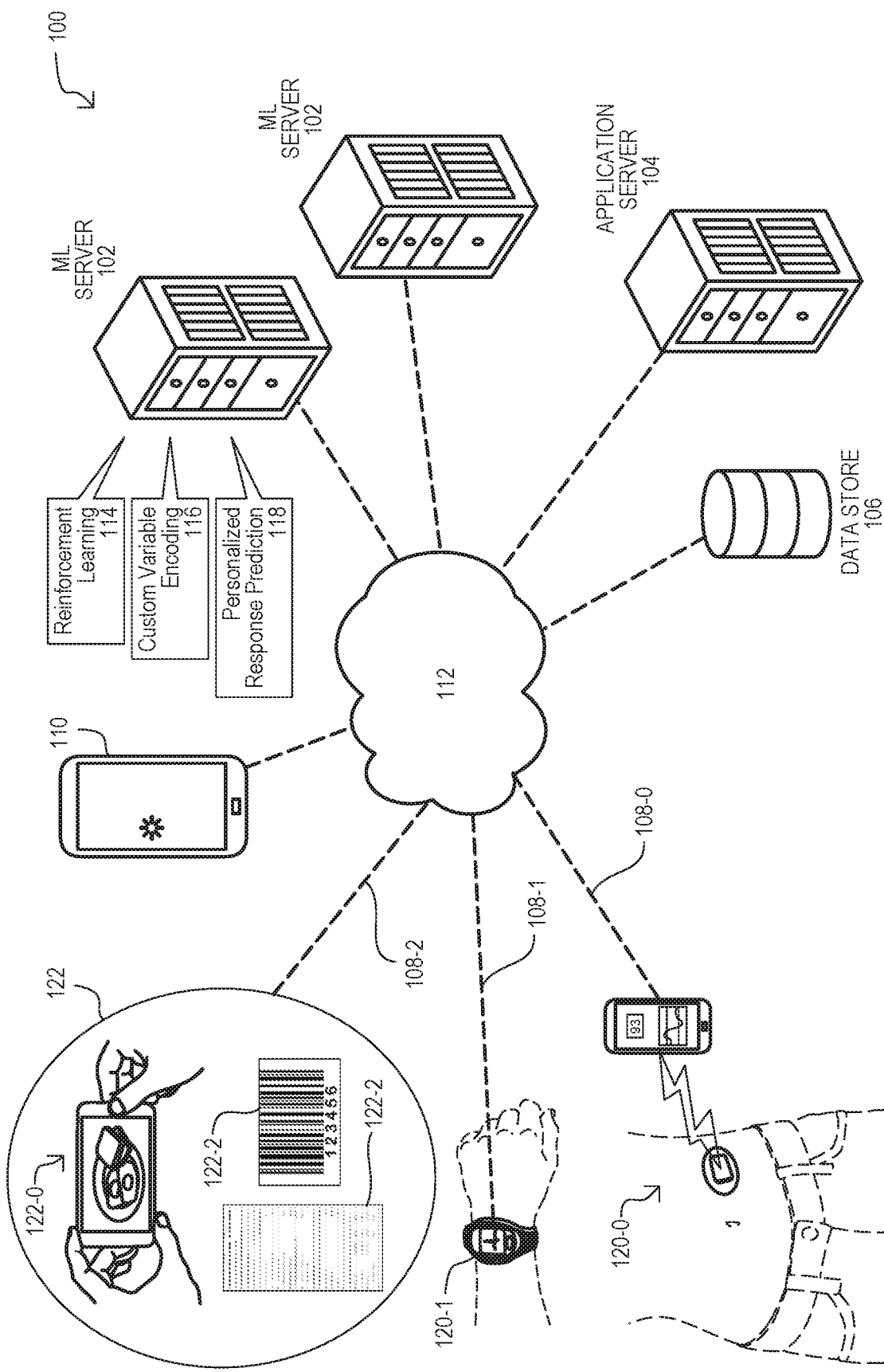
FIG. 1 is a block diagram of a system according to an embodiment.

FIG. 1 shows a system 100 according to an embodiment. The system 100 can include one or more of any of the following: machine learning (ML) servers 102, application servers 104, a data store 106, data sources 108-0 to 108-2, and subject device 110. The data sources 108-0 to 108-2, ML and application servers (102, 104) and subject devices 110 can be in communication with one another through a communication network 112. The communication network 112 can be wired or wireless. For example, the communication network 112 can be a Bluetooth network, a Wi-Fi network, a local area network, a wide area network, a cellular network, or the like. In some cases, the communication network 112 can be the Internet.

The ML servers 102 can include appropriately-programmed hardware for implementing the various ML systems and functions described herein. The hardware can be general-purpose processors, graphics processing units (GPUs), application-specific integrated circuit (ASIC), or machine learning accelerators, to name a few examples. The ML servers 102 can implement artificial neural networks (ANN) of various architectures as will be described herein. Such ANNs can perform various functions, including learning and inference operations on data received from data sources 116, 118, and 120 as well as other data residing on the date store 122. The ANNs can autoencoders (AEs), generative adversarial networks (GANs), long short-term memory networks (LSTMs), convolutional neural networks (CNNs), reinforcement learning (RL) algorithms, and any other artificial neural network (ANN) or related architecture suitable for the systems and methods described herein.

In general, the ML algorithms implemented on the ML servers 102 can be used to predict a subject's biophysical response (e.g., a glucose response) or make a recommendation (e.g., a diet or physical activity recommendation) that is configured to alter or maintain an aspect of the subject's health (e.g., glucose level). The ML algorithms can be supervised learning algorithms, semi-supervised learning algorithms, unsupervised learning algorithms, reinforcement learning algorithms, or the like.

A supervised ML algorithm can be trained using labeled training inputs, i.e., training inputs with known outputs. The training inputs can be provided to an untrained or partially trained version of the ML algorithm to generate a predicted output. The predicted output can be compared to the known output, and if there is a difference, the parameters of the ML algorithm can be updated. A semi-supervised ML algorithm can be trained using a large number of unlabeled training inputs and a small number of labeled training inputs. An unsupervised ML algorithm, e.g., a clustering or dimensionality reduction algorithm, can find previously unknown patterns in data sets without pre-existing labels.

A reinforcement learning algorithm may seek an optimal solution to a problem by balancing exploration of uncharted territory with exploitation of current knowledge. In reinforcement learning, labeled input-output pairs need not be used. Instead, an agent (e.g., an ML algorithm) can choose an action from a set of available actions. The action may result in a new environmental state. The new environmental state may have a reward associated with it, and the reward may be positive or negative depending on whether the new state is better or worse than the previous state. The goal of the agent may be to collect as much reward as possible, e.g., optimize a subject's glucose level. The set of available actions from which the agent can choose may be a probability distribution of actions. The probability distribution may be adjusted as the agent receives rewards. That is, actions that result in negative rewards may be slowly filtered out of the probability distribution, while actions that result in positive rewards may be emphasized in the probability distribution. In the context of biophysical responses, the state may be a subject's glucose level, and the reward function may reward recommendations (e.g., medical, diet, or physical activity recommendations) that maintain or achieve a normal glucose level.

The ML algorithms used herein may be neural networks. Neural networks can employ multiple layers of operations to predict one or more outputs, e.g., the glucose level of a subject. Neural networks can include one or more hidden layers situated between an input layer and an output layer. The output of each layer can be used as input to another layer, e.g., the next hidden layer or the output layer. Each layer of a neural network can specify one or more transformation operations to be performed on input to the layer. Such transformation operations may be referred to as neurons. The output of a particular neuron can be a weighted sum of the inputs to the neuron, adjusted with a bias and multiplied by an activation function, e.g., a rectified linear unit (ReLU) or a sigmoid function.

Training a neural network can involve providing inputs to the untrained neural network to generate predicted outputs, comparing the predicted outputs to expected outputs, and updating the algorithm's weights and biases to account for the difference between the predicted outputs and the expected outputs. Specifically, a cost function can be used to calculate a difference between the predicted outputs and the expected outputs. By computing the derivative of the cost function with respect to the weights and biases of the network, the weights and biases can be iteratively adjusted over multiple cycles to minimize the cost function. Training may be complete when the predicted outputs satisfy a convergence condition, e.g., a small magnitude of calculated cost as determined by the cost function.

Examples of neural networks include CNNs, recurrent neural networks (RNNs) (e.g., LSTMs), and others. CNNs are neural networks in which neurons in some layers, called convolutional layers, receive pixels from only small portions of the input data set. These small portions may be referred to as the neurons' receptive fields. Each neuron in such a convolutional layer can have the same weights. In this way, the convolutional layer can detect features in any portion of the input data set. CNNS may also have pooling layers that combine the outputs of neuron clusters in convolutional layers and fully-connected layers that are similar to traditional layers in a feed-forward neural network. In some cases, CNNs may be used to detect objects in any portion of an image or video.

RNNs, meanwhile, are neural networks with cyclical connections that can encode dependencies in time-series data, e.g., continuous glucose monitoring data, An RNN can include an input layer that is configured to receive a sequence of time-series inputs. An RNN can also include one or more hidden recurrent layers that maintain a state. At each time step, each hidden recurrent layer can compute an output and a next state for the layer. The next state can depend on the previous state and the current input. The state can be maintained across time steps and can capture dependencies in the input sequence. Such an RNN can be used to encode times-series features of a subject's glucose levels, for example.

One example of an RNN is an LSTM, which can be made of LSTM units. An LSTM unit can be made of a cell, an input gate, an output gate, and a forget gate. The cell can be responsible for keeping track of the dependencies between the elements in the input sequence. The input gate can control the extent to which a new value flows into the cell, the forget gate can control the extent to which a value remains in the cell, and the output gate can control the extent to which the value in the cell is used to compute the output activation of the LSTM unit. The activation function of the LSTM gate can be the logistic function.

The ML algorithms used here may alternatively or additionally be GANs. A GAN can include a generative network and a discriminative network. The generative network can generate candidate simulations while the discriminatory network can evaluate the candidate simulations. The goal of the discriminatory network may be to distinguish between a simulation and a true data distribution, while the goal of the generative network may be to increase the error rate of the discriminatory network. Backpropagation can be applied to both networks so that the generative network produces better simulations, while the discriminative network becomes more skilled at flagging simulations.

The ML algorithms used herein may alternatively or additionally be AEs. AEs can have an encoder that is configured to generate a reduced-dimension representation of an input and a decoder that is the configured to reconstruct the input from the reduced-dimension representation. An AE can be trained by comparing the input to the output and adjusting the weights of the encoder and decoder accordingly. One of the main purposes of AEs is to extract features from data. An AE can be used to detect anomalous data, e.g., data that is different than the training data.

In some embodiments, the ML servers 102 can include reinforcement learning (RL) agents 114 that can operate in response to inputs from data sources 108-0 to -2 to generate suggested actions based on a desired reward function. Such suggested actions can be provided to a user device 110 by operation of a ML or application server (102, 104). Subject responses and behavior as recorded by data sources (108-0 to -2) can be encoded into a latent space with custom variational encoding 116 to model and predict subject responses. In particular embodiments, ML servers 102 can include a personalized blood glucose predictor 118 for predicting subject blood glucose levels, and recommendations generated by RL agents 114 can be actions to help maintain blood glucose levels predetermined-levels.

In other embodiments, the ML servers 102 can include training data generation systems and feature prediction systems. The training data generation systems can use ML processes to generate training data to train the feature prediction system, which can also use ML processes. In some embodiments, the training data generation systems can embed descriptive data to enable a targeted feature to be inferred from such descriptive data. In this disclosure, the word "embed" or "embedding" may refer to a process by which words or phrases, e.g., text-based descriptions of food items, are mapped to vectors of real numbers. The resulting vector space may have a lower dimension than the input (i.e., the words and phrases). As such, embedding may be considered a dimensionality reduction technique. The feature inference system can be trained to infer a target feature, e.g., a glycemic index of the food items, from the embeddings.

The application server 104 can interact with one or more applications running on the subject device 110. In some embodiments, data from data sources (108-0 to -2) can be acquired via one or more applications on the subject device 110 and provided to application server 104. Application server 104 can communicate with subject device 110 according to any suitable secure network protocol. The application server 104 can reside on the same or different physical server as the ML servers 102. The application server 104 can relay subject data from the subject device 110 to the ML server 102.

The data store 106 can store data for system 100. In some embodiments, data store 106 can store data received from data sources (108-0 to -2) (e.g., data from one or more subjects) as well as other data sets acquired by third parties. Data store 106 can also store various other types of data, including configuration data for configuring operations for ML servers 102. The data store 106 can take any suitable form, including one or more network-attached storage systems. In some embodiments, all or a portion of the data store 106 can be integrated with any of the ML or application servers (102, 104).

In some embodiments, data for data sources (108-0 to -2) can be generated by sensors or can be logged data provided by subjects. In FIG. 1, data source 108-0 can correspond to a first type sensor 120-0 (e.g., a heart rate monitor), data source 108-1 can correspond to a second type sensor 120-1 (e.g., a continuous glucose monitor), and data source 108-2 can correspond to logged data 122 provided by a subject. Logged data 122 can include text data or image data (e.g., text data or image data describing or defining nutritional information of a food).

The second type sensor 120-1 and the logged data 122 can be "indirect" data sources in that data from such sources can be used to infer other data. For example, data from the second type sensor 120-1 and the logged data 122 can be used to infer data from the first type sensor 120-0, which may be considered a "direct" data source. In some embodiments, logged data 122 can be processed to infer a biophysical response different from the response(s) that the second type sensor 120-1 records or detects. In some embodiments, both direct and indirect data can be used to train and calibrate biophysical models, however, direct data may not be used in inference operations in such embodiments. Instead, only the indirect data sources may be used during inference. In some embodiments, the first type sensor 120-0 can be a sensor that is more difficult to employ than the second type sensor 120-1. The sensors can record data and transmit the data to the subject device 110 over a local network (e.g., Bluetooth network). The subject device 110 can then transmit the data to one or more servers (e.g., ML servers 102 or application server 104). In addition or alternatively, such sensors can also transmit such data to one or more servers (102, 104) without a subject device (e.g., directly, or via one or more intermediate devices).

In some embodiments, the first type sensor 120-0 can be a continuous glucose monitor (CGM), which can track a glucose level of a subject. The second type sensor 120-1 can be heart rate monitor (HRM) which can track a subject's heart rate. Logged data 122 can be subject nutrition data. In some embodiments, an application running on the subject device 110 can acquire the logged data 122. In some embodiments, the application can capture an image. The image can be, for example, an image of a nutrition label on a pre-packaged food item, an image of a barcode that encodes nutritional information for a particular food, one or more actual food items (e.g., a piece of fruit or a full meal), or the like. ML algorithm on the ML servers 102 can infer nutrition values from the images and, using such nutrition values, infer the glucose response of the subject. The image can be an image of text (e.g., labels 122-1) which can be subject to optical character recognition to generate computer-readable text, and such text can be applied to an inference engine.

While FIG. 1 shows particular data sources for particular biophysical modeling and prediction, embodiments can include any other suitable sensor applications, particularly those applications having a "difficult" sensor (e.g., a direct sensor) that is more difficult, complex, or expensive to implement than one or more other "easy" sensors and/or subject data logging. Data from a difficult sensor can be used to train ML models that can infer a subject response from data from easy sensors and/or subject data logging as inputs.

The subject device 110 can be any suitable device, including but not limited to, a smart phone, personal computer, wearable device, or tablet computing device. The subject device 110 can include one or more applications that can communicate with application server 104 to provide data to, and receive data from, biophysical models residing on ML servers 102. In some embodiments, the subject device 110 can be an intermediary for any of data sources (108-0 to -2). The communication network 112 can be any suitable network, including a local area network, wide area network, or the internet, for example.

Figure 2:
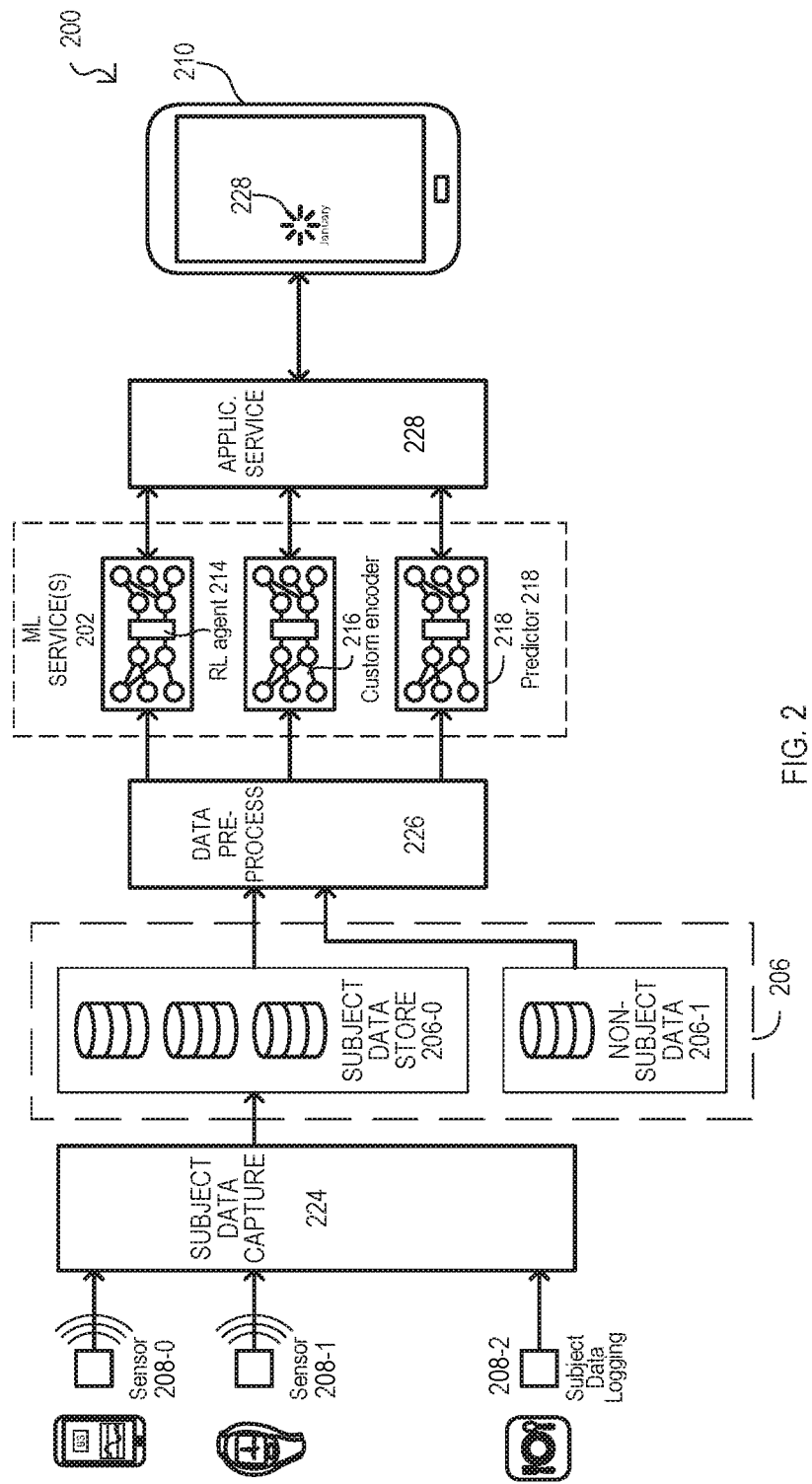
FIG. 2 is a block diagram of another system according to an embodiment.

Referring to FIG. 2, a system 200 according to another embodiment is shown in a block diagram. The system 200 can include data source inputs 208-0, 208-1, 208-2, a subject data capture portion 224, a storage portion 206, a data pre-processing portion 226, a ML services portion 202, and an application services portion 204. Data source inputs (208-0, 208-1, 208-2) can provide data for learning operations in ML services portion 202 that create biophysical models for a subject. Any or all of data source inputs (208-0, 208-1, 208-2) can provide data for inference operations executed on models resident in ML services portion 204. In very particular embodiments, data source inputs (208-0, 208-1, 208-2) can include any of the sensors and/or subject data logging described herein or equivalents.

Data store portion 206 can include subject data storage 206-0 as well as non-subject data storage 206-1. Subject data storage 206-0 can be data for particular subjects for which ML models have been created or are being created. Non-subject data storage 206-1 can include data derived from other sources that can be used for other purposes such as training and creating models. Such data can include, but is not limited to, data from non-subjects, such as participants in third-party studies.

A data pre-processing portion 226 can process data from data store portion 206 Data pre-processing portion 226 can include instructions executable by a processor to place data into particular formats for processing by ML services portion 202.

ML services portion 202 can include computing systems configured to create ML models and architectures through supervised and/or unsupervised learning with any of data source inputs 208-0, 208-1, 208-2. In addition, ML services portion 202 can include ML models and/or architectures that generate inference results based on any of data source inputs 208-0, 208-1, 208-2. ML services portion 202 can include single computing devices that include ANNs of the various architectures described herein, as well as ANNs distributed over networks. As in the case of FIG. 1, ML services portion 202 can include AEs, GANs, LSTMs, CNNs, RL algorithms, and any other suitable ANN or other statistical learning agent, and related architectures. In some embodiments, ML services portion 202 can include reinforcement learning agents 214, custom variable encoders 216, and one or more networks configured to predict a reaction 218 customized to a user based on any of data source inputs (208-0 to -2).

Application services 204 can access models or other networks resident in ML services portion 202 to provide data for one or more subject applications 228 resident on a subject device 210. Applications 228 can utilize model/network outputs to provide information to subjects. In some embodiments, application services portion 228 can provide recommended actions for subjects based on subject responses predicted by models/networks in ML services portion 202. In some embodiments, application services portion 228 can recommend subject actions based on predicted glucose levels of subjects and subjects recorded activities. The recommended actions can be diet-related, physical activity-related, or the like. While application services portion 204 can service applications 228 running on subject devices 110, in other embodiments application services 204 can execute applications and provide (e.g., push) data to other services (e.g., email, text, social network, etc.).

Referring still to FIG. 2, example operations performed by the system 200 will now be described. The sensors 208 can acquire two or more different types of data. In some cases, one type of data may be an input feature or attribute and another type of data may be a target output (e.g., an output to be predicted by an ML algorithm). Both types of data may be associated with text-based descriptions. The ML services portion 202 can generate embeddings of the text-based descriptions using an embedding function. Such embeddings can be used to infer the input features or attributes or the target output. The inferred values can be used to train the system 200 to predict the target output from the input feature or attribute.

For example, the embedding function can generate embeddings of descriptions of food items. Thereafter, the embeddings and corresponding glycemic values for such food items (which serve as labels) can be used to train the inference system (e.g., a supervised machine learning algorithm such as an ANN) to predict glycemic values using only standard nutrition data of the food items, which may be more readily available than glycemic values.

While embodiments can include numerous systems and methods for modeling and predicting subject responses, some embodiments can include systems and methods for making personalized recommendations for a subject, based on predicted reactions of a subject.

Figure 3:
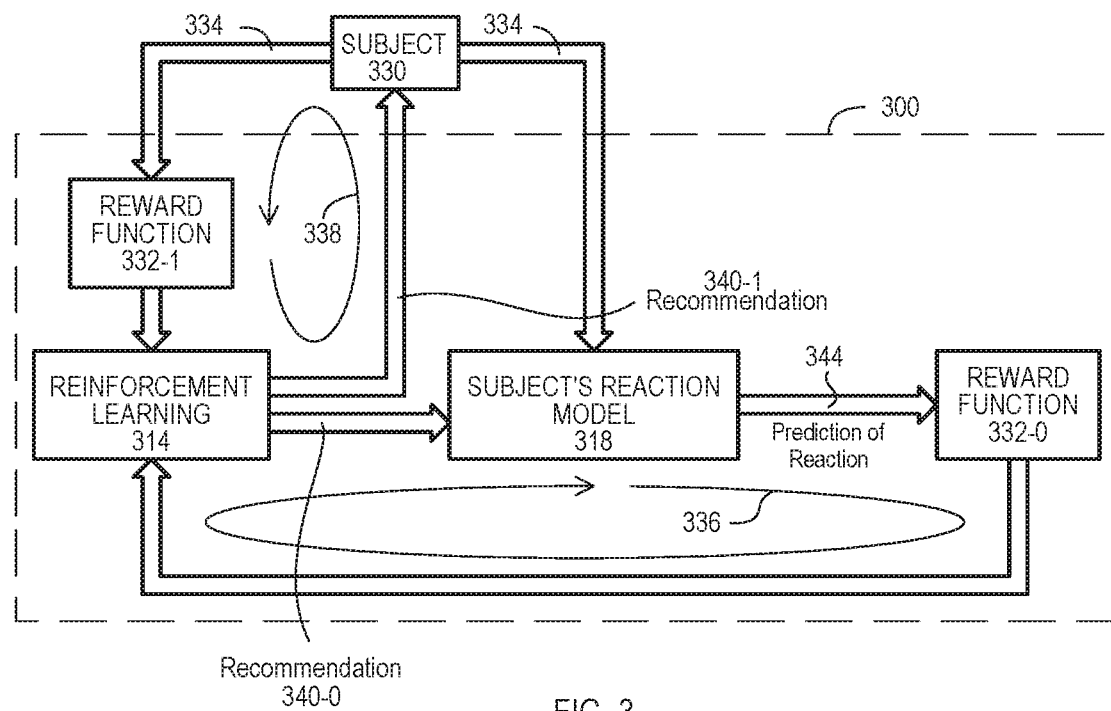
FIG. 3 is a block diagram of a recommendation system according to an embodiment.

FIG. 3 is a block diagram of a recommendation system 300, according to an embodiment. The system 300 can generate recommendations for a subject 330. The system 300 can include a subject reaction model 318, reward functions 332-0/1, and an RL section 314. The subject reaction model 318 can be a personalized model for the subject 330. The system 300 can include a high frequency loop 336 and a low frequency loop 338.

The high frequency loop 336 can include the RL section 314, the subject reaction model 318, and the reward function 332-0. The RL section 314 can be an ML model. For example, the RL section 314 can be a neural network. The RL section 314 can initially be configured with random weights or parameters. The RL section 314 can be configured to generate a recommendation 340-0 for a subject 330. The recommendation 340-0 can be a diet, physical activity, sleep, hydration, or stress release recommendation, for example. Based on recommendation 340-0 and subject reaction 334, subject reaction model 318 can generate a predicted subject reaction 344. The predicted subject reaction 344 can be the subject's predicted reaction to the recommendation 340-0. The reward function 332-0 can process the predicted subject reaction 340-0 to generate a reward for the RL section 314. The reward function 332-0 can generate a positive reward if the predicted subject reaction 340-0 is beneficial to a particular health measurement of interest (e.g., the subject's glucose level) and a negative reward if the predicted subject reaction is detrimental to the health measurement of interest. The weights or parameters of the RL section 314 can be adjusted to account for the award. In general, the RL section 314 may iteratively adjust its weights or parameters to maximize the reward it receives. Such actions can continue until high frequency loop 336 arrives at a particular subject recommendation 340-1 (for example an optimal recommendation) which can be issued to subject 330. Subject recommendation 340-1 can be generated according to various criteria. For example, a reward function value, number of iterations, or amount of time passed, to name only a few.

The low frequency loop 338 can use a subject's actual response to recommendations to generate new recommendations. The low frequency loop 338 can include recommendation 340-1 (arrived at by RL section 314 according to predetermined criteria), reward function 332-1, and RL section 314. The subject actual response 334 to the low frequency (e.g., optimal) recommendation 334-1 can be evaluated by a reward function 332-1, to generate inputs to RL section 314. RL section 314 can seek to maximize a reward to generate a recommendation 340-0 (which may be included in high frequency loop 336).

While recommendation systems as described herein can be implemented in various applications, some embodiments can model a subject's biophysical response to provide recommendations for achieving a goal, such as improved health. Such an embodiment is shown in FIG. 4.

Figure 4A:
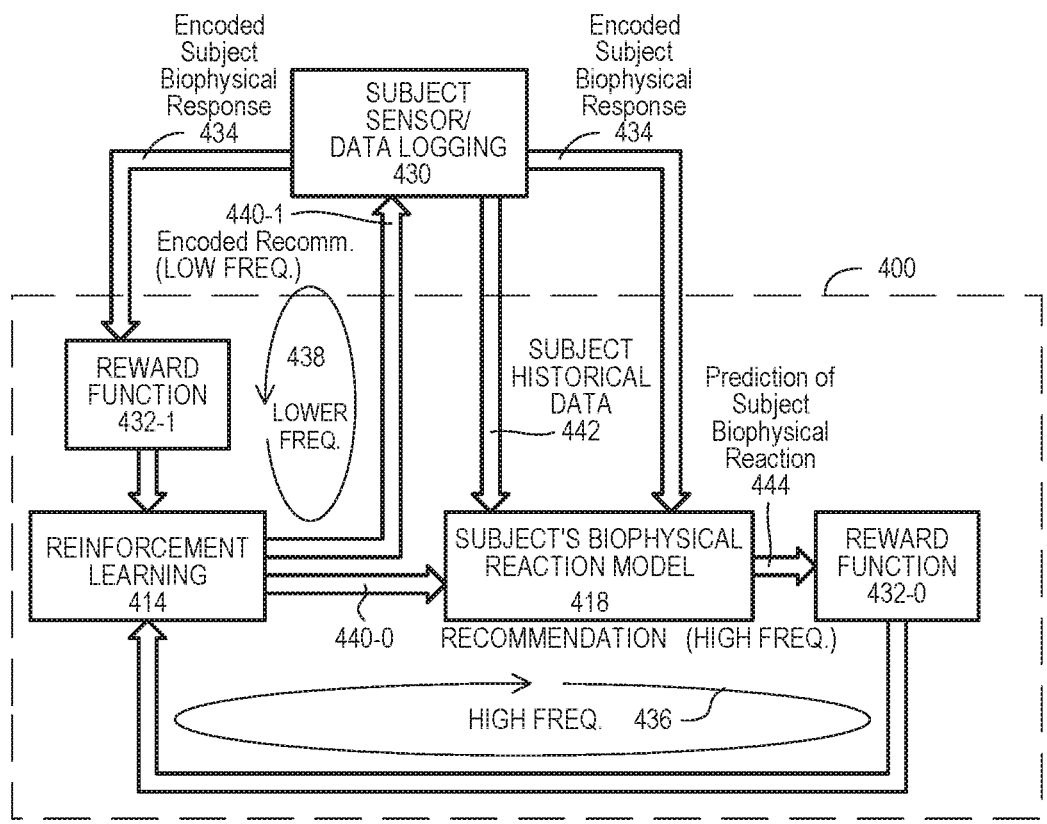
FIG. 4A is a block diagram of a recommendation system according to another embodiment.

FIG. 4A shows a recommendation system 400 according to another embodiment. The recommendation system 400 can be an implementation of the system 300 of FIG. 3. Recommendation system 400 can provide health related recommendations for a subject based on biophysical responses. Biophysical responses can include any responses described herein (e.g., glucose response, insulin, weight). In some embodiments, recommendations can include physical activities and/or nutrition suggestions based on biophysical sensor readings and/or other data logged by a subject. In particular embodiments, an encoded biophysical response 434 can include heart rate monitor data and logged food data encoded into a latent space.

In FIG. 4A, subject sensor and/or data logging 430 can provide encoded subject responses 434 and historical data for a subject 442 to a system 400. In response, a system 400 can provide an encoded recommendation 440-1.

The system 400 can have a high frequency loop 436. The high frequency loop 436 can have a RL section 414, a subject biophysical reaction model 418, and a reward function 432-0. The RL section 414 can generate a recommendation 440-0. The recommendation 440-0 can be a recommendation to eat a particular food, participate in a physical activity, or the like. Subject biophysical reaction mode 418 can receive the recommendation 440-0, as well as subject historical data 442 and encoded subject biophysical responses 434 for a subject. In response, subject biophysical reaction mode 418 can generate a predicted subject reaction 444. The predicted subject reaction 444 can be evaluated by reward function 432-0. Reward function 432-0 can base its evaluation on a health-related outcome. In some embodiments, the health-related outcome can be a function of the blood glucose level of a subject. The resulting output of the reward function 432-0 output can be provided to RL section 414. The weights of the RL section 414 can be adjusted based on the output of the reward functions 432-0. High frequency loop 436 can continue until a predetermined point at which RL section 414 can issue a current, low frequency recommendation 438 to a subject. Such a predetermined point can be based on some quantitative value of reward function (e.g., convergence, optimality), or number of iterations, or time-based periodicity, or some combination thereof, to name a few examples.

The low frequency loop 438 can include reward function 432-1 and RL section 414. Encoded subject biophysical responses 434 can be applied to reward function 432-1. As in the case of reward function 432-0, reward function 432-1 can evaluate responses 434 on a health-related outcome. In some embodiments, reward function 432-1 can have the same or similar reward states as reward function 432-0. The resulting output of reward function 432-0 can be provided to RL section 414. As noted above, RL section 414 can receive more frequent reward function evaluations from high frequency loop 436.

Figure 4B:
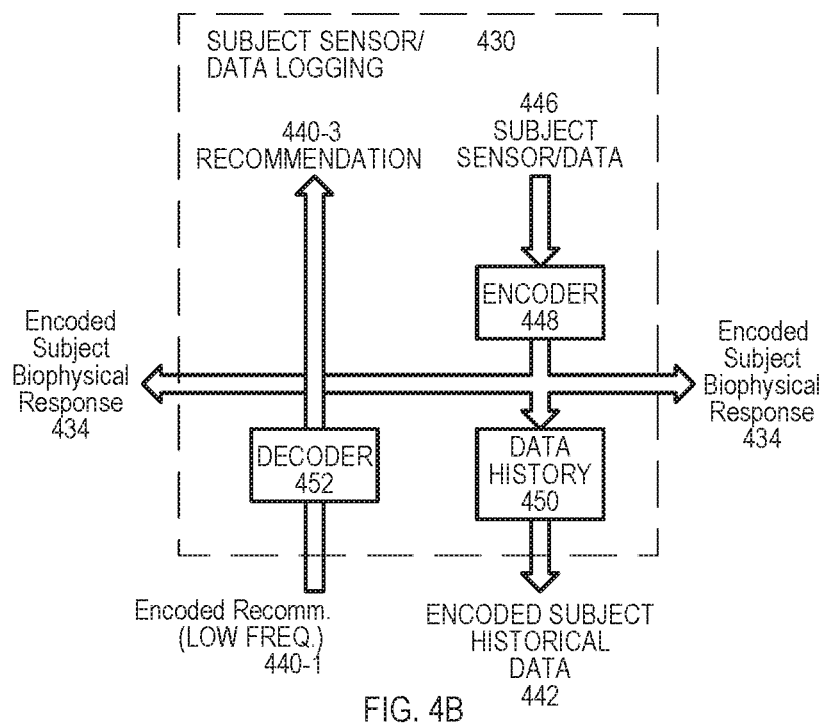
FIG. 4B is a block diagram of subject data input and output that can be used like that of FIG. 4A.

FIG. 4B is a diagram showing subject sensor and/or data logging 430 according to an embodiment and can be one implementation of that shown in FIG. 4A. Subject sensor and other data 446 can be received from any suitable source as described herein and equivalents. Such data 446 can be received in processed form, including encoded form, however in FIG. 4B data 446 is received in unencoded form.

Subject sensor and other data 430 can be encoded by an encoder 448 to generate encoded subject biophysical response 434 for use by a reward function and/or subject biophysical reaction model. Encoded data 430 can also be stored or further encoded in data history 450, which can be accessed to acquire subject historical data 442. In the embodiment shown, low frequency encoded recommendations 440-1, which can be received from an RL section, can be decoded by a decoder 452 to generate unencoded recommendations 440-3 that can be presented for a subject.

Figure 4C:
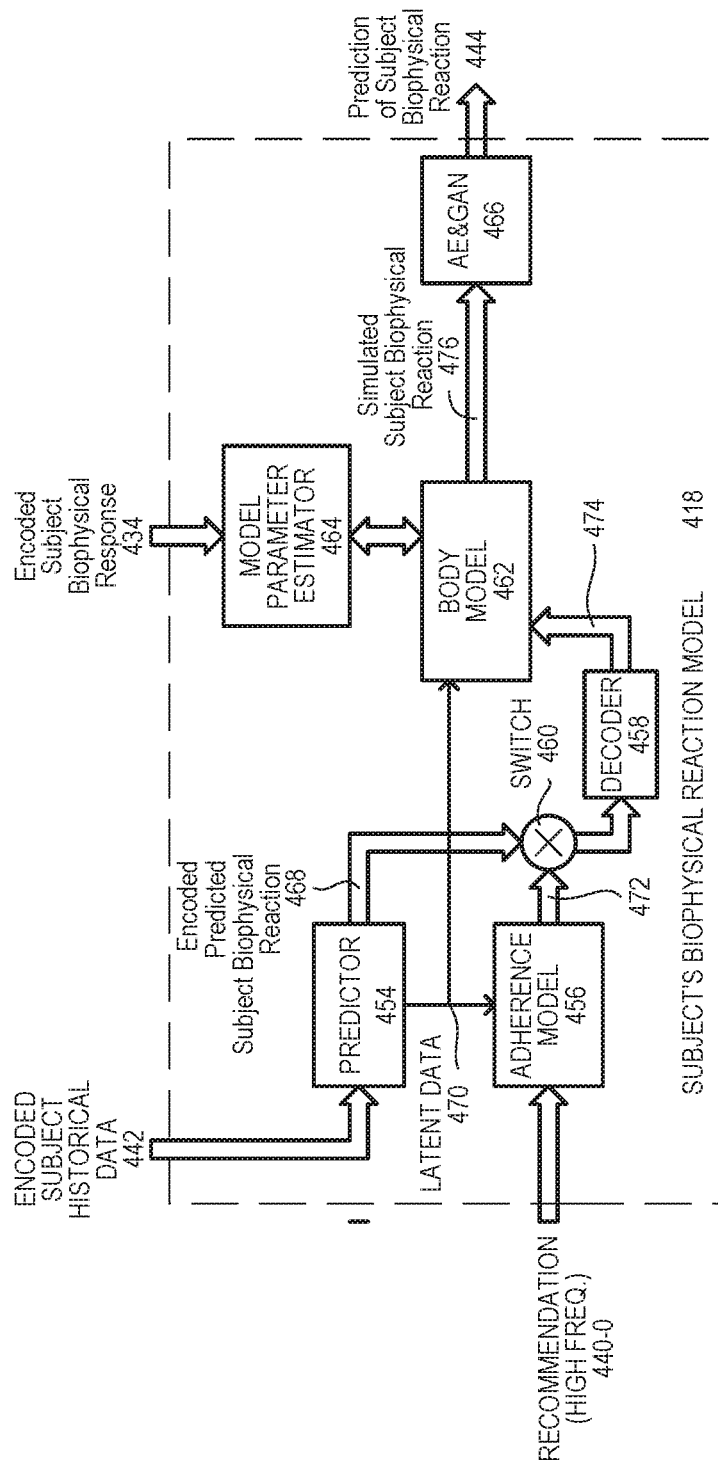
FIG. 4C is a block diagram biophysical reaction model according to an embodiment.

FIG. 4C shows a subject biophysical reaction model 418 according to an embodiment. The subject biophysical reaction model 418 can include a predictor 454, adherence model 456, decoder 458, switch function 460, body model 462, parameter estimator 464, and an AE and GAN 466. Using encoded subject historical data 442, the predictor 454 can generate a predicted subject reaction 468 (in encoded form). The predictor 454 can also provide latent data 470 regarding a subject's actions to body model 462 and adherence model 456.

In response to a high frequency recommendation 440-0, adherence model 456 can provide an adherence output 472, that indicates to what extent a subject's actions follow the recommendation 440-0 (e.g. if the subject eats a recommended food or participates in a recommended physical activity). Adherence output 472 can be in encoded form.

A switch function 460 can selectively apply a predicted subject reaction 468 or adherence output 472, when a recommendation is simulated, as an input to a body model 462. In the embodiment shown, a body model 462 can operate in response to unencoded data and so a decoder 458 can translate inputs from switch function 460 from a latent space into unencoded reaction data 474.

Unencoded reaction data 474 (which can be derived from a predicted subject reaction or adherence model evaluation) can be applied to a body model 462 to generate a simulated subject biophysical reaction 476. The body model can be a personalized learned model for a specific subject. During inference, inputs (e.g., food consumption and heart rate) of the user and latent states of the user can be used predict the physical observables of the user (e.g., glucose values). The simulated subject biophysical reaction 476 can be applied to an AE and GAN 466 to produce a more enhanced predicted subject biophysical reaction 444. The AE and GAN 466 can receive the output of the body model 462 which can be a simulated glucose curve and modify the simulated glucose curve to ensure it resembles real glucose values. In other words, the AE and GAN 466 can add deep learning on top of simulated observables to assure that the simulated and real glucose values will not be distinguishable.

Referring still to FIG. 4C, while predicted subject biophysical reactions 476 are generated as described above, a body model 462 can be updated in response to a subject actual biophysical response represented by encoded subject biophysical response 434. In the embodiment shown, in response to a subject's biophysical response 434, a model parameter estimator 464 can update parameters within body model 462 to seek convergence between simulated subject biophysical reactions 476 and actual subject biophysical response (e.g., 434). For example, the parameters of the body model may be updated via a supervised learning process, during which the encoded subject biophysical responses 434 are used as training data labels.

Figure 4D:
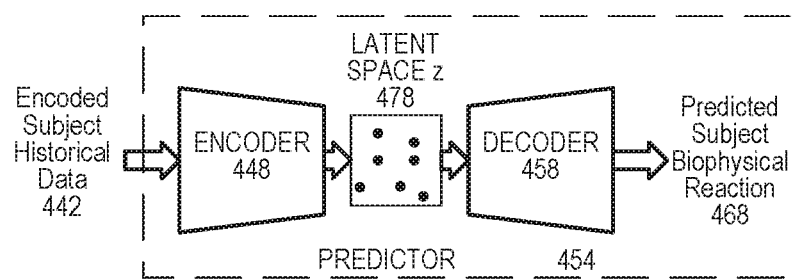
FIG. 4D is a block diagram of a predictor that can be included in a system like of FIG. 4A.

FIG. 4D shows a predictor 454 that can be included in embodiments, including that of FIG. 4C. Predictor 454 can include an encoder 448 and decoder 458. In some embodiments, encoder 448 can be an autoencoder. In particular embodiments, encoder 448 can be a custom variational encoder as described herein, or an equivalent. Encoder 448 can be trained to predict subject reactions from subject historical data by mapping historical data into latent space 478. In response to subject historical data 442, encoder 448 can infer predicted subject reactions. Such reactions can be decoded by decoder 458 to generate a predicted subject reaction 468. In some embodiments, encoder 448 can be trained to map inputs that satisfy the preconditions of (1) minimizing reconstruction losses when decoded by decoder 458 and (2) preserving predetermined minimum distance metrics in the latent space 478.

Figure 4E:
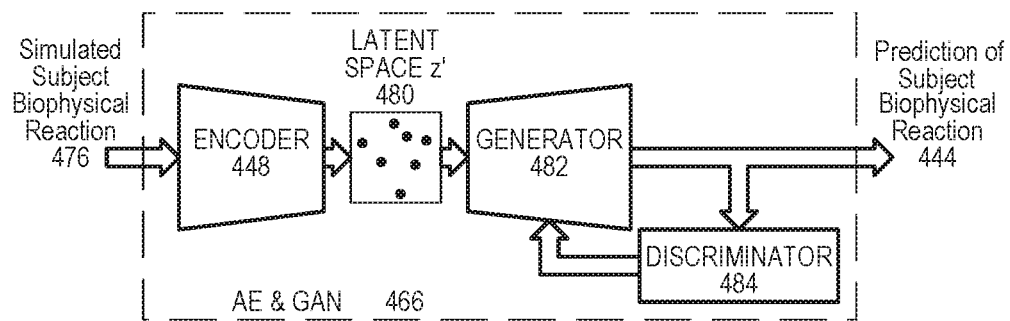
FIG. 4E is a block diagram of an autoencoder (AE) and generative adversarial network (GAN) that can be included in embodiments.
Figure 5:
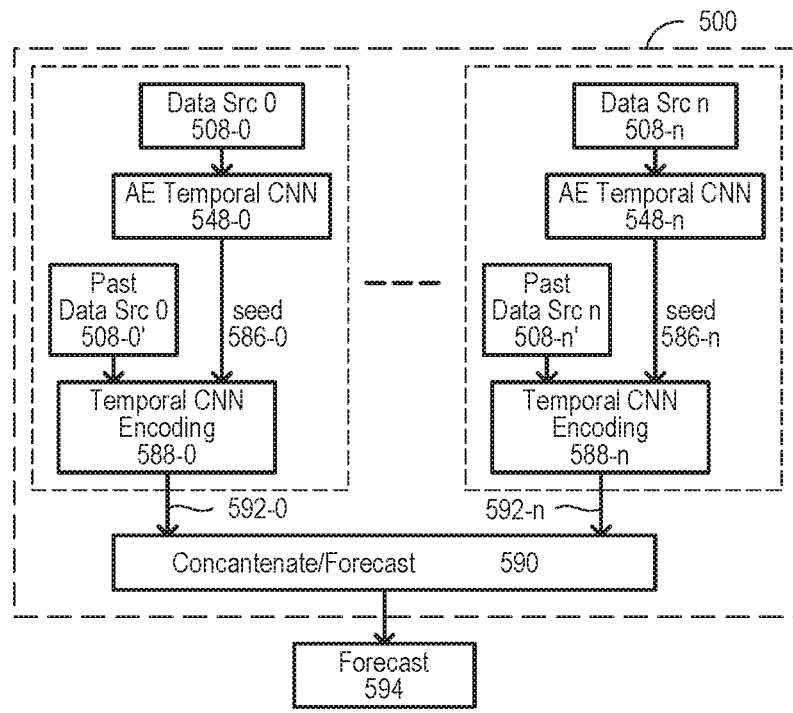
FIG. 5 is a block diagram of data prediction system according to an embodiment.

FIG. 4E shows an AE and GAN 466 that can be included in embodiments, including that of FIG. 4C. AE and GAN 466 can include an encoder 448, a generator 482, and discriminator 484. Encoder 448 can map simulated subject biophysical reactions 476 into a latent space 480. Outputs from encoder 448 can be applied to generator 482. Generator 482, in combination with discriminator 484, can form a GAN. Generator 482 can output predicted subject biophysical reactions 444. Discriminator 484 can be trained with actual biophysical reactions and provide feedback to generator 482 so that that predicted biophysical reactions 444 may more closely follow those of actual subjects. 10148j Embodiments can also include systems and methods for predicting data series from past heterogenous data sources. FIG. 5 is a block diagram of a data prediction system and method 500 according to an embodiment. The data prediction system 500 can include various different data sources 508-0 to 508-n (e.g., food, heart rate, sleep, calendar, etc.), AE temporal convolutional neural networks (CNNs) 548-0 to 548-n, corresponding past data sources 508-0' to 508-n', temporal CNN encoders 588-0 to 588-n, and a concatenate/forecast section 590. Any CNN can be replaced by an RNN type network, such as an LSTM as but one example.

Each of the AE temporal CNNs (548-0 to 548-n) can receive and be trained with data from a different data source (508-0 to 508-n). In response to such training, AE temporal CNNs (548-0 to 548-n) can provide seed values, which are a set of priors and initial states, (586-0 to 586-n) to the temporal CNN encoding (588-0 to 588-n). Seed values (586-0 to 586-n) can configure their corresponding temporal CNN encoding (588-0 to 588-n) which can have a same encoding architecture as AE temporal CNNs (548-0 to 548-n). Temporal CNN encoding (588-0 to 588-n) can then receive past data source values (508-0' to 508-n'), which are of the same type used to generate the seed values (586-0 to

596-n). Such past data source values (508-0' to 508-n') can then be encoded to generate encoded values 592-0 to 592-n.

Encoded values 592-0 to 592-n, can be applied to an ANN within concatenate/forecast section 590, which can generate predicted values as data forecast 594. Forecast 594 can represent predictions for any or all of values represented by data sources 508-0 to -n.

Figure 6:
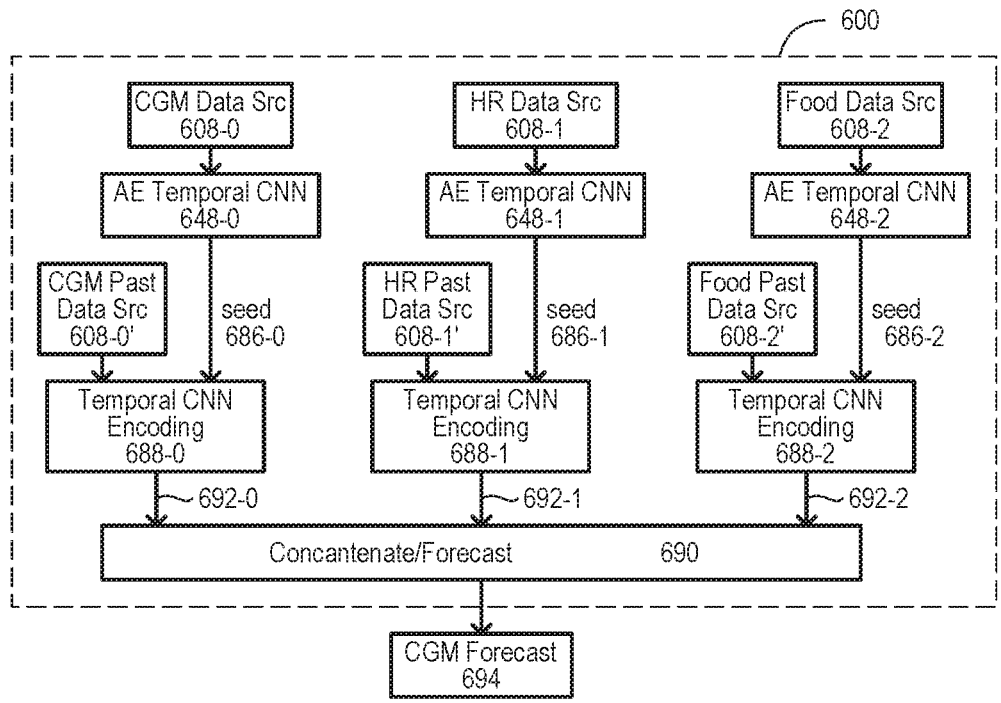
FIG. 6 is a block diagram of a biophysical prediction system according to an embodiment.

FIG. 6 shows a block diagram of a system 600 for predicting one type of biophysical response from multiple, different biophysical responses. System 600 can be one particular implementation of that shown in FIG. 5. In the particular embodiment shown, system 600 can predict a future glucose level from heterogenous data sources of a CGM, HRM and food logging.

The system 600 can receive data from a CGM source 608-0, an HR source 608-1 and a food logging source 608-2. Data from the CGM source 608-0 can be received by an AE temporal CNN 648-0, which can generate seed values 686-0, which are a set of priors and initial states. Data from the HR source 608-1 can be received by an AE temporal CNN 648-1, which can generate seed values 686-1. Data from the food logging source 608-2 can be received by an AE temporal CNN 648-2, which can generate seed values 686-2.

A temporal CNN encoding 688-0 can be seeded with seed values 686-0 and encode past data from a CGM source 608-0' to generate encoded CGM values 692-0. Similarly, temporal CNN encoding 688-1 can be seeded with seed values 686-1 and encode past data from a HR source 608-1' to generate encoded HR values 692-1, and temporal CNN encoding 688-2 can be seeded with seed values 686-2 and encode past data from food logging 608-2' to generate encoded food logging values 692-2.

Encoded CGM values 692-0, encoded HR values 692-1 and encoded food logging values 692-2 can be applied to concatenate/forecast section 690, which can be configured to generate predicted CGM data (CGM forecast 694). Concatenate/forecast section 690 can be any suitable architecture configured and/or trained to forecast CGM values from the encoded CGM, HR and food logging values (692-0 to -2). For example, the concatenate/forecast section 690 can have a machine learning layer and an output layer (e.g., a softmax layer).

While embodiments can include systems and methods for generating recommendations or forecasting responses based on sensor data, other embodiments can include systems and methods that can classify human behavior into discrete actions. Such discrete actions can be used to arrive at recommendations or other operations to effect subject behavior.

Figure 7:
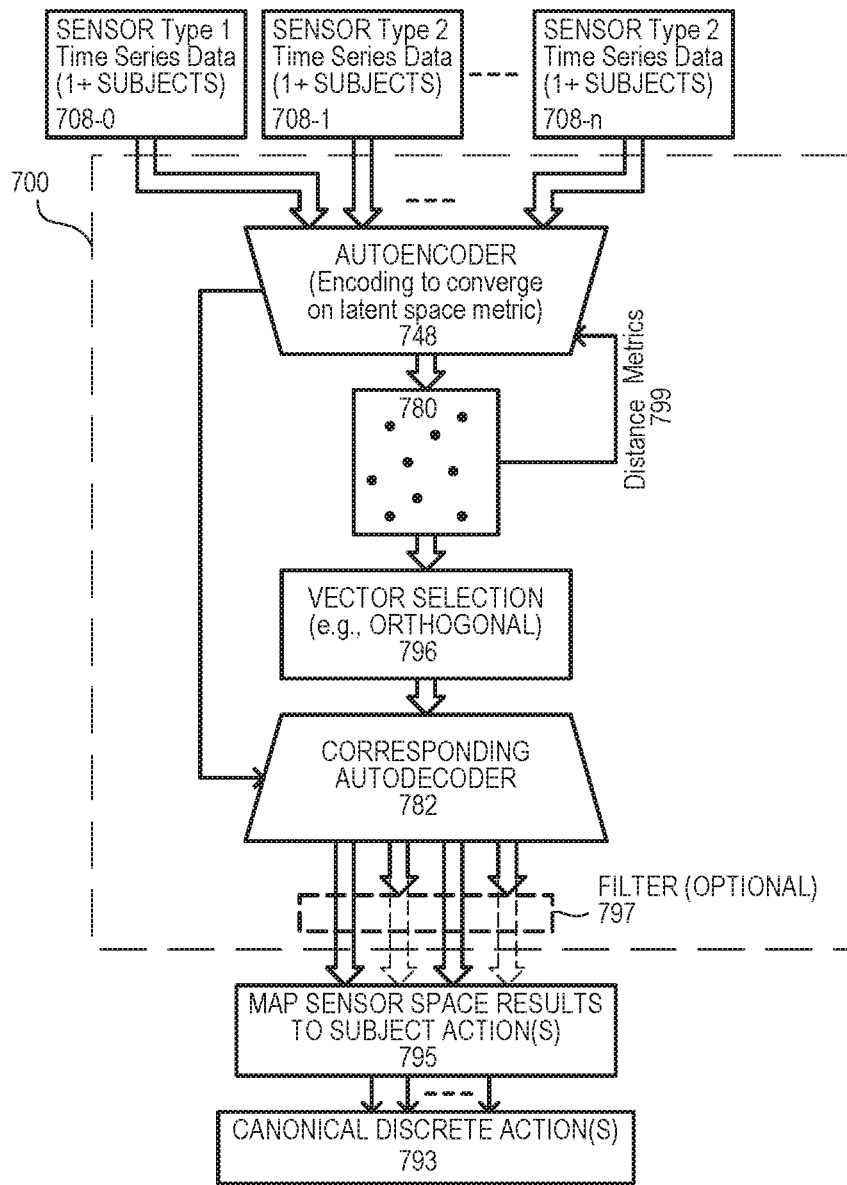
FIG. 7 is a block diagram of a system and method for encoding time series data to infer canonical actions of a subject.

FIG. 7 is a block diagram of a system 700 for classifying behavior of a subject (e.g., eating, physical, activity, sleeping, etc.) according to an embodiment. The system 700 can include an encoder 748, an orthogonal signal selection 796, a decoder 782, a mapping section 795, an optionally, a personalization filter 793.

The encoder 748 can receive time series data from different data sources shown as 708-0 to 708-n. The data sources (708-0 to -n) can each provide data from one or more subjects. According to some embodiments, the data sources (708-0 to -n) can include sensors that can provide data for physiological responses of a subject or subjects. Data sources (708-0 to -n) can include but are not limited to a glucose monitors (e.g., CGM), HR monitors, food consumption data (e.g., food logging), sleep state, accelerometer readings, calendar data, IR geographic data (e.g., GPS). While time series data can be encoded in any suitable timeframe for the desired encoding result, in some embodiments, time series data can be encoded in increments of no more than about an hour, no more than about 30 minutes, or no more than about 15 minutes. In some cases, the increments can be longer than an hour.

The encoder 748 can be trained to maintain a predetermined metric distance in a resulting latent space 780. This can include implementing distance metrics 799 that can seek to cluster values in latent space, while maintaining separation between clusters. In some embodiments, the encoder 748 can be a temporal CNN variational AE. Time series data from sensors (708-0 to -n) can take any suitable form, but in some embodiments can include consecutive 15-minute sections of sensor data.

Orthogonal vector selection 796 can select a set of orthogonal vectors suitable to the particular type of encoder 748. Vectors can be selected based on a resulting latent space 780. Decoder 782 can include a decoding ANN or other network corresponding to the encoder 748. Decoder 782 can receive inputs from orthogonal signal selection 796 and generate an output that represents a set of statistically common behaviors. Optionally, such behaviors can be filtered by a personalization filter 797. For example, common behaviors can be selected or eliminated based on relevance to the subject(s).

Mapping section 795 can map the sensor space results to approximate actions of subject(s). Such actions can present "canonical" discrete actions 793 for use in recommendations, control suggestions, etc.

While embodiments can include systems and methods for predicting a subject response with subject models, embodiments can also include methods and systems for monitoring and diagnosing such models. A system can be in communication with various models that infer subject responses. The results of such models can be compared with actual subject responses that serve as reference values.

Figure 8:
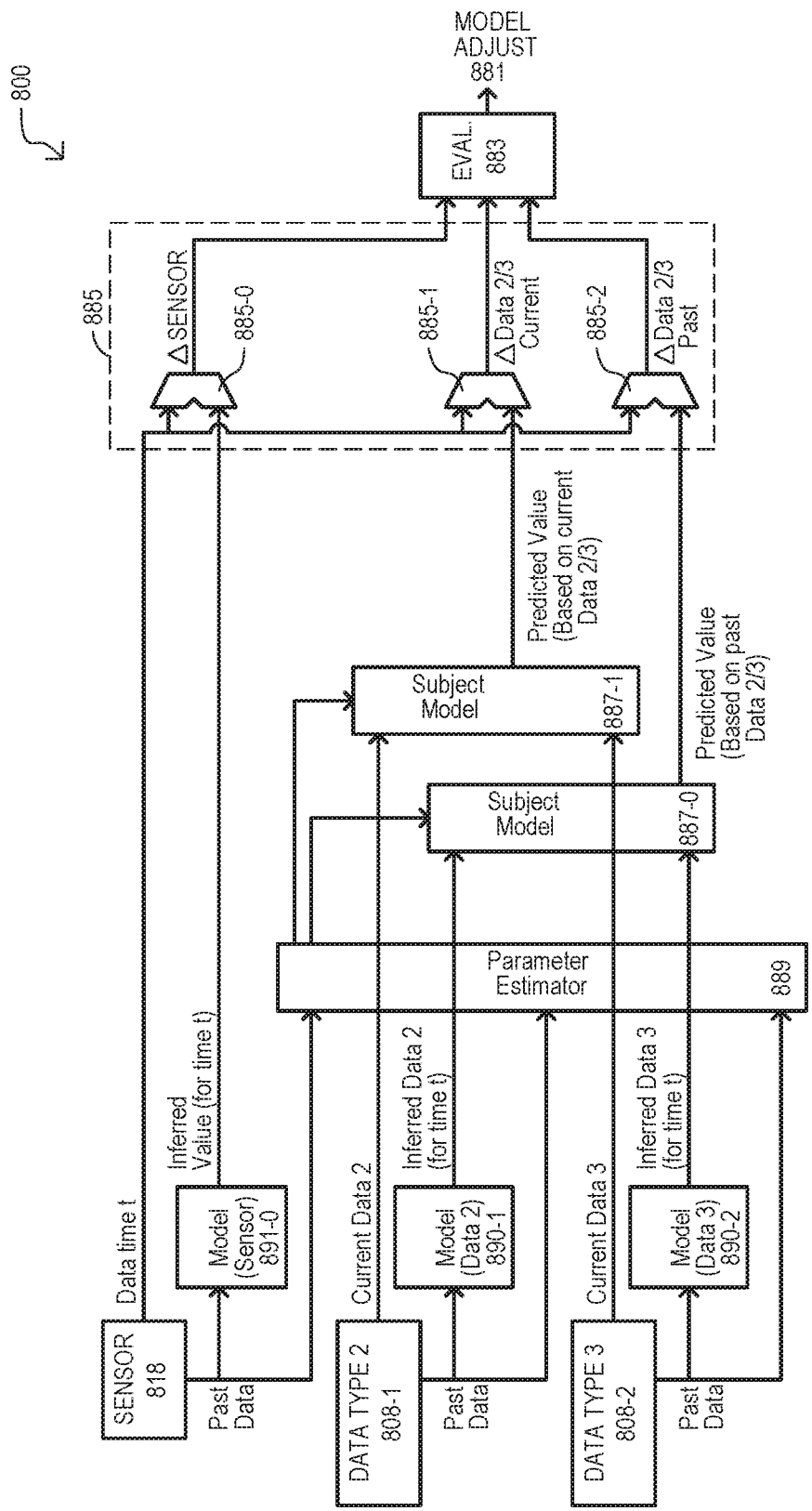
FIG. 8 is block diagram of an evaluation system according to an embodiment.

FIG. 8 shows an evaluation system 800 according to an embodiment. The system 800 can implement a self-consistent model to evaluate and train a complex model that consists of various machine-learning blocks. The accuracy of a complex model is affected by each one of the machine-learning blocks in it. To evaluate each one of these blocks, the system 800 can compare the outputs and introduce the main source of error and then the adjust the models can update the lossy ones. The system 800 can include a sensor 818 (which can serve as data source), other data sources 808-1 and 808-2, data source models (891-0/1/2), a parameter estimator 889, subject models 887-0/1, a compare section 885, and an evaluation section 883. Data sources can include at least one primary, or direct data source (sensor 818) and one or more secondary data sources (in the example shown, 808-1 and 808-2). The primary data source 818 can provide data for a value that is inferred from secondary data sources 808-1/808-2 and can serve as a reference value. Data sources (818, 808-1, 808-2) can provide both current data as well as past data. In the embodiment shown, the primary data source 818 can be a sensor. In some embodiments, the primary data source 818 can be a sensor that makes a biophysical measurement of a subject.

Data source models (891-0/1/2) can include any suitable predictive statistical learning agent that can predict future data values based on past data values. Thus, data source models 891-0, 891-1, 891-2 generate inferred data values from past data values of their corresponding data sources 818, 808-1, 808-2, respectively.

Parameter estimator 889 can receive past data values from secondary data sources 808-1, 808-2, and be in communication with subject models 887-0 and 887-1. Based on received data values, parameter estimator 889 can update parameters of the subject models 887-0 and 887-1. That is, the parameter estimator 889 can be used to train the subject models 887-0, 887-1.

The subject model 887-0 can infer a predicted value of a biophysical response based on predicted data values from data source models 891-1/2 (i.e., predicted secondary data values). The subject model 887-1 can infer a predicted value (e.g., a biophysical response such as a glucose response) based on actual data values from data sources 808-1, 808-2 (i.e., actual secondary data values). It is understood that the values predicted by subject models 887-0/1 can be for the same features measured by primary data source 818.

The compare section 885 can make comparisons with a reference value provided by primary data source 818. In the embodiment shown, compare section 885 can include a number of compare operations 885-0 to -2. Compare operation 885-0 can compare reference values (from sensor 818) with predicted values from data source mode 881-0. Compare operation 885-1 can compare the reference values with predicted value from first subject model 887-0. Compare operation 885-1 can compare reference values with a predicted value from second subject model 887-1.

Evaluation section 883 can receive the various comparisons from compare section 885, and in response, update any of the models and/or parameter estimator 889 accordingly, with model adjustments 881.

Figure 9:
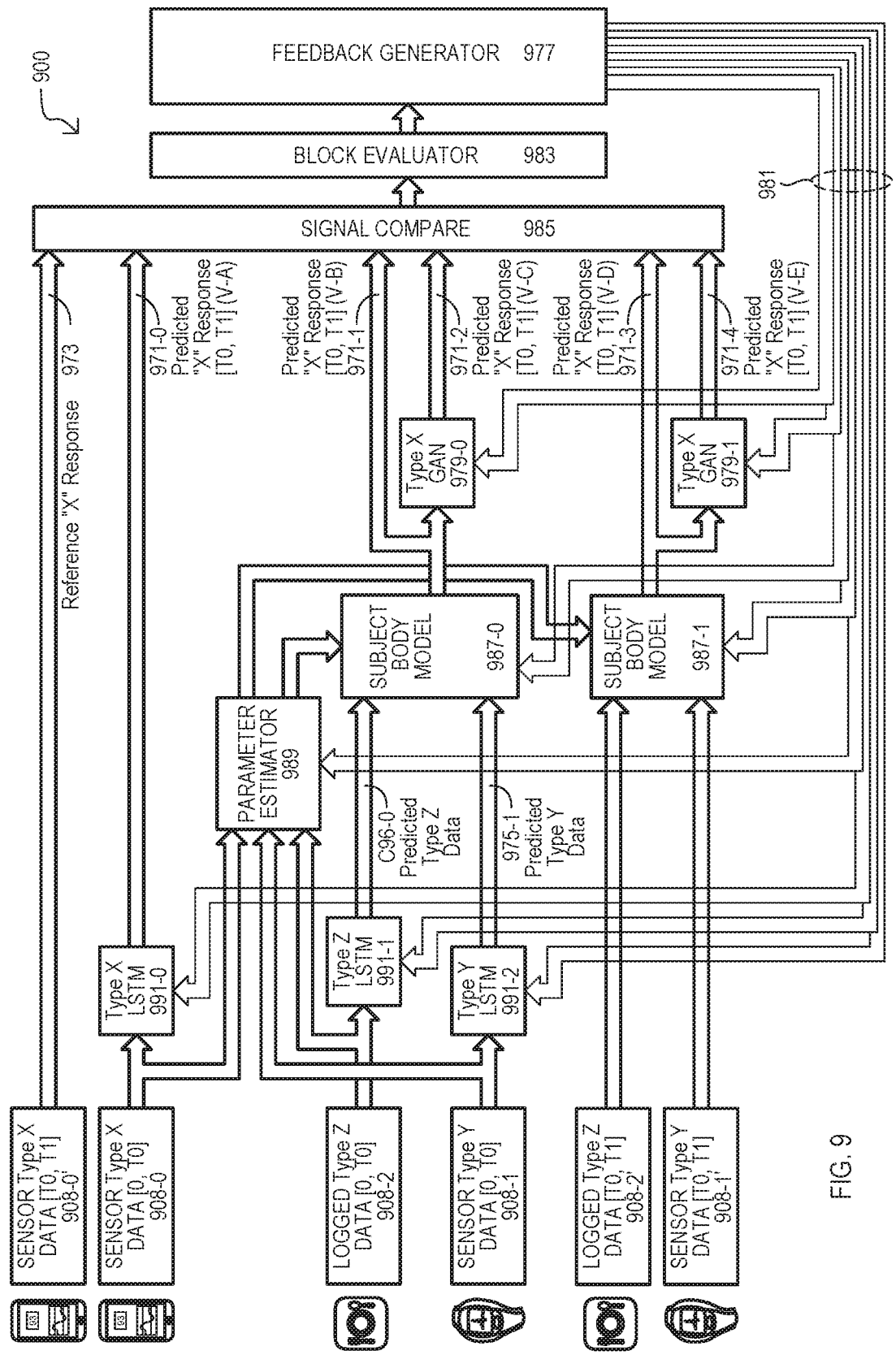
FIG. 9 is block diagram of an evaluation system according to another embodiment.

FIG. 9 shows an evaluation system 900 according to another embodiment. The system 900 can be one particular implementation of that shown in FIG. 8. System 900 includes data sources 908-0 to 908-2', data source LSTMs 991-0/1/2, parameter estimator 989, subject body models 987-0/1, GANs 979-0/1, signal compare section 985, block evaluator 983, and feedback generator 977.

Data sources (908-0 to 908-2') can include data for signals of three different types, type X, type Y and type Z. The type X signal can be a response to be simulated by a system. Type Y and type Z signals can be used to infer predicted type X signals. In the embodiment shown, data sources (908-0 to 908-2') can provide signals for different time periods (T0, T1) and (0, T0), with time period (T0, T1) following and, in some embodiments, overlapping with time period (0, T0). Data source 908-0' can be a first type sensor that provides a type X signal for a time period T0, T1. Data source 908-0 can be sensor data for a type X signal for a time period 0, T0. Data source 908-1' can be a second type sensor that provides a type Y signal for time period T0, T1. Data source 908-1 can be sensor data for a type Y signal for time period 0, T0. Data source 908-2' can be data logged by a subject that provides a type Z signal for a time period T0, T1. Data source 908-2 can logged data for a type Z signal for a time period 0, T0.

In some embodiments, data sources 908-0/0' can provide data generated by a CGM of a subject, data sources 908-1/1' can be data generated by an HRM of the subject, and data sources 908-2/2' can logged food data from the subject.

LSTMs 991-0/1/2 can generate predicted type X, type Y and type Z signals, respectively, for time period T0, T1, from actual signal data from a previous time period 0, T0.

Subject body models 987-0/1 can be ANN or other ML models of a subject biophysical response that generates a predicted type X signal from type Y and type Z signals. The first subject body model 987-0 can generate a predicted type X signal for a time period (T0, T1) from predicted type Y signals 975-0 and predicted type Z signals 975-1 provided from LSTMs 991-1 and -2, respectively. The second subject body model 987-1, which can be a copy of the first subject body model 987-0, can generate a predicted type X signal for time (T0, T1) from type Y and type Z signals for time period (T0, T1). Parameter estimator 989 can update parameters of subject body models 987-0/1 based on Type X, Y and Z signals for time period (0, T0). In other words, subject body model 987-0 can predict the type X signal based on predicted type Y and type Z signals, while subject model 987-1 can predict the type X signal based on actual type Y and type Z signals.

GANs 979-0/1 can take predicted type X signals provided by subject body models 987-0/1 and adjust them to take a more realistic form. For example, GANs (979-0/1) can have been trained with actual type X signals.

A signal compare portion 985 can compare a reference type X signal 973 from data source 908-0', to various outputs provided from system 900 to determine an accuracy of such blocks. As but a few examples, compare portion 985 can compare reference signal 973 to the predicted type X signal 971-0 from LSTM 991-0 to determine the accuracy of LSTM 991-0. Reference signal 973 can be compared to the predicted type X signal 971-1 from subject body model 987-0 to determine the accuracy of the subject body model 987-0 when operating with parameter estimator 989 and LSTMs 991-1/2 but without GAN 979-0. Reference signal 973 can be compared to the predicted type X signal 971-2 from GAN 979-0 to determine the accuracy of the subject body model 987-0 with GAN 979-0. Reference signal 973 can be compared to the predicted type X signal 971-3 from subject body model 987-1 to determine the accuracy of the subject body model 987-1 without LSTMs 991-1/2 or a GAN 979-1. Reference signal 973 can be compared to the predicted type X signal 971-4 from GAN 979-1 to determine the accuracy of the subject body model 987-1 with GAN 979-1, but without parameter LSTMs 991-1/2.

A signal compare portion 985 can perform various other compare operations among the operational blocks of the system. For example, a signal compare portion could compare a type Y signal for time (T0, T1) from data source 908-1' with a predicted type Y signal output from LSTM 991-2 and/or a type Z signal for time (T0, T1) from data source 908-2 with a predicted type Z signal output from LSTM 991-1.

A block evaluator 983 can determine if any system blocks (e.g., LSTMs 991-0/1/2, parameter estimator 989, subject body models 987-0/1, or GANs 979-0/1) is operating below a desired accuracy level from comparison results provide by signal compare portion 985. If a block is performing below a desired accuracy level, feedback generator 977 can generate feedback signals 981 for the block. As but one example, an error measure for a block can be back propagated through the blocks model with an aim of minimizing the error.

It is understood that a "signal" as described herein, can be a machine learning signal, representing a time series expression of a measured value, in a suitable format (e.g., vector, matrix, tensor, etc.).

Figure 10:
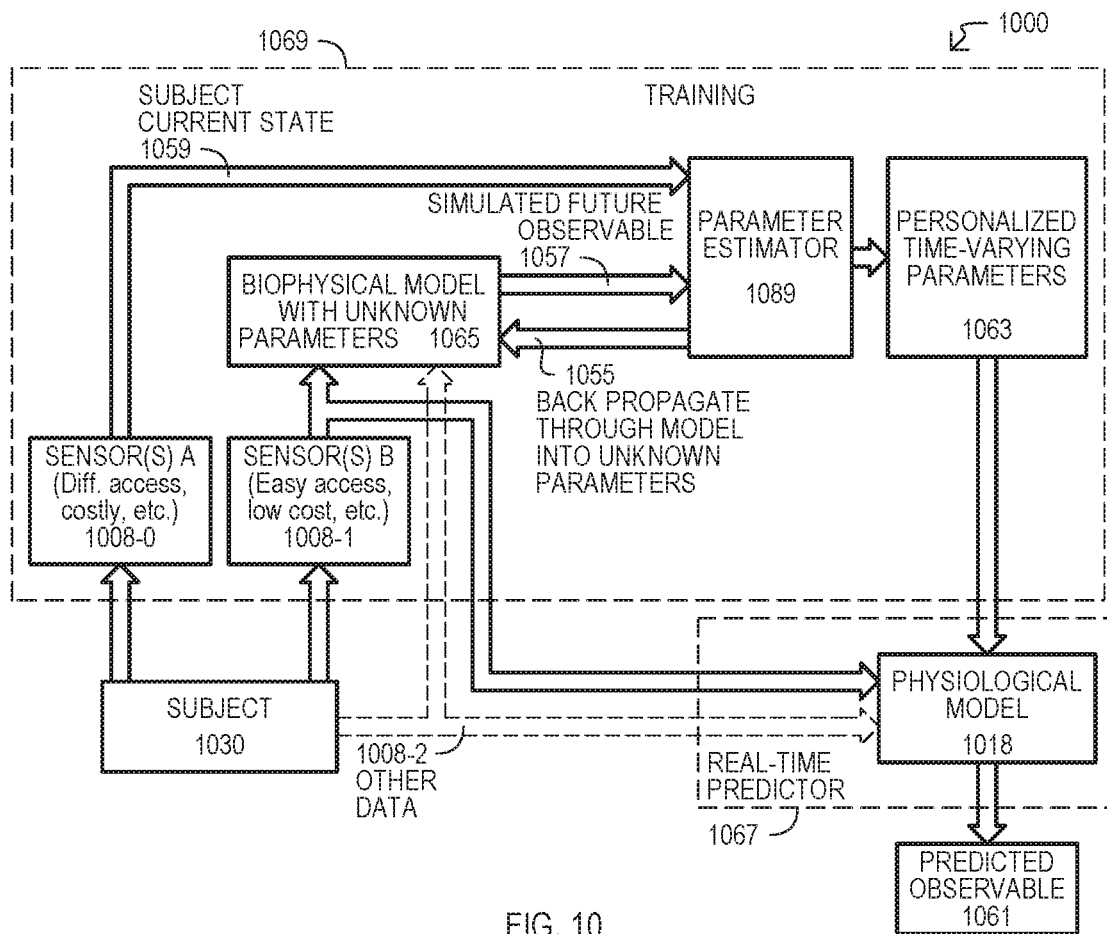
FIG. 10 is block diagram of prediction system according to an embodiment.

Embodiments can also include systems and method for predicting biophysical responses (i.e., a predicted observable) by observing biophysical responses for a limited time to create a predictive physiological model. FIG. 10 is a block diagram of a system and method 1000 according to such an embodiment.

The system/method 1000 can be conceptualized as including a training portion 1069 and a prediction portion 1067. A training portion 1069 can include a biophysical model 1065 and parameter estimator 1089 and can receive data for training from a subject 1030. In FIG. 10, data for training can include a first data source 1008-0, a second data source 1008-1, and optionally, a third data source 1008-2. The first data source 1008-0 can be a first type sensor and a second data source 1008-1 can be a second type sensor. According to some embodiments, it is desirable to use a first type sensor 1008-0 in a more limited fashion than a second type sensor 1008-1. As but a few of many possible examples, the first type sensor 1008-0 can be more expensive, more difficult to employ, or more difficult to access than a second type sensor 1008-1. For example, the first type sensor 1008-0 can be a CRM. In some embodiments, a first type sensor 1008-0 can provide more accurate data for a desired predicted observable than a second type sensor 1008-1.

Biophysical model 1065 can include an ANN, or any other suitable statistical learning agent, with initially unknown parameters. Biophysical model 1065 can receive, as training data over a period of time, data source 1008-1 (second sensor) and optionally, third data source 1008-2. In response to such data, biophysical model 1065 can generate a simulated future observable 1057. Parameter estimator 1089 can receive the simulated future observable 1057 as well as data from the first data source 1008-0 (first type sensor), which can reflect a subject's current state. Based on such inputs, parameter estimator 1089 can generate error values which can be used to back propagate 1055 through biophysical model 1065. Through such training, parameter estimator 1089 and biophysical model 1065 can arrive at time varying parameters 1063 for generating a simulated future observable 1057 that is personalized to the subject 1030.

A prediction portion 1067 can include a physiological model 1018 for a subject that uses the personalized time-varying parameters 1063 developed by the training portion 1069. In some embodiments, physiological model 1018 can include an ANN, or any other suitable statistical learning agent, having the same general structure as biophysical model 1065. Physiological model 1018 can receive data from second data source 1008-1 and optionally a third data source 1008-2. In response to such data, physiological model 1018 can infer a predicated observable 1061. Thus, a predicted observable 1061 can be generated without the use of a first data source 1008-0 (e.g., the more costly/difficult to use first type sensor).

Figure 11:
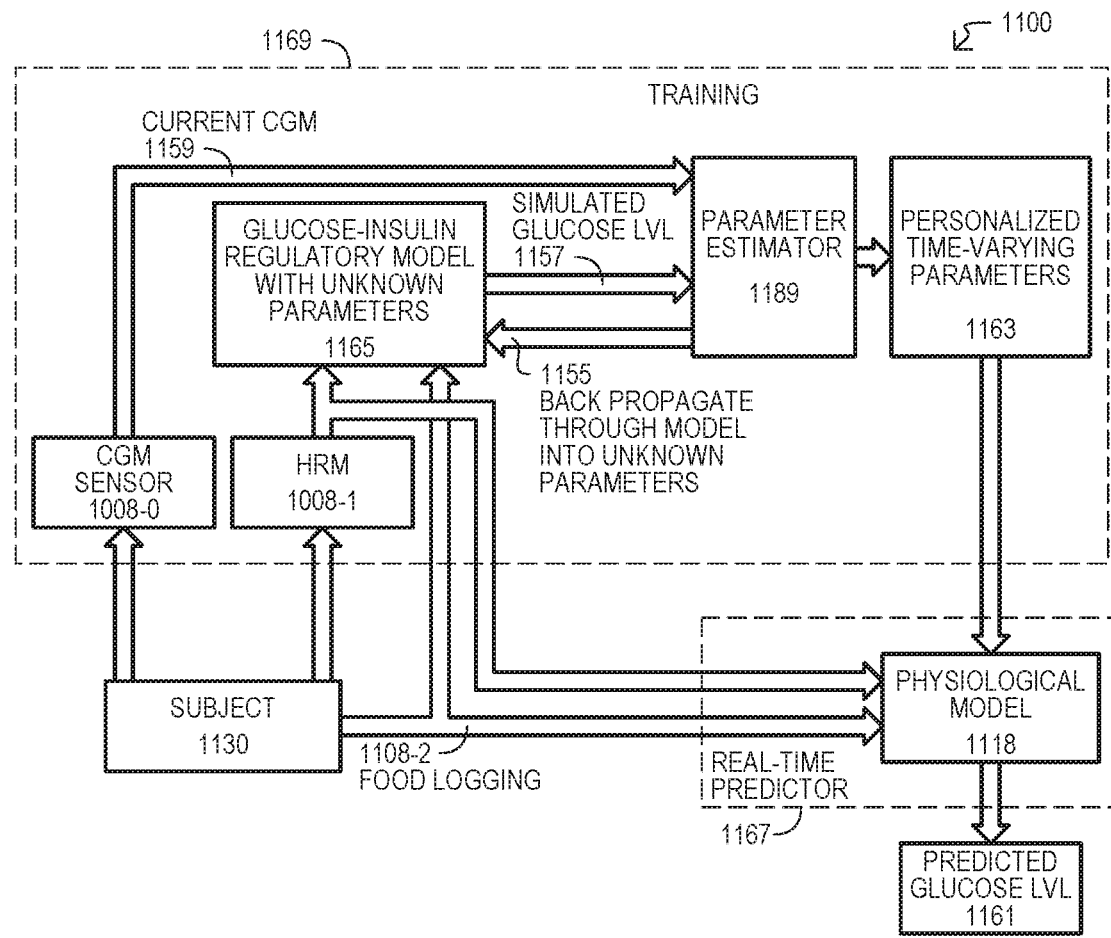
FIG. 11 is a block diagram of a glucose level prediction system according to an embodiment.

FIG. 11 is a block diagram of a system for predicting, in real-time, a glucose level of subject using personalized model, using only indirect data sources. "Indirect" data sources are data sources that do not measure a glucose level directly. System 1100 can be one implementation of that shown in FIG. 10.

The 1100 can include a glucose-insulin regulatory model 1165 and parameter estimator 1189. Model 1165 can initially include unknown parameters (e.g., default parameters not particular to a subject or randomized parameters). Model 1165 can receive training data from an HRM 1108-1 and food data logged by subject 1108-2 to generate a simulated glucose level 1157. Parameter estimator 1189 can utilize current CGM data 1159 from a CGM sensor 1108-0 of a subject 1130 and the simulated glucose level 1157 to back propagate 1155 through model 1165 to adjust time-varying parameters of the model 1165. Once model 1165 generates sufficiently accurate simulated glucose level 1157, time-varying parameters 1163 (which can be considered personalized to the subject 1130 as the model 1165 is trained with subject data) can be provided to real-time prediction portion 1167.

Real-time prediction portion 1167 can include physiological model 1118 which can receive personalized time-varying parameters 1163 developed by training portion 1169. Using indirect data sources of HRM 1108-1 and food logging 1108-2 (i.e., without the use of a direct measurement of glucose levels from CGM sensor 1108-0), physiological model 1118 can generate a predicted glucose level 1161. In this way, glucose levels can be predicted for a subject with less expensive, more accessible sensors.

While embodiments can include various systems and methods that utilize ML architectures for predicting and classifying subject behavior, embodiments can also include methods for providing data to such ML architectures.

Figure 12A:
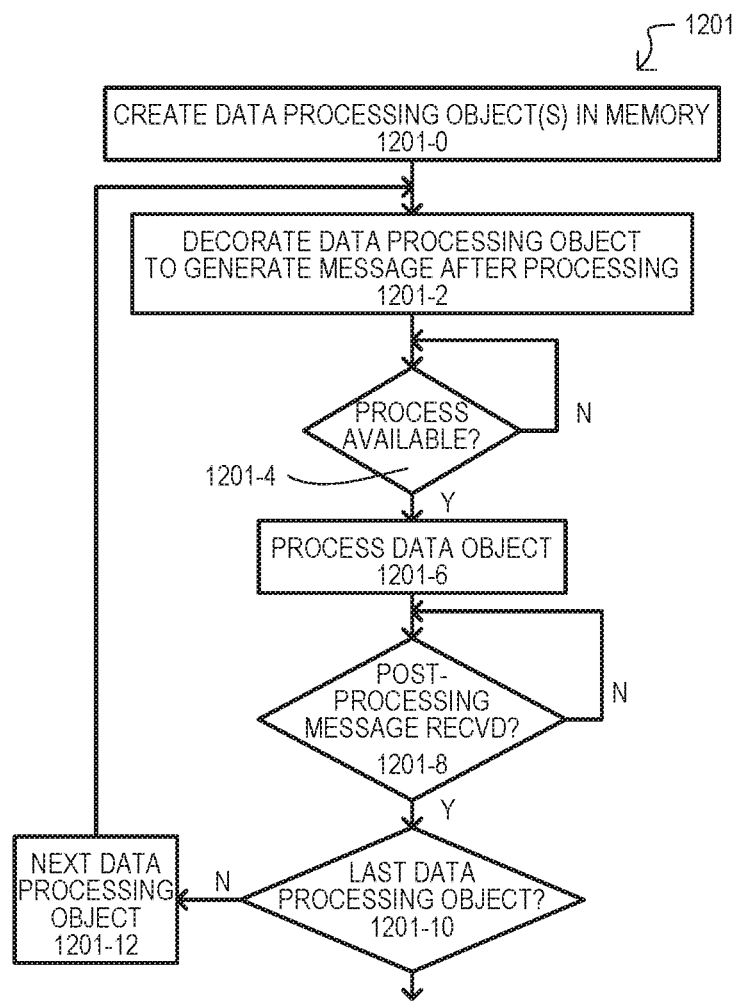
FIG. 12A is a flow diagram of a method for processing data objects according to an embodiment.

FIG. 12A is a flow diagram of a method 1201 for processing data objects according to an embodiment. The method 1201 can be performed by a system of one or more appropriately-programmed computers in one or more locations. The system can create one or more data processing objects in memory (1201-0). Such an action can include transferring data stored on a nonvolatile storage unit, or accumulating data received from a user in a system memory of a ML computing system. The system can decorate the data processing object to generate a message after it has been processed by an ML process (1201-2). Such an action can include transforming the data processing object into a more complex object that includes a messaging function.

The system can determine if a ML process is available (1201-4). If a process is available (Y from 1201-4), the system can process the decorated data processing object (1201-6). Such an action can include applying data to an ANN, or any other suitable statistical learning agent, for a training, inference, or other operation. The system can then determine if a post-processing message for the data processing object has been received (1201-8). Once a post-processing message has been received (Y from 1201-8), the system can determine if a last data processing object has been processed (1201-10). If there are more data processing objects to be processed (N from 1201-10), the system can proceed to the next data processing object (1201-12) and can return to 1201-2.

FIG. 12B is one example of code 1253 for decorating a data object according to one embodiment. Such code can be executable by one or more processors of a computing system. Code 1253 can include a function 1251, shown at (1) ("run_service"), which can decorate a data processing object to generate a message once it has been processed. At (2), the function can create an object in memory for receiving data to be processed. At (3), the data object in memory can receive data to be processed. At (4), a process target can be decorated to generate a desired message. At (5), one process of multiple forked processes can be instantiated to operate on the decorated object. At (6), the process can be started.

FIG. 12B also shows a function 1249-0 "service_encode" for encapsulating an egress message generated by a decorated data processing object, as well as the decorating function "post_process_decorator" 1249-1, which calls the message encoding function 1251-0.

Figure 12C:
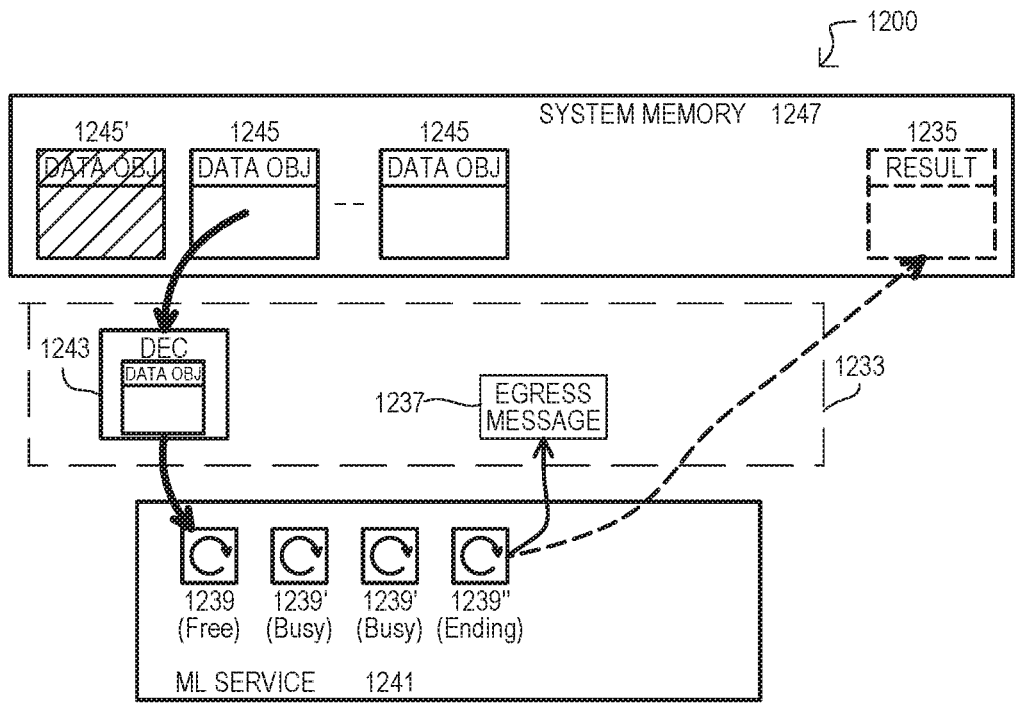
FIGS. 12C and 12D are diagrams showing the processing of data objects according to an embodiment.
Figure 12D:
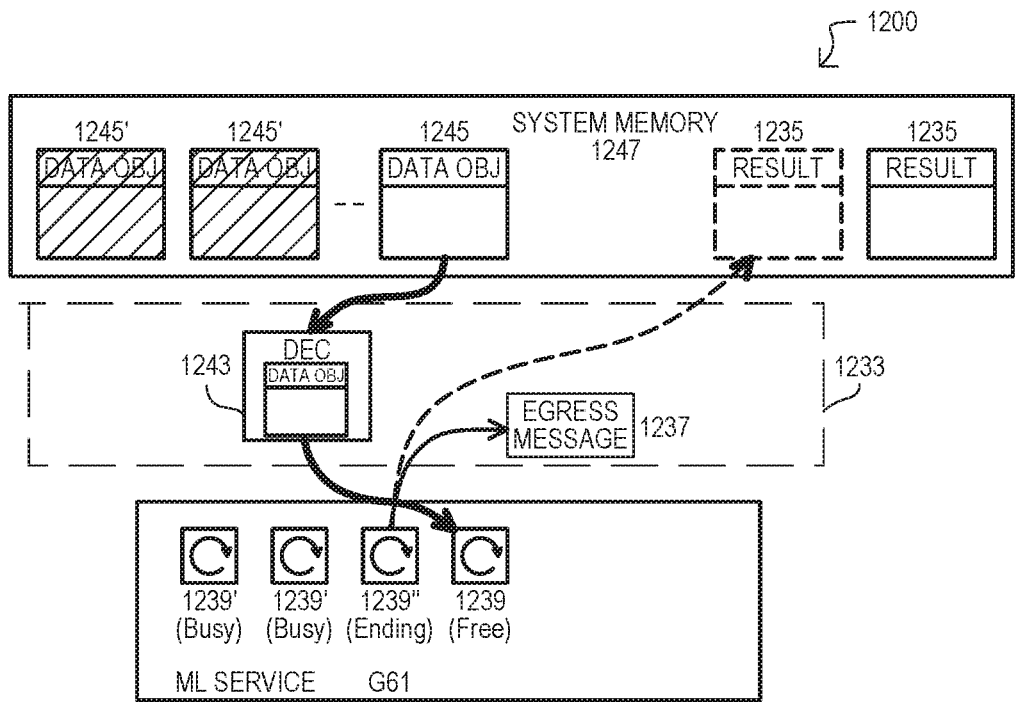

FIGS. 12C and 12D are block diagrams of a system 1200 showing a data processing operation according to an embodiment. Referring to FIG. 12C, system 1200 can include a system memory 1247, a machine learning service 1241, and pre- and post-processing functions 1233. Data processing objects can be created in system memory 1247. Data processing objects shown as 1245' have been processed to generate results 1235. Data processing objects shown as 1245 have yet to be processed.

Before data within a data processing object is processed, by operation of a decorating function, a data processing object 1245 can be transformed into an object 1243 that includes a messaging function. The object 1243 can be processed by an available process 1239 of ML service 1241. In some embodiments, processes of ML services 1241 can be asynchronous processes. Busy processes are shown as 1239'. A busy process that is ending (i.e., is the next process to be free) is shown as 1239". Once processing of data processing object is complete, results (e.g., 1235) can be returned to system memory 1247. In addition, by operation of the decoration, an egress message can be generated 1237.

Referring to FIG. 12D, the generation of egress message 1237 can be used as an indication that a process is available 1239. A next data processing object can be decorated 1243 and provided to the available process 1239.

While embodiments above describe various methods, both explicitly and implicitly, additional methods will be now be described with reference to a flow diagram.

Figure 13:
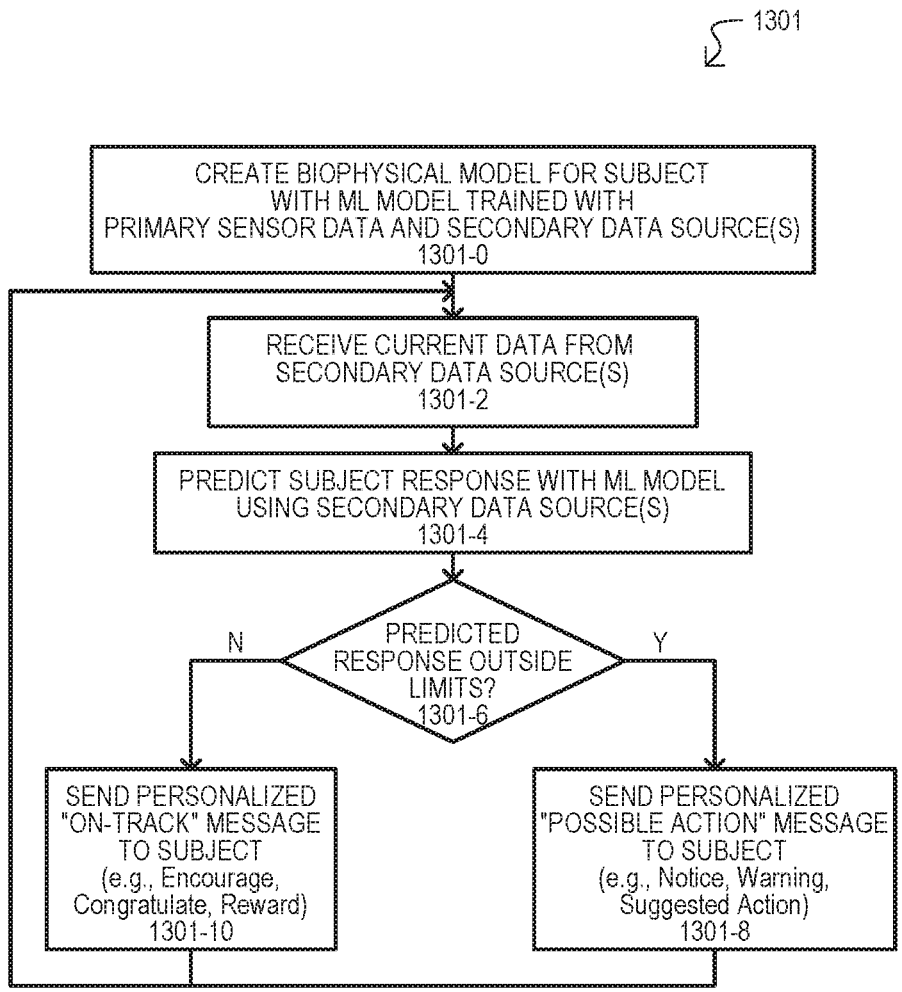
FIG. 13 is a flow diagram of a method according to an embodiment.

FIG. 13 is a flow diagram of a method 1301 according to an embodiment. The method 1301 can be performed by a system of one or more appropriately-programmed computers in one or more locations, e.g., one of the systems described previously in this disclosure. In an operation, the system can create a biophysical model for a subject with machine learning by training with primary sensor data and secondary data sources (1301-0). This operation can include creating models according to any of the embodiments herein, or equivalents. In some embodiments, a primary sensor data source can provide data for a subject response that is the same as that to be predicted. A secondary data source can provide data that is not the same as that to be predicted. In some embodiments, primary sensor data can be more difficult to acquire than data from secondary data sources. Further, primary sensor data sources and secondary data sources can be from a particular subject. Thus, the biophysical model can be a model personalized to a particular subject.

The system can receive current data from a secondary data source(s) (1301-2). Such an action can include receiving sensor data from a subject. A subject response can then be predicted with the biophysical model with at least the current secondary sensor data (1301-4). The system can determine if a predicted subject response is outside of one or more predetermined limits (1301-6). Such an action can include comparing a predicted response to limits or goals established by a subject. Such goals can be personal goals, or goals dictated by health needs. If a predicted response is not outside of limits (N from 1301-6), the system can generate one type of predetermined output (1301-10). In the particular embodiment shown, this can include a message for the subject indicating the subject is "on-track". If a predicted response is outside of limits (Y from 1301-6), the system can generate another type of predetermined output (1301-8). In the particular embodiment shown, this can include a message for the subject indicating a possible action to be taken. It is understood that outputs from actions 1301-08 and/or 1301-10 can be to third-parties or intermediate parties (e.g., medical professionals), as well as the subject.

In some embodiments, the system can predict the glucose level of a subject. A primary sensor can be a sensor that directly measures glucose levels (e.g., CGM). Secondary sensors can be sensors that track subject activity (e.g., HRM and/or food logging) but not the response to be predicted directly.

Figure 14:
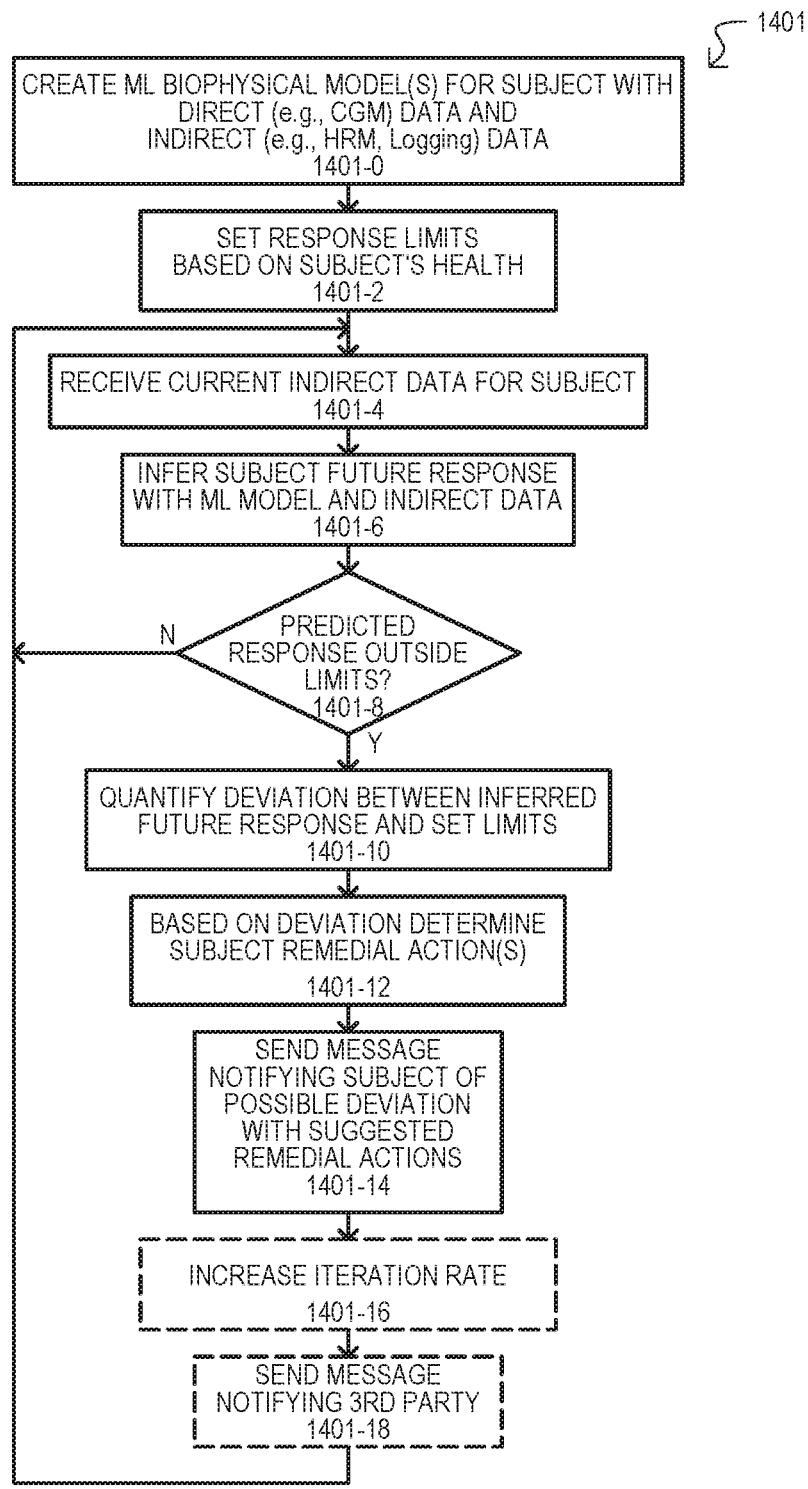
FIG. 14 is a flow diagram of a method of health management according to an embodiment.

FIG. 14 is a flow diagram of a method of health management 1401 according to an embodiment. The method 1401 can be performed by a system of one or more appropriately-programmed computers in one or more locations, e.g., one of the systems described previously in this disclosure. In an operation, the system can create one or more ML biophysical models for a subject with direct data and indirect data (1401-0). In some embodiments, a direct data source can provide data for a biophysical response that is the same as one predicted in the method 1401. An indirect data source can provide data that is not the same as that to be predicted. In some embodiments, all or a portion of data from a direct data source and/or an indirect data source can be from a particular subject to form a personalized biophysical model.

The system can set limits to a biophysical response based on the subject's health (1401-2). Such limits can be static limits or dynamic limits and can include rates of change. The system can receive current indirect data for a subject (1401-4). The system can infer one or more future responses of the subject from the indirect data using the models created in operation 1401-0(1401-6). The system can determine if a predicted response is outside of one or more response limits (1401-8). If a predicted response is not outside of limits (N from 1401-8), the system can return to 1401-4.

If a predicted response is outside of limits (Y from 1401-8), a deviation between the predicted response and the limits can be determined (1401-10). Based on such a quantified deviation, one or more remedial actions can be determined 1401-12. A message can then be sent to the subject notifying the subject of the expected deviation along with one or more suggested remedial action (1401-14).

Optionally, if a predicted response is outside of limits (Y from H70-8), an iteration rate (e.g., a rate at which indirect data is received or sampled) can be increased (1401-16), and/or a third party can be notified (1401-18).

Figure 15:
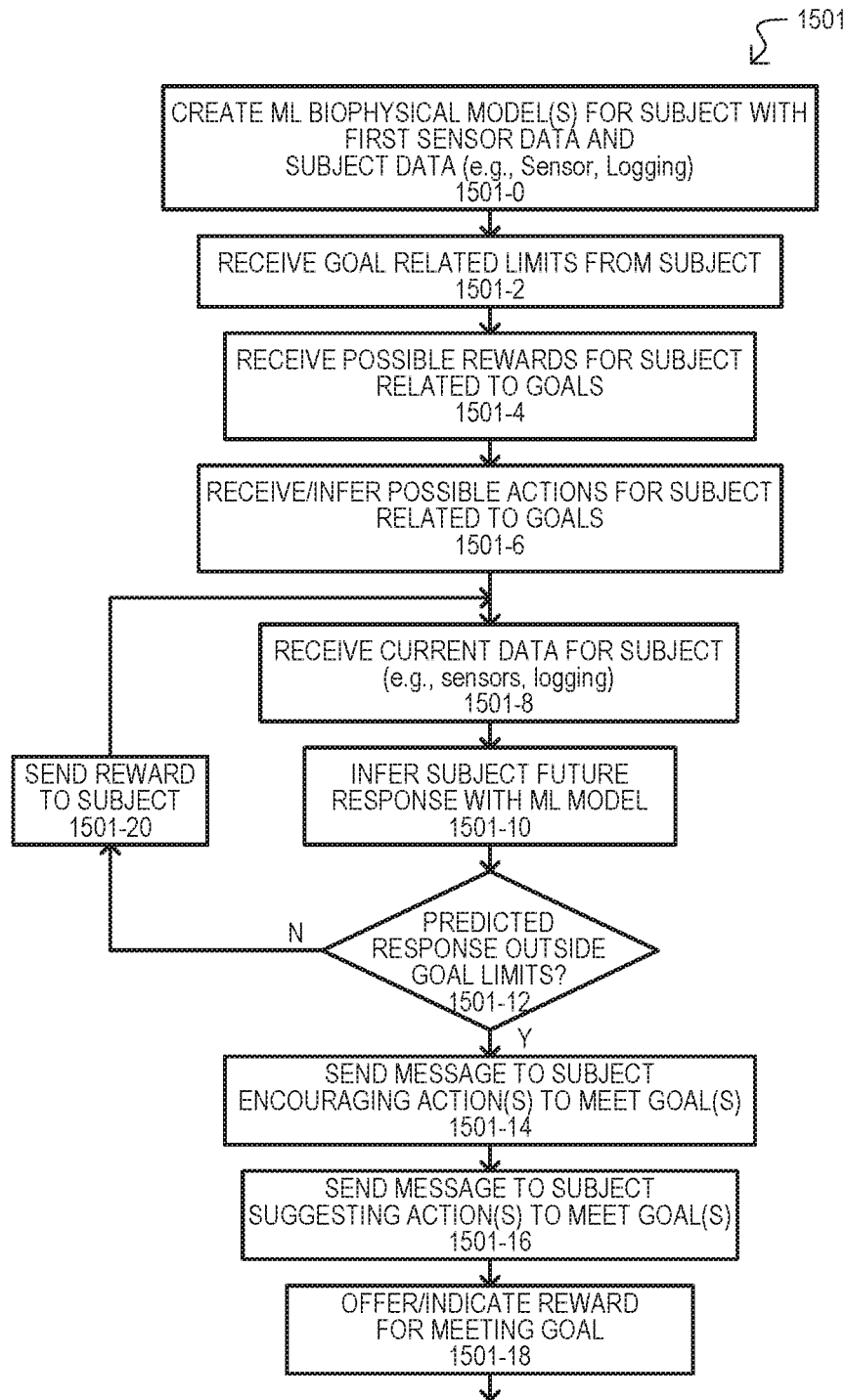
FIG. 15 is a flow diagram of a method of coaching according to an embodiment.

FIG. 15 is a flow diagram of a method of coaching a subject 1501 according to an embodiment. The method 1501 can be performed by a system of one or more appropriately-programmed computers in one or more locations, e.g., one of the systems described previously in this disclosure. The system can create one or more ML biophysical models for a subject with first sensor data and subject data (1501-0). Such actions can include creating models according to any of the embodiments herein, or equivalents. In some embodiments, first sensor data can be data from a sensor that takes biophysical readings directly from a human body. Subject data can be data provided by the subject.

The system receives goal-related limits from the subject (1501-2). Such actions can include receiving health, behavior or other goals from a subject, and determining how such limits can be sensed with a predicted subject response. Possible rewards for the subject can be received (1501-4). Such an action can include determining rewards based on a subject's personal preferences.

The system can also receive/infer possible actions for the subject related to subject goals (1501-6). Such an action can include determining activities a subject prefers, but such actions can also include using and/or presenting for selection "canonical" actions inferred as described herein, and equivalents.

Referring still to FIG. 15, subject data can be received (1501-8). Using such received data, a subject future response can be inferred the ML model from 1501-10. The system can determine if a predicted subject response it outside of one or more of the goal related limits (1501-12). If a predicted response is not outside of limits (N from 1501-12), the system can send a reward to the subject (1501-20). If a predicted response is outside of limits (Y from 1501-12), the system can send a message to a subject encouraging actions to meet goals (1501-14). In addition, a message can be sent suggesting particular actions that can be taken to meet goals (1501-16). Such particular actions can include actions from 1501-6. In the particular embodiment shown, the system can offer or indicate a reward for meeting goal(s) (1501-18).

Figure 16A:
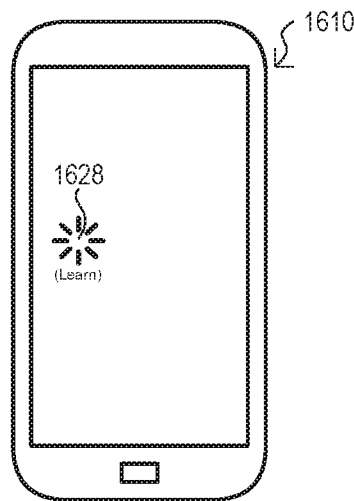
FIGS. 16A to 16C are diagrams showing a data acquisition application according to an embodiment.
Figure 16B:
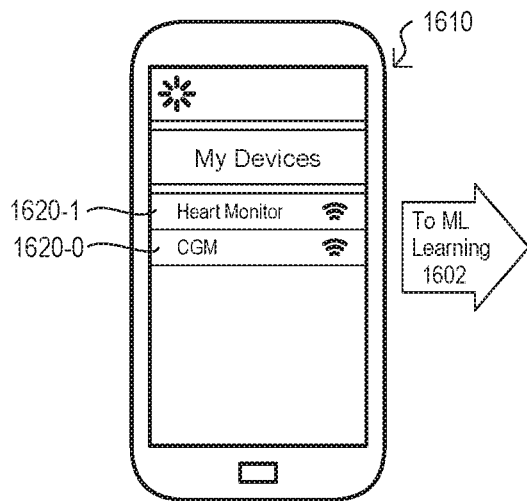
Figure 16C:
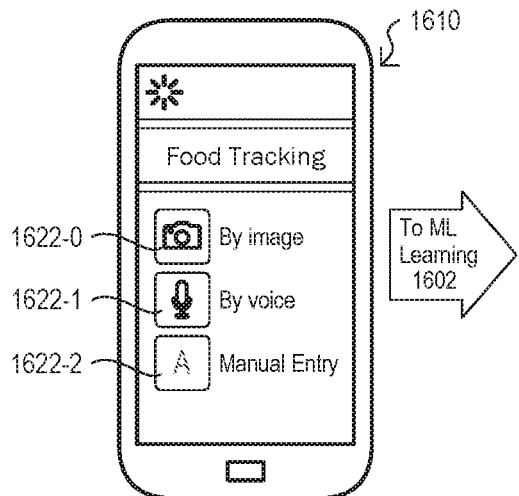

Referring now to FIGS. 16A to 16C, a subject device application and method for data acquisition is shown in a series of diagrams. Referring to FIG. 16A, a user device 1610 can include an application 1628 stored thereon in memory, such as nonvolatile memory, for execution by one or more processors of the user device 1610. While the user device 1610 is shown as a smartphone, the user device can take the form of any of those shown herein, or equivalents.

Referring to FIG. 16B, when an application is active, a user device can connect to, or be connected to, one or more sensor devices 1620-0, 1620-1. Sensor devices (1620-0, 1620-1) can sense biophysical responses of a subject. In the particular example shown, the sensor devices can include an HRM and CGM. However, alternate embodiments can include sensors suitable for a desired modeled response. Data from sensor devices (1620-0, 1620-1) can be provided, directly or via one or more other devices, to ML services 1602 for learning operations. Such learning operations can include any of those described herein or equivalents. In some embodiments, HRM and CGM data can be provided to ML services to create a personalized glucose level response model which can predict glucose levels.

Referring to FIG. 16C, an active application can also enable a subject to log data related to a predicted biophysical response. Such logged data can be provided, directly or via one or more other devices, to ML services 1602 for learning operations. In some embodiments, an application can provided various ways to log data values. In some embodiments, an application can enable food data (e.g., consumed food) to be logged by image capture 1622-0, voice entry 1622-1, or manually (e.g., enter text) 1622-2. However, such data entry methods should not be construed as limiting. As noted herein, such ML models can infer nutrition information from such logged data. That is, such data can also be used for initial inference operations which can yield nutrition data for learning operations.

Figure 17A:
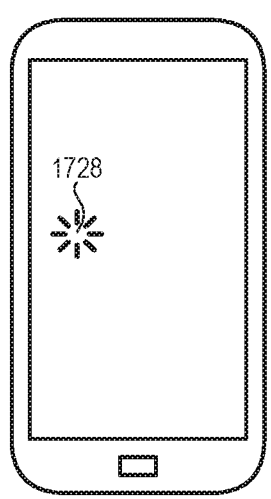
FIGS. 17A to 17F are diagrams showing a recommendation application according to an embodiment.

Referring now to FIGS. 17A to 17F, a subject device application for generating recommendations is shown in a series of diagrams. Referring to FIG. 17A, a user device 1710 can include an application 1728 stored thereon in memory, such as nonvolatile memory, for execution by one or more processors of the user device 1710. While the user device 1710 is shown as a smartphone, the user device can take the form of any of those shown herein, or equivalents. Application 1728 can be the same as, or different from, that shown in FIGS. 16A to 16C.

Figure 17B:
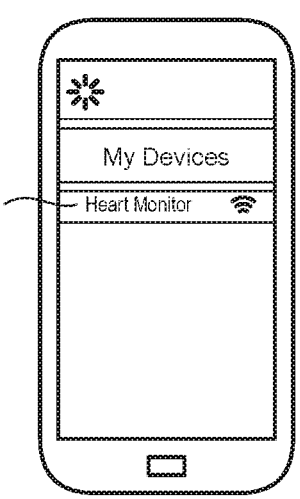

Referring to FIG. 17B, when an application is active, the user device can connect to, or be connected to, one or more sensor devices 1720-1. The sensor device 1720-1 can sense one or more biophysical responses of a subject. In some embodiments, the sensor device 1720-1 can be an indirect data source, sensing a biophysical response different from a biophysical response utilized to predict subject actions and make recommendations. In the particular example shown, sensor device 1720-1 can be an HRM that can provide data for predicting glucose levels of a subject. Data from sensor device(s) 1720-1 can be provided, directly or via one or more other devices, to ML services 1702 for inference operations. Such inference operations can include any of those described herein or equivalents. In some embodiments, HRM and other data can be provided to ML services to predict glucose levels of a subject.

Figure 17C:
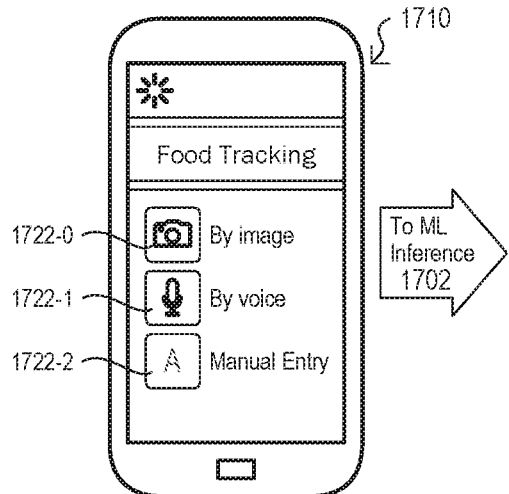

Referring to FIG. 17C, an active application can also enable the subject to log data related to a predicted biophysical response. Data logging can occur in the same fashion as noted for FIG. 16C (e.g., image 1722-0, voice 1722-1, manual entry 1722-2). However, logged data can be provided to ML services 1702 for inference operations. In particular embodiments, logged food data and HRM data can be used to forecast a subject glucose level.

Figure 17D:
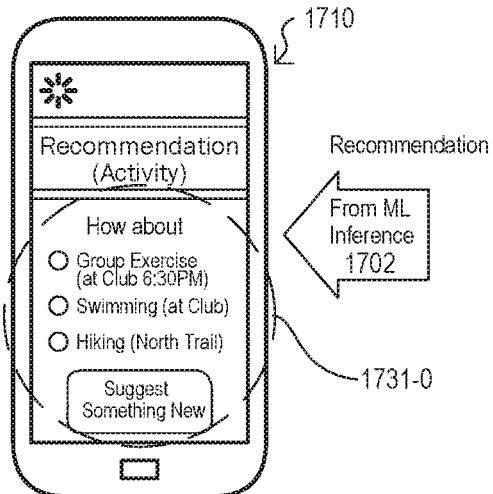
Figure 17E:
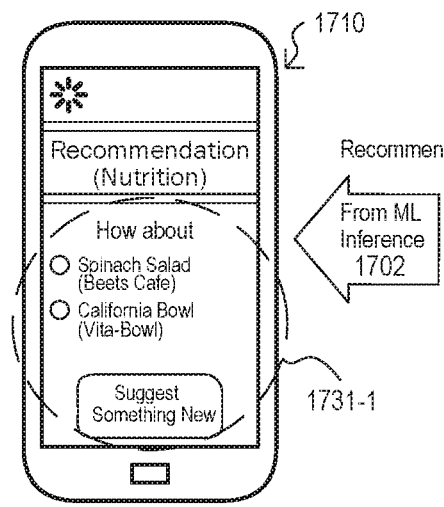

Referring to FIGS. 17D and 17E, in response to data from sensor 1720-1 and/or logged data, an application 1728 can receive recommendations from ML services 1702. Recommendations can be derived from an inference operation and/or from preferences or selections provided by a subject. In the embodiment shown, FIG. 17D shows an activity recommendation 1731-0. FIG. 17E shows a nutrition recommendation 1731-1.

Figure 17F:
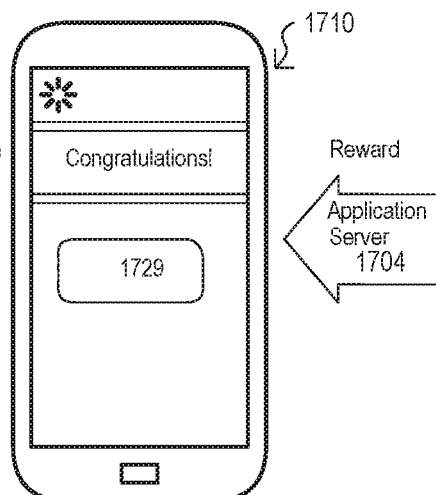

Referring to FIG. 17F, in the event a subject's predicted biophysical response(s) is within a desired limit, an application can offer a reward 1729. In some embodiments, a reward can be provided by an application server 1704.

Figure 18A:
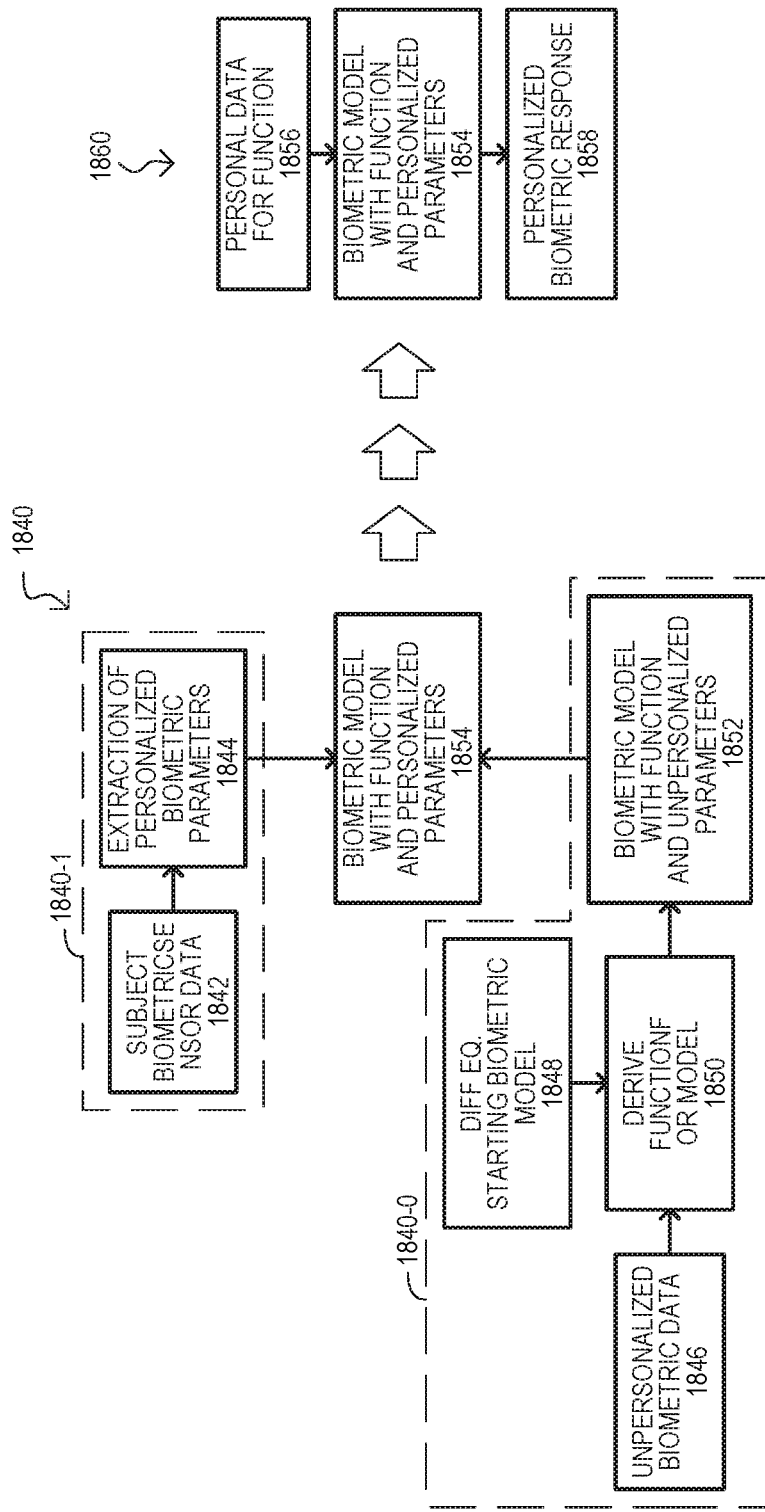
FIG. 18A is a block diagram showing a system and method for generating a personalized biometric response according to an embodiment.

FIG. 18A is a block diagram of a personalized response model creation system 1840 according to an embodiment. The system 1840 can include an unpersonalized model section 1840-0, a personalized data section 1840-1, and a resulting personalized model 1854. The unpersonalized model section 1840-0 can include unpersonalized biometric data 1846, a starting biometric model 1848, a derived function 1850, and an unpersonalized biometric model 1852. The unpersonalized biometric data 1846 can be data for a biophysical response over time for a general population, such as the rate at which one or more substances enter or are removed from the body or bloodstream. The starting biometric model 1848 can be a model for predicting a biophysical response, and in some embodiments can be in the form of a differential equation. The starting biometric model 1848 can include a number of functions, at least one of which may be derived from unpersonalized biometric data 1846. In some embodiments, deriving the model can involve using a machine learning operation (e.g., regression) to fits the unpersonalized data to a function. A biometric model with the derived function can be created. Because such a model includes one or more functions based on unpersonalized biometric data, it can include unpersonalized parameters.

Personalized data section 1840-1 can include subject biometric sensor data 1842. Personalized biometric parameters can be extracted from the personalized data 1840-1. The biometric sensor data 1842 can be sensor data for a subject for which a personalized response will be predicted. The extracted personalized parameters 1844 can represent the same parameters as the unpersonalized parameters of the model 1852. Extraction of personalized parameters 1844 can be accomplished with machine learning that seeks to fit biometric sensor data 1842 to an expected response. However, in other embodiments personalized parameters 1844 can be determined by other means, such as a clinical test, as but one example.

The unpersonalized biometric parameters of 1852 can be substituted with the extracted personalized parameters of 1844 to create a biometric model with the derived function and personalized parameter 1854.

FIG. 18A also shows a biometric response prediction system 1860. System 1860 can utilize the model from 1854 to provide a personalized biometric response for the subject of 1840-1. Personal data for the derived function 1856 can be provided to the model 1854, and the model can generate a personalized biometric response 1858. In some embodiments, system 1860 can execute an inference operation with the personal data 1856 as input data.

While systems as described herein can be utilized to provide any suitable personalized predicted biometric response, in some embodiments a model can predict a glucose over time (glycemic) response. Such an embodiment is shown in FIG. 18B.

Figure 18B:
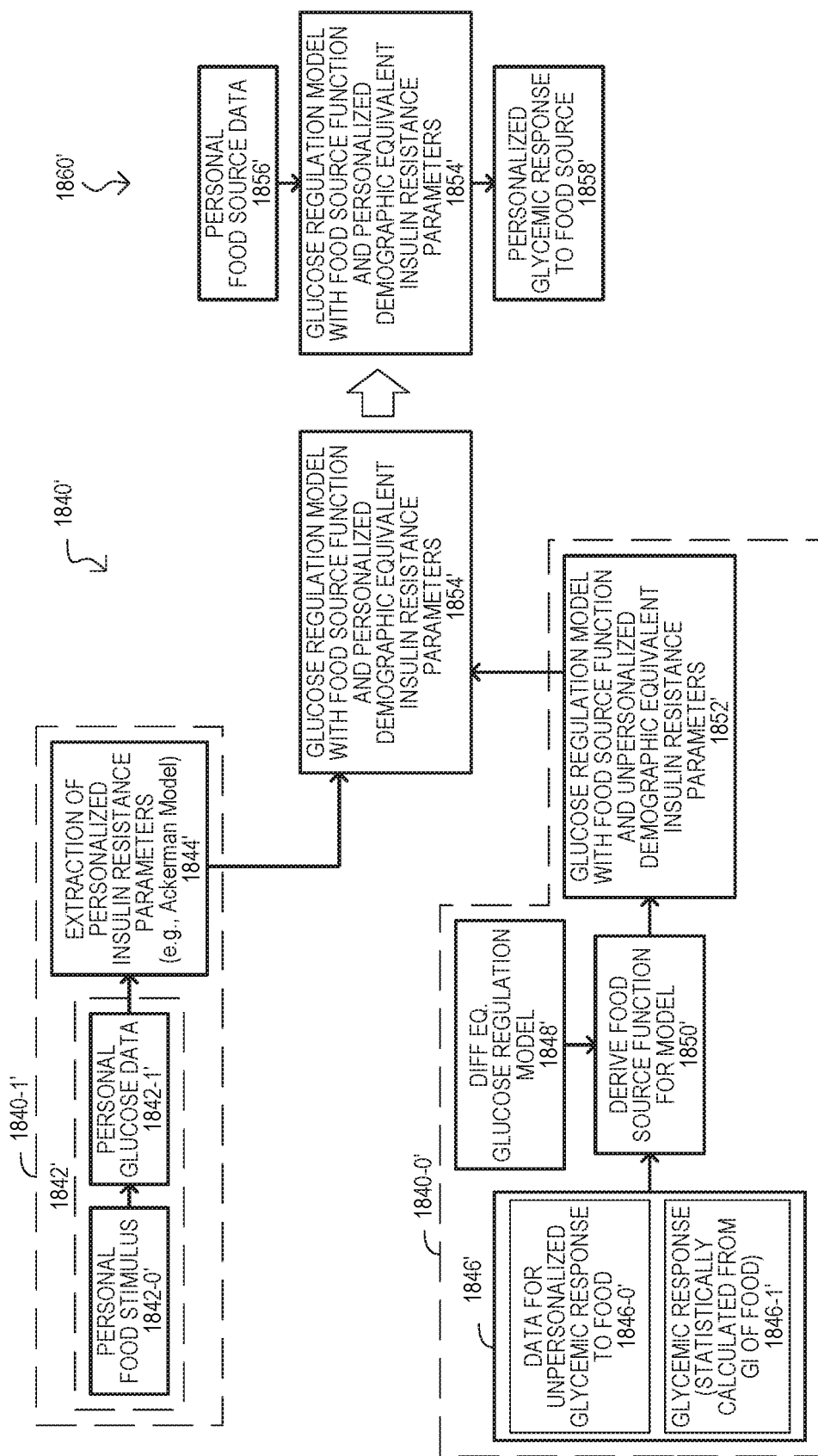
FIG. 18B is a block diagram showing a system and method for generating a personalized glycemic response corresponding to a food source according to an embodiment.

FIG. 18B shows a block diagram of a glycemic response model creation system 1840' according to an embodiment. The system 1840' can include an unpersonalized model section 1840-0', a personalized data section 1840-1', and a personalized glycemic prediction model 1854'. The unpersonalized model section 1840-0' can include unpersonalized response data 1846', a glucose regulation model 1848', a derived food function 1850', and an unpersonalized glycemic prediction model 1852'. The unpersonalized biometric data 1846' can be unpersonalized glycemic responses to food data 1846-0' and/or other glycemic response data 1846-1', from the general population. Other glycemic response data 1846-1' can be data statistically calculated from glycemic index data for food, as but one of many possible examples.

The glucose regulation model 1848' can be in the form of a differential equation that gives a glucose rate over time. As but one of many possible examples, the glucose regulation model 1848' can include a glucose production portion and glucose update portion. The food source function 1850' can be derived from the unpersonalized response data 1846'. In some embodiments, the food source function 1850' can be a function that expresses the generation of glucose in response to consumed food. In some embodiments, such a function can be derived using a machine learning operation (e.g., a regression model) that fits the unpersonalized data to a function.

One or more glucose regulation models 1852' can be created using the derived function. Such a model can include the food source function 1850' as well as unpersonalized glycemic response parameters. In some embodiments, such parameters can be demographic equivalent parameters by deriving (e.g., training) the model with demographic equivalent data sets. However, in other embodiments, demographic equivalent parameters can be "hidden" or embedded groupings that arise from unsupervised or supervised training. In a particular embodiment, such parameters can include one or more insulin resistance parameters.

The personalized data section 1840-1' can include personalized glucose response data 1842' and the extraction of personalized glycemic response parameters 1844'. Personalized glucose response data 1842' can include personal food stimulus data 1842-0' and a corresponding personal glucose data 1842-1'. In some embodiments, the personal food stimulus data 1842-0' can be data describing food eaten by a subject (e.g., food logging), while the personal glucose data 1842-1' can be glucose levels read by a sensing system, such as a continuous glucose monitoring (CGM) device, or some other glucose meter. Such data can represent a subject's personal glycemic response over time to the foods that the subject ate. The extracted personalized glycemic response parameters 1844' can correspond to the unpersonalized glycemic response parameters of 1852'. In a particular embodiment, such parameters can include one or more personal insulin resistance parameters. The parameters can be derived from the personal food stimulus data 22-0' and the personal glucose data 1842-1'.

The unpersonalized glycemic response parameters of 1852' can be substituted with the extracted personalized glycemic response parameters of 1844' to create a personalized glucose regulation model 1854'. In some embodiments, the personalized glucose regulation model 1854' can take the form of:

$$dG/dt = F_{food}(\text{food}, t \ldots) + F_{produce}(G(t) \ldots) + F_{uptake}(G(t) \ldots)$$

where dG/dt is the rate of change of glucose levels (e.g., blood glucose levels) in the body over time, $F_{food}$ is a food source function that can depend on characteristics of food eaten (food) and time, $F_{produce}$ can represent a body's glucose production, and $F_{uptake}$ can represent a body's glucose uptake. Any of the functions can include parameters as noted herein. For example, the insulin resistance parameters can be included in a function $F_{uptake}$.

FIG. 18B shows a resulting glycemic response prediction system 1860'. The system 1860' can utilize the model 1854' to provide a personalized glycemic response for the subject that provided personalized data 1842't. Food source data 1856' can be provided to the model 1854', and the model can generate a personalized glycemic response 1858'. In some embodiments, the system 1860' can perform an inference operation with the food source data 1856' as input data in real time.

In this way, embodiments can generate predicted glucose levels that can be more personalized than conventional approaches. In some conventional approaches, subject data can be extrapolated from a linear model, which may not capture the complexity of a glucose regulation system in the manner of a machine-learned solution, as described herein.

Further, embodiments herein present methods and systems that are easily and readily adaptable to individuals. Once a glucose regulation model has been constructed from unpersonalized data, personalized parameters for a subject can be incorporated into the glucose regulation model for predicting glucose levels of the that subject. This is contrast to conventional approaches that may use training data generated by the subject (e.g., food diary, blood glucose levels, activity) to create a model for that same subject. Then the same data is required an inference operation on the model. This is in sharp contrast to deriving personalized parameters and incorporating them into an existing model (constructed with unpersonalized data).

As noted herein, in some embodiments, personalized parameters for a subject can be demographic equivalent parameters. That is, features of a subject can be classified according to models created with large data sets to derive personalized parameters for the subject without having to test the subject. As but one of many examples, an insulin resistance parameter could be derived by classifying an individual according to any of various factors (e.g., age, sex, body size/type, lifestyle, location, place of family origin, know relatives, preferred diet, and numerous others) to generate a demographic equivalent insulin parameter, without the individual having to undergo a blood test, or the like.

While embodiments can include systems and methods for modeling and predicting subject biometric responses, embodiments can also include systems and methods for predicting a target feature of an item, without necessarily having all attributes of the item.

Figure 19A:
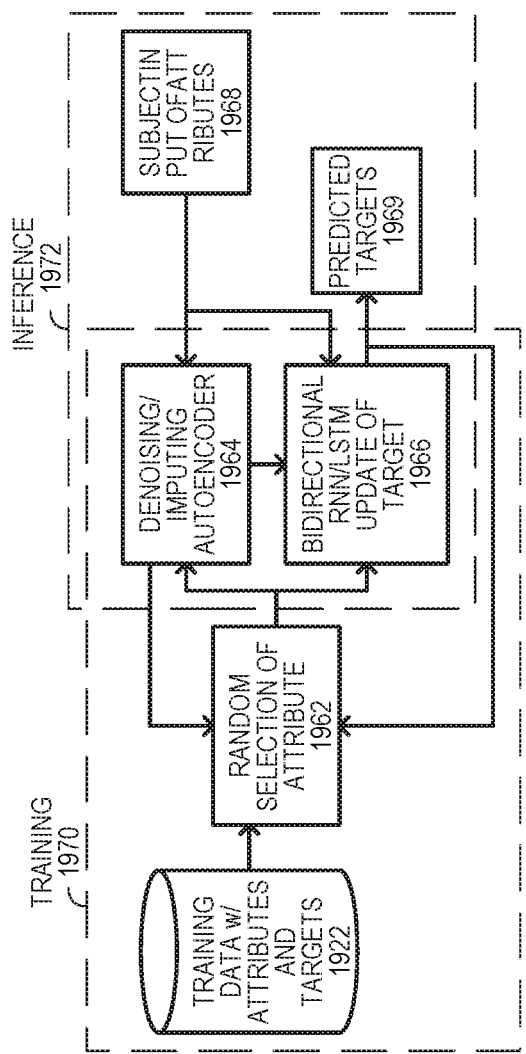
FIG. 19A is a block diagram showing a system and method for automatically predicting target values in response to attributes for such target values according to an embodiment.

FIG. 19A is a block diagram of a system and method for predicting a feature of an item according to an embodiment. FIG. 19A shows a training section 1970 for creating a prediction model, and an inference section 1972 for predicting target values. The training section 1970 can include training data 1922, a random selection of attributes 1962, an imputing AE 1964, and a bidirectional recurrent neural network (RNN) and/or LSTM 1966 (hereinafter LSTM).

The training data 1922 can include sets of attributes and a corresponding target for multiple data items. That is, each data item may be composed of multiple attributes which give rise to a target (feature) for the item. The target can serve as a label for training operations. An attribute for an item can be randomly selected from the training data. The AE 1964 can be trained to impute missing attributes from a subset of the attributes 1922, or from a corrupted set of the attributes 1922. The training process can involve providing the subset of attributes or the corrupted attributes to an untrained model, mapping such attributes to a hidden representation, and attempting to reconstruct the complete or uncorrupted attributes from the hidden representation. The reconstruction can be compared to the actual attributes, and the parameters of the model can be updated accordingly. This process can be repeated until convergence, i.e., until reconstruction error satisfies a criterion. In some cases, training attributes can be selected randomly (1962). The bidirectional LSTM 1966 can be trained on imputed attributes from AE 1964 along with a currently selected attribute to predict the target for the item from which attributes are selected.

An inference section 1972 can include a trained AE 1964 and trained bidirectional LSTM 1966. A subject can input attributes of an item 1968 to imputing AE 1964 and bidirectional LSTM 1966. As each attribute is input, imputing AE 1964 can impute missing attributes. In response to each input attribute and the imputed attributes, the bidirectional LSTM 1966 can generate a target feature 1969. In this way, the bidirectional LSTM 1966 can predict a target from an incomplete set of attributes.

While systems as described herein can be utilized to predict a target feature for any suitable items having multiple attributes, in some embodiments a system and method can predict a glycemic value for a food item. Such an embodiment is shown in FIGS. C2A and C2B.

Figure 19B:
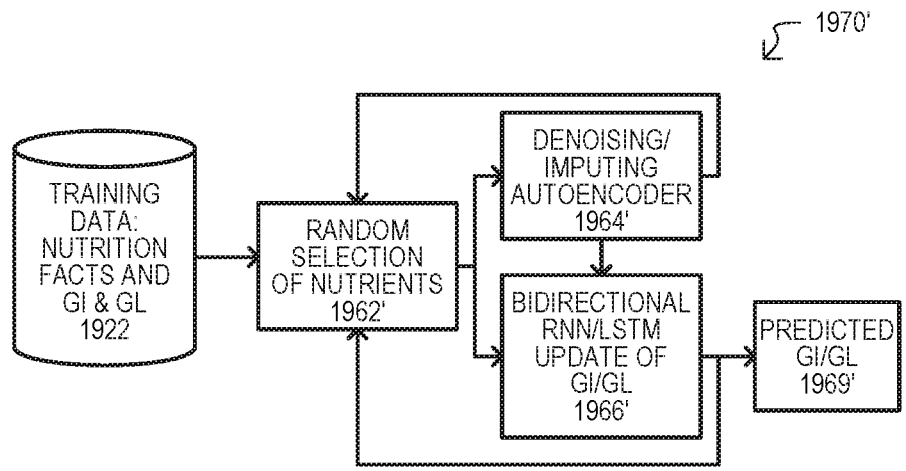
FIGS. 19B and 19C are block diagrams showing a system and method for automatically predicting a glycemic response as nutrients of a food item are sequentially input to a system according to an embodiment.

FIG. 19B shows a training section 1970' for creating a glycemic response model. Training section 1970' can include training nutrition data 1922', a random nutrient selection 1962', a denoising imputing AE 1964', and a bidirectional LSTM 1966'. Training nutrition data 1922' can include nutrients and a corresponding glycemic value for various food items. The glycemic value can be any suitable value related to a glucose response of a person (e.g., blood glucose), and in some embodiments can include a glycemic index (GI), glycemic load (GL), or both. The denoising and imputing AE 1964' can be trained to impute nutrient values for an item based on randomly selected nutrients. The bidirectional LSTM 1966' can be trained with imputed nutrients from denoising imputing AE 1964' and a currently selected nutrient to predict a glycemic value.

Figure 19C:
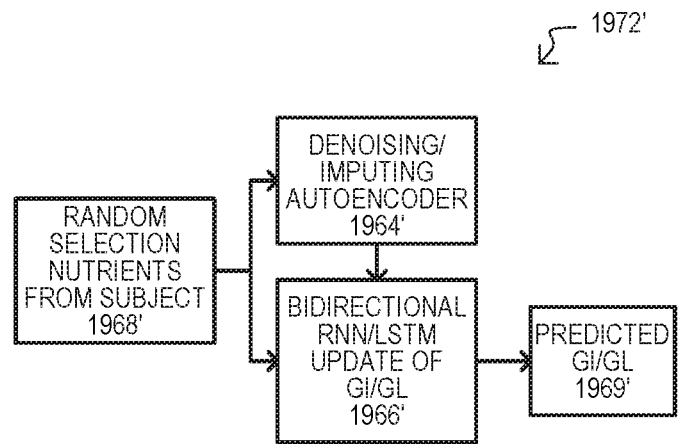

Referring to FIG. 19C, a glycemic value prediction method and system 1972' can include a denoising imputing AE 1964' and bidirectional LSTM 1966' trained as noted above in FIG. 19B. In an operation, a subject can input nutrients of a food item 1968' to denoising imputing AE 1964' and bidirectional LSTM 1966'. As each nutrient is input, denoising imputing AE 1964' can impute additional nutrients. In response to each input nutrient and the imputed nutrient, bidirectional LSTM 1966' can generate a predicted glycemic value. In some embodiments, glycemic values (GI/GL) can be provided to a subject in real time as each nutrient is entered.

While embodiments can include systems that can impute attributes to predict a target feature of an item, embodiments can also include systems and methods for imputing missing sensor data for a subject using multiple sensors.

FIG. 20A is a block diagram of a system and method 2076 for imputing missing sensor data according to an embodiment. The system 2076 can include one or more sensors 2078, ML embedding system 2080, ML imputation system 2082, and normalization system 2084. Sensor(s) 2078 can include one or more sensors that detect a biophysical response of a person over time. In some cases, the biophysical response data may be missing, corrupt, or otherwise determined to be not available or valid. ML embedding system 2080 can embed data from the sensors 2078 using an ANN. In this disclosure, the word "embed" or "embedding" may refer to a process by which data is mapped to vectors of real numbers. The resulting vector space may have a lower dimension than the input. As such, embedding may be considered a dimensionality reduction technique. When there are multiple sensors 2078, different sensor values can be grouped together (e.g., concatenated) during the embedding operation.

The ML imputation system 2082 can receive embedded values from the ML embedding system 2080 and impute values for any missing sensor readings. In some embodiments, the ML imputation system 2082 can include an AE similar to the AE of FIG. 19. The output of ML imputation system 2082 can be normalized with normalization system 2084. The resulting output can be imputed data 2086 which can include values that were not present in sensor data provided to the system 2076.

While systems as described herein can be utilized to impute data values for any suitable type of sensor data, in some embodiments the system and method can impute data for glucose and/or heart rate monitoring.

FIG. 20B is a block diagram of a system and method 2076' for imputing missing sensor data according to an embodiment. The system 2076' can receive data from multiple different sensor types 2016, 2018. In one embodiment, sensor 2016 can be a CGM and sensor 2018 can be an HRM. The ML embedding system 2080' can concatenate data from sensors 2016/2018 and embed them into single values using a neural network. In some embodiments, ML imputation system 2082' can include a stacked denoising AE. The normalization system 2084' can normalize the output of ML imputation system 2082' to generate imputed data 2086'.

FIG. 20C shows sensor data 2018 and 2016 prior to processing by a system 2076'. As shown, sensor data 2016 has a missing portion 417. FIG. 20D shows sensor data 2016', which can include imputed data 419 that has been provided by operation of the system 2076'.

Figure 21A:
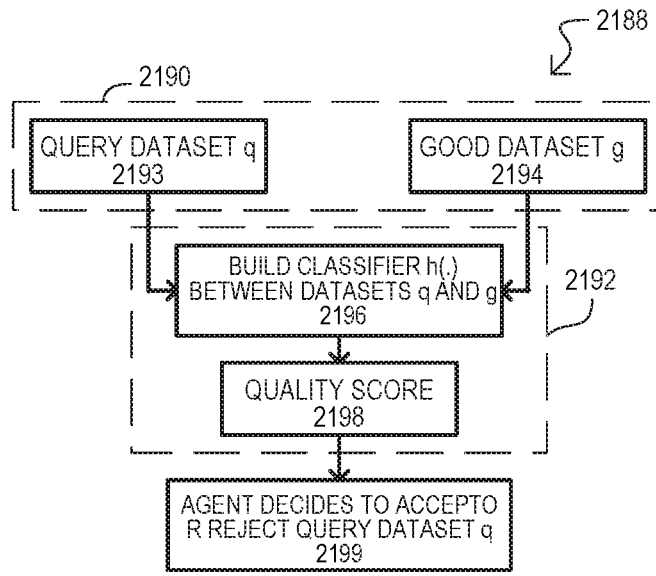
FIG. 21A is a diagram of a data set quality determination system and method according to an embodiment.

While embodiments can include systems that can impute missing data values from a sensor data set, embodiments can also include systems and methods for determining a quality of a data set. FIG. 21A is a block diagram of a method and system 2188 according to such an embodiment.

The system 2188 can include a database system 2190 and an electronic data processing system 2192. The database system 2188 can include one or more good data sets 2194 ($p$) and a query data set 2193 ($q$). The good data set 2194 can be a high-quality data set. The query data set 2193 can be a data set for evaluation. In some embodiments, data sets 2193/2194 can be labeled data sets.

Electronic data processing system 2192 can include a classifier section 2196 that gives a quality score 2198. The classifier section 2196 can include a neural network configured as a classifier. The classifier can be conditioned on both data values and corresponding labels for the data values. The distribution for the classifier can be $p(X, Y, Z)$ where $X$ can represent the input feature distribution, $Y$ can be a categorical target, and $Z$ can vary according to the data set. In some embodiments, Z can be a binary variance with Z=1 if a sample (x,y) is from a query data set (q), and Z=0 if a sample is from a validated data set (p). Thus, in the binary case, a classifier can be built to give $h(x)=p(z=1|x, Y=1)$. This is in contrast to a conventional classifier that can assume distributions from good and query data sets are the same (i.e., $p(X,Y|Z=0)=p(X,Y|Z=1)$) and is built for $h(x)'=p(y=1|x)$. The quality score 2198 can be a quality value determined by classifier section 2196. For example, in the above binary case, if $h(x)=0.5$ for all x in either the query dataset (q) or good dataset (g), the distributions can be determined to be indistinguishable, thus the query data set (q) can be considered high quality.

A software agent 2199 can then accept or reject the query data set (q) based on a generated quality score. Such an action can further include copying the query data set to a database for use in training, inference or other operations.

While systems as described herein can be utilized to determine a quality of various types of data sets, in some embodiments a system and method can determine a quality of data sets that include biophysical sensor data.

Figure 21B:
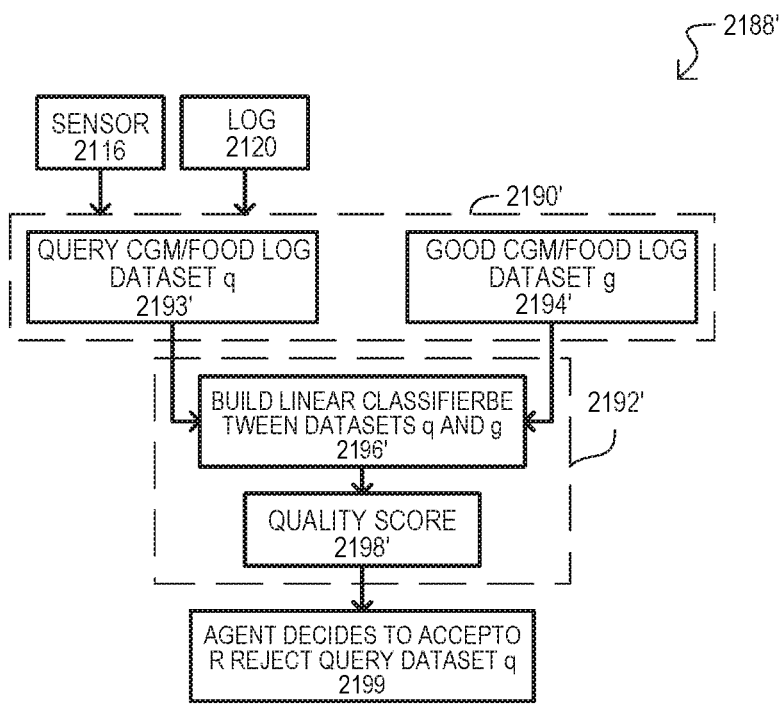
FIG. 21B is diagram of a system and method for determining a quality of data sets that include sensor data labeled with logged behavior data.

FIG. 21B is a block diagram of a system and method 2188' for determining a quality of glucose level data with corresponding food log labels. The system 2188' can include a database system 2190' and an electronic data processing system 2192'. The database system 2190' can receive data values from sensors 2116 and logged data 2120 and include a good data set 2194' (p) and a query data set 2193' (q). In some embodiments, data sets 2194'/2193' can be CGM data corresponding to food log data.

Electronic data processing system 2192' can include a linear classifier 2196' that generates a quality score 2198'. Linear classifier 2196' can include a neural network configured as a classifier similar to that described in FIG. 21A. Quality score 2198' can indicate how distinguishable the data sets were according to linear classifier 2196'. The quality score 2198' can vary according to types of data sets, and can take the form of those described herein, or equivalents. An agent 2199' can determine whether query data set 2198' is accepted or rejected.

Figure 22A:
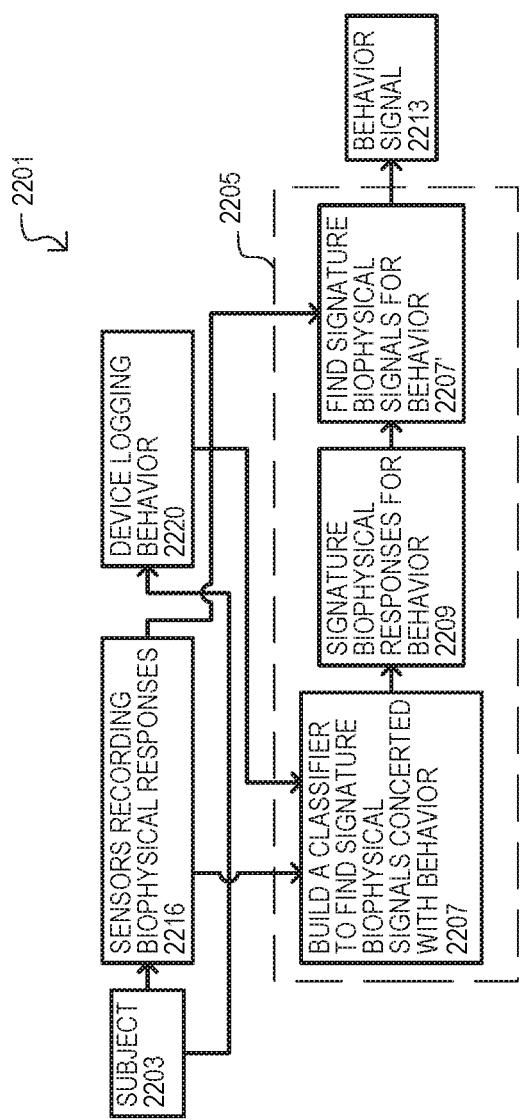
FIG. 22A is a block diagram of a system and method for determining a subject behavior from sensor signals according to an embodiment.

Embodiments can further include methods and systems that can predict a subject's behavior based on sensor signals. FIG. 22A is a block diagram of a method and system 2201 according to such an embodiment.

The method/system 2201 can include sensors 2216, subject logging data 2220 and a prediction system 2205. Sensors 2216 can include one or more sensors that record a biophysical response of a subject 2203. Subject logging data 2220 can record behaviors of a subject 2203.

The system 2205 can train a classifier 2207 to predict a behavior 2213 from a biophysical response 2216. The training data can be previous biophysical responses 2216 labeled with resulting previous behaviors 2220.

While systems as described herein can be utilized to determine any of various behaviors in response to sensor data, in some embodiments a system and method can predict food logging data in response to glucose and heart rate data from a subject.

Figure 22B:
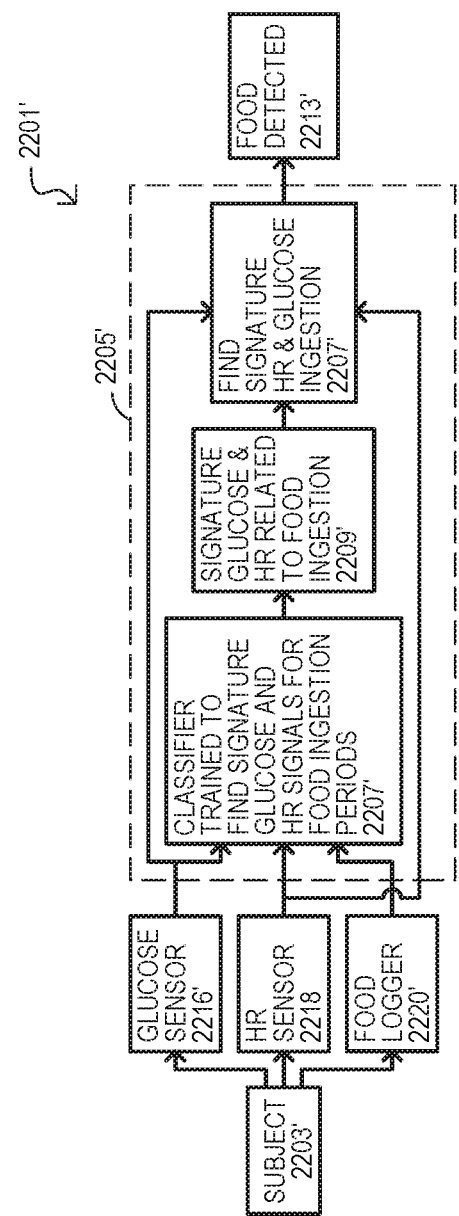
FIG. 22B is a block diagram of a system and method for determining food ingestion in response to sensor signals according to an embodiment.

FIG. 22B is a block diagram of a system and method 2201' that can include a prediction system 2205' that receives sensor data and food logging data 2220' from a subject 2203'. The sensor data can be from a glucose meter 2216' and HRM 2218.

Prediction system 2205' can train a classifier 2207' to derive signature glucose and heart rate signals for corresponding food ingestion periods 2209'. Predictor system 2207' can receive glucose sensor data and HRM data for a same time period, and in response predict an ingested food 2213' related to the time period.

Figure 23A:
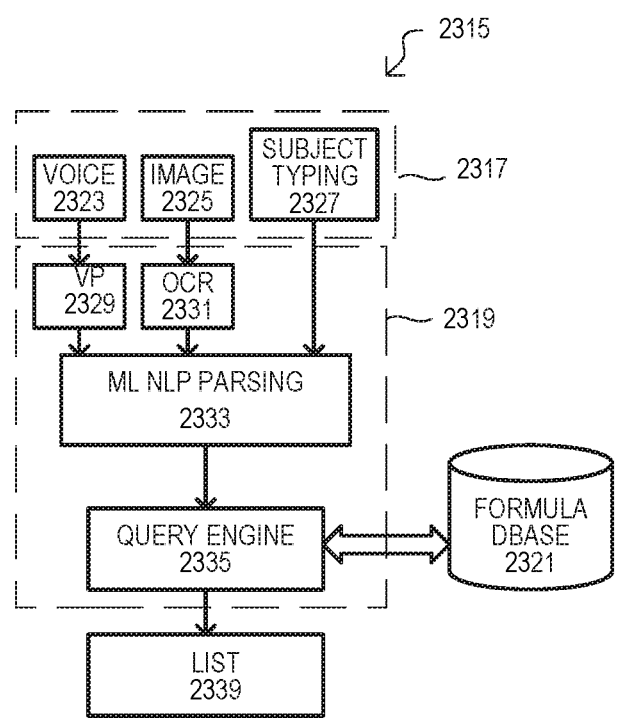
FIG. 23A is a block diagram of a system for determining the formula of an item from a text description of the item according to an embodiment.

Embodiments can further include systems and methods having machine learning models for determining the composition of items from a text description of the items. FIG. 23A is a block diagram of a system 2315 according to such an embodiment.

The system 2315 can include a data input section 2317, a processing section 719, and a formula database 2321. The data input section 2317 can acquire text-related data regarding an object. In some embodiments, the data input section 2317 can include voice data 2323, image data 2325, or text data 2327 from a subject. In some embodiments, such data can be acquired by a subject device (e.g., smartphone).

The processing section 2319 can transform non-text data into text data. Such processing can include voice processing 2329 to derive text data from audio input data or optical character recognition 2331 to derive text data from image data. While such processing can be performed by a remote system, all or a portion of such processing can also be performed by a subject device.

The processing section 719 can also include a machine learning natural language processing (NL) parser 2333 and a query engine 2335. NLP parser 2333 can determine a structure of input text. In some embodiments, the NLP parser 2333 can parse the text to determine its constituent words and can arrange such words in a particular order or format in response. The query engine 2335 can provide the arranged words to a formula database 2321 to determine an object corresponding to the text. In some embodiments, the query engine 2335 can generate a list 2339 of possible objects (e.g., prioritized list).

Figure 23B:
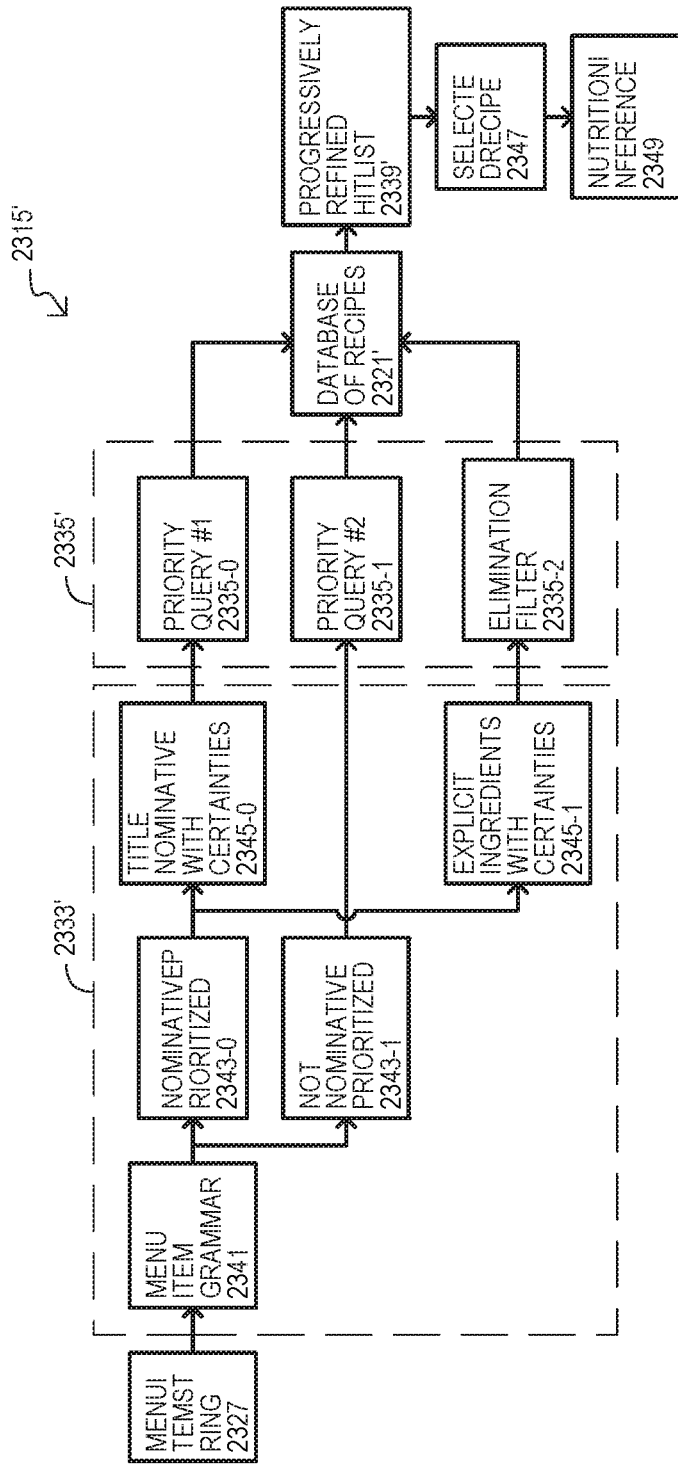
FIG. 23B is a block diagram of a system and method for determining the composition of a food item from a written description of the food item according to an embodiment.

While systems as described herein can be utilized to determine the composition of items based on text descriptions of the items, in some embodiments the composition of food can be determined from a text description of the food, such as a menu description. FIG. 23B shows an example of a method/system 2315' according to such an embodiment.

The method/system 2315' can receive a text string description of a food 2327. In some embodiments, such a text string can be a menu item description. A machine learning NLP system 2333' can parse the text string. Such parsing can include determining and prioritizing nominative words 2343-0 and non-nominative words 2343-1. Such processing can also include determining title nominatives, ingredient nominatives, and certainties with respect to such words. Based on such parsing, the NLP system 2333' can determine the presence and certainty of nominative words, and if so, prioritize such words, including title nominatives with certainties 2345-0 and explicit ingredients with certainties 2345-1.

Query engine 2335' can execute a sequence of query operations to a recipe database 2321' using parsed text data. In the embodiment shown, query operations can be prioritized, starting with title nominatives with certainties 2335-0. Query operations can then include secondary queries based on non-nominative prioritized words 2335-1. Query results can be filtered using explicit ingredients with certainties. In response to each query, a list 2339' of corresponding recipes can be progressively refined'.

The system can select a recipe 2347 from the list 2339'. In some embodiments, this can include selecting a recipe having a best match from the list. However, in other embodiments such an action can include a subject confirming or selecting a recipe from the list. A selected recipe can be applied to a nutrition inference system 2349 which can generate nutrition information (e.g., GI, GL) for the selected recipe.

Embodiments can further include systems and methods for determining the proportion of constituents in an item, based on features of such items. FIG. 24A is a block diagram of a method and system 2451 according to such an embodiment.

The method/system 2451 can receive data for an item composed of multiple constituents. Such data can include cost and/or reward values for the overall item 2453 and ranked constituent data 2455. Within an inference section 2457, given data 2453/2455, for each constituent of the item, the various cost/rewards for the item can be looked up to create a matrix 2457-0. In the embodiment shown, the item can include m constituents, and there can be n cost/rewards for the item, thus a lookup operation can generate an n×m matrix A. Using the generated matrix, the method/system 2451 can solve a system of equations 2457-1 for each cost/reward (e.g., y=Ax), with the constraints imposed by the known rank of ingredients (e.g., x1>x2 . . . >xm). Such an action can include instructions executed by a computing machine that solve the systems of equations according to any suitable technique. In some embodiments, a neural network can be used to derive equation coefficients using machine learning. Solving the system of equations can yield the amount of each constituent in the item 2459.

While system and methods as described herein can be utilized to determine the amounts of ranked constituents of any item given suitable cost/reward data, in some embodiments, the composition of a food item can be determined based on nutrition data for such a food item and a list of ingredients in the food item, such as that present in a food label. One such system is shown in FIG. 24B.

The system/method 2451' can include a data acquisition section 2461 and processing section 2457'. The data acquisition section 2461 can include an image capture device 2461-0 and image processing section 2461-1. The image capture device 2461-0 can be used to capture an image of a food item label. The image processing section 2461-1 can derive food item data from a captured label, including n food item nutrition facts (y1, y2 . . . yn) 2453' and m food item ranked ingredients (x1, x2 . . . xm) 2455'.

Inference section 2457' can lookup nutrient information for each ingredient to create an n×m matrix A for all ingredients 2457-0'. As in the case of FIG. 24A, a resulting system of equations for each ingredient (e.g., y=Ax) can be solved, with the rank of ingredients as constraints (e.g., x1>x2 . . . >xm). The resulting solved equations can give the amount of each ingredient in the food item (i.e., its recipe). A derived recipe can be provided to a nutrition inference system 2449 which can generate nutrition information (e.g., GI, GL) for the selected recipe.

FIG. 24C shows an example of food item data that can be processed according to embodiments. A food item 2463 can include a ranked ingredient list 2455" as well as nutrition facts 2453". However, the amount of each ingredient in the ingredient list 2455" is not known. Such data can be captured and processed by a method/system 2451' to infer the amount of each ingredient.

Embodiments can further include systems and methods for creating nutritionally sensitive word embeddings for processing word strings related to food.

FIG. 25A is a block diagram a method and system for training operations 2565 according to an embodiment. FIG. 25B is a block diagram of a method and system for an inference operation 2567 according to an embodiment.

Referring to FIG. 25A, the training method/system 2565 can include food data input 2569, a word embedding system 2571, and resulting nutritionally sensitive food string embedding 2573. The word embedding system 2571 can include an embedding section 2571-0 and weighing matrix 2571-1. The food data input 2569 can include word strings and nutrition facts for foods Within embedding system 2571, embedding section 2571-0 can embed food string values according to any suitable technique, including word2vec, as but one example. The weighing matrix 2571-1 can be included in training operations so that the nutrition facts corresponding to food strings are weighted in the word embedded space. Once trained, embedding system 2571 can provide nutritionally sensitive food string embedding 2573.

Referring to FIG. 25B, in an inference operation a query food string 2577 can be applied to a trained embedding system 2571, to generate a word embedding that is nutritionally sensitive 983.

While embodiments above describe various methods, both explicitly and implicitly, additional methods will be now be described with reference to a flow diagram.

Figure 26:
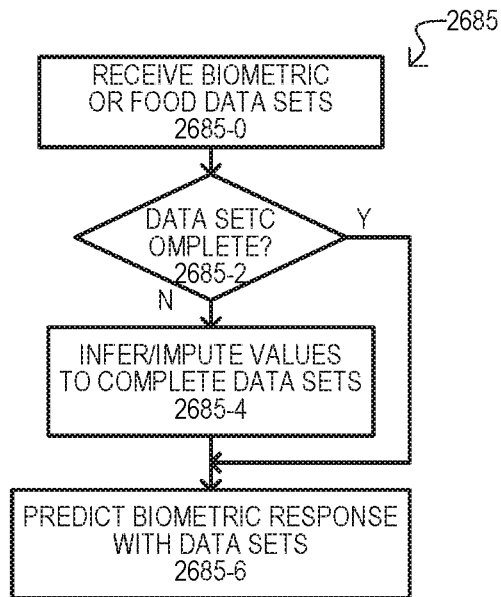
FIG. 26 is a flow diagram of a method according to an embodiment according to an embodiment.

FIG. 26 is a flow diagram of a method for completing data sets 2685 according to an embodiment. The method can be performed by a system of one or more computers in one or more locations. The system can receive biometric or food data sets (2685-0). Such an action can include receiving any of the data set types described herein, including but not limited to: CGM data sets, HRM data sets, and/or food logs. The system can evaluate such data sets (2685-2). Such an action can include determining if there are gaps in data sets, or data sets otherwise exhibit low quality. In some embodiments, this can include quality determination methods as described herein, or equivalents.

If a data set is determined not to be complete (N from 2685-2), values can be inferred and/or imputed to form a complete data set 2685-4. Complete data sets (Y from 2685-2 or 2685-4) can then be used to predict a biometric response 2685-6. In some embodiments, a biometric response can include blood glucose levels of a subject, including a personalized glucose response as described herein, or an equivalent.

Figure 27:
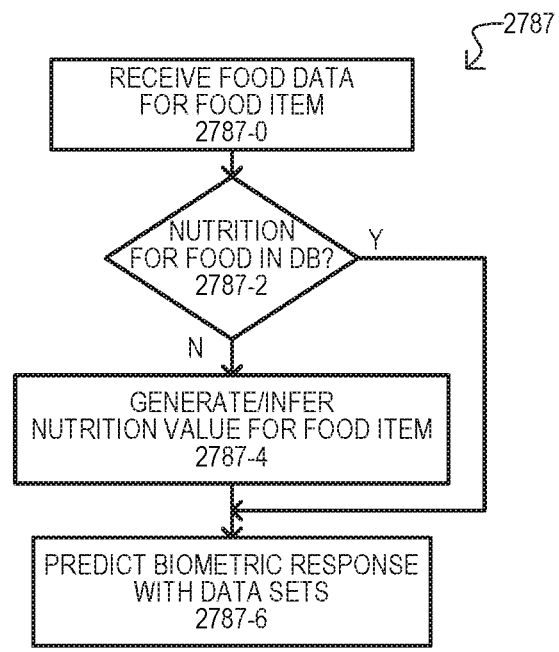
FIG. 27 is a flow diagram of a method according to another embodiment according to an embodiment.

FIG. 27 is a flow diagram of a method for deriving nutrition data for food items 2787. The method can be performed by a system of one or more computers in one or more locations. The system can receive food data (2787-0). Such an action can include a subject entering or otherwise acquiring data related to a food item according to any of the embodiments described herein or equivalents. The system can determine if nutrition data for the food item is in a database (or otherwise already known or available) (2787-2). If nutrition data is not known (N from 2787-2), the system can generate or infer nutrition value for the food item using the food data 2787-4. Nutrition data (Y from 2787-2 or 2787-4) can then be used to predict a biometric response 2787-6. In some embodiments, a biometric response can include blood glucose levels of a subject, including a personalized glucose response as described herein, or an equivalent.

FIG. 28 is a block diagram of a system for creating training data for an inference system for predicting a target value "Y" from mismatched data, as well as the inference system itself. The mismatched data can include first data that defines one or more attributes (e.g., text-based descriptions) of items (e.g., food items) and second data that defines target values to be predicted (e.g., glycemic values) for such items or similar items. In some embodiments, the attributes are easier to obtain than the target values.

The system 2800 can include an input data section 2806, embedding section 2818, training data 2806-2, and learning agent (e.g., NN) 2820A. Input data section 2806 can include mismatched data sets, including a first data set 2806-0 that includes items with attributes "X" and second data set 2806-1 that includes items of the same type with targets "Y". In this disclosure, the term "mismatched" may mean that attributes X for a particular item are known, but a target Y for the particular item is not known. Alternatively or additionally, the term "mismatched" may mean that the target Y for a particular item is known, but attributes X for the particular item are not known. In some cases, both X and Y may be known for a particular or for items with similar descriptions. Items of data sets 2806-0 and 2806-1 can be different and can have different identifying values. In some embodiments, data sets 2806-0/1 can include text values or text values that have been encoded as numerical values.

Embedding section 2818 can match items from data sets 2806-0 and 2806-1 by embedding the identifying values. In some embodiments, such action can include utilizing a neural network to generate embedded values that will correspond to attributes and targets. Data generated with embedding section 2818 can be stored as training data 2806-2. Training data 2806-2 can be used by a training agent 2832 to conduct supervised training on a neural network 2820A to predict target values Y from attribute values X. A trained neural network 2820B can then be used to predict targets Y from attributes X, without having to identify an item, but rather enter attributes of the item.

In some embodiments, the system 23300 can predict a glycemic value from nutrient data as shown in more detail in FIG. 29.

The system 2800 can include an input data section 2906, an embedding section 2918, training data 2906, and a learning agent 2932. The input data section 2906 can include at least one data set 2906-0 comprising descriptions of food items with nutrition information and at least another data set 2906-1 comprising glycemic data for such food items, similar food items, or different food items. Glycemic data can include a glycemic index (GI) and/or a glycemic load (GL). The data sets 2906-0 and 2906-1 can include the same or different food items.

The embedding section 2918 can map the word descriptions of food items with nutrition information and the word descriptions of food items with glycemic values to vectors of real numbers in a high-dimensional vector space. The embedding section 2918 can do so by using an unsupervised learning algorithm (e.g., a clustering or dimensionality reduction algorithm) or a neural network model, for example. Examples of such unsupervised learning algorithms are bag-of-words models and n-gram models. Examples of such neural networks are deep neural networks, autoencoders, or the like.

The distance between two vectors may represent the similarity of the descriptions of the food items represented by the two vectors. Such a distance can be used to infer the glycemic value of a food item for which the glycemic value is not otherwise known, or the nutrition information of a food item for which the nutrition information is not otherwise known. In some cases, both the nutrition information and glycemic value for a particular food item may be known and need not be inferred. The vectors of real numbers, which may be referred to as embeddings in this disclosure, can be used as training data 2906-2 by the supervised learning agent 2932. The labels for such embeddings can be the inferred or known glycemic values. The learning agent 2932 can train a neural network 2920A to infer GI or GL values from nutrient data. The resulting trained neural network 2920B can have nutrient facts as inputs and infer glycemic values.

Figure 30:
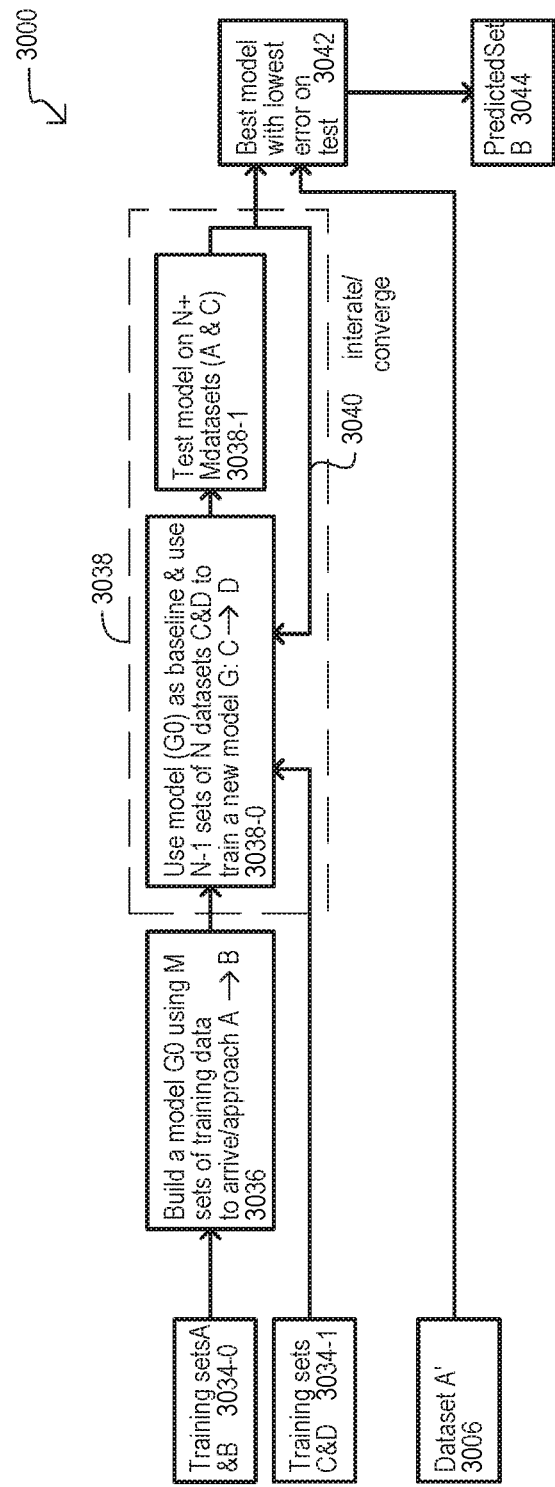
FIG. 30 is a block diagram showing a system and method for creating a model for predicting time series data, using time series training data sets, one or more of which may not have a high degree of accuracy.

FIG. 30 is a block diagram of a model creation system and method 3000 according to an embodiment. The system/method 3000 can include an initial model creation section 3036 and a model modifying section 3038, which can create a model 3042 for predicting data values. The system/method 3000 can create a model based on four different time series data sets: A, B, C and D. Data sets A & B can be related to training data sets 3034-0, and datasets C & D can be related training data sets 3034-1. In some embodiments, any or all such data sets can be time series data generated by one or more biophysical sensors. In some embodiments, data for data sets A and B alone may not be sufficient to create a satisfactory predictive model. As but one of many possible examples, either or both of data sets A and B can have gaps where data is incomplete or otherwise erroneous.

The initial model creation section 3036 can create an initial model (G0) with data sets A and B. In particular, using M sets of training data, a model can be trained to predict values B given values A. In some embodiments, such actions can include supervised training of a neural network model.

The model modifying section 3038 can use an initial model to create another model using different data sets. In the embodiment shown, this can include using the initial model G0 as a baseline and retraining or continuing to train the model G0 with data sets C and D to create a new model 3038-0. This can include using N−1 data sets of C and D to train the new model (G) to arrive at or approach values D given values C. In some embodiments, such actions can include supervised training of a neural network model. The model modifying section 3038 can further test the new model G data values from different training sets 3038-1. In the embodiment shown, such an action can include testing the model on N+M datasets of A and C. Such testing can include iterating through to convergence with sections 3038-0 and 3038-1. Through iteration and convergence a best model can be arrived at 3042 (e.g., lowest error model).

Time series input data set A' 3006 can be applied to best model 3042 to arrive at a predicted data set B (3044). In some embodiments, input data set A' 3006 can be sensor data of a subject and predicted data set B can be a predicted biophysical response for the subject.

While systems as described herein can be utilized to create models using different data set types, in some embodiments a model can predict time series data for a sensor of one modality type, using training data from sensors of different modality types. Such an embodiment is shown in FIG. 31.

Figure 31:
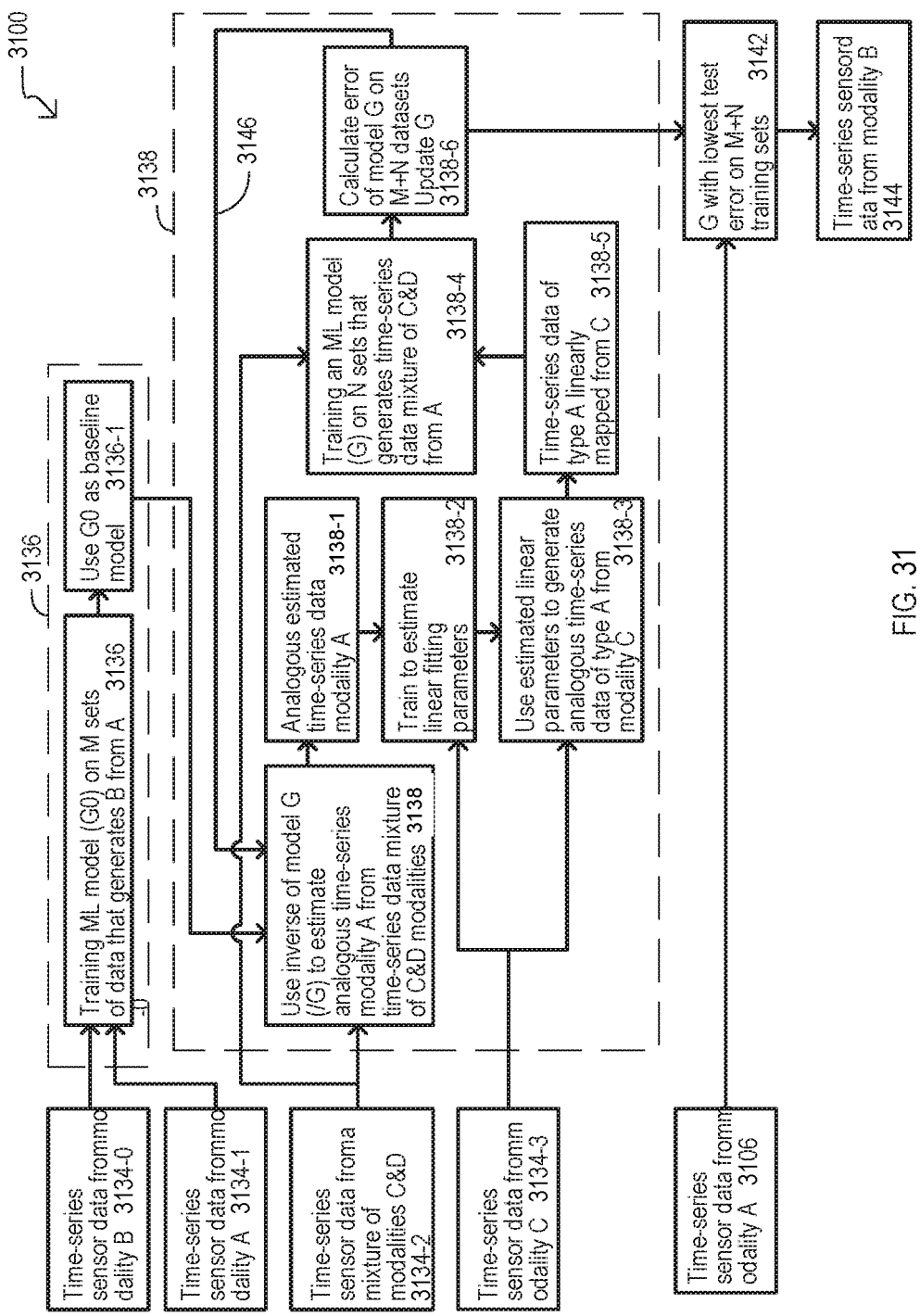
FIG. 31 is a block diagram showing a system and method for creating a model for predicting time series sensor data using time series sensor data of different modalities.

FIG. 31 shows a block diagram of a model creation system and method 3100 according to an embodiment. The system/method 3100 can predict time series sensor data of a modality B from time series sensor data of modality A. Time series sensor data of different modalities can be sensor data acquired with different sensor types and/or sensor data acquired using different procedures.

The method/system 3100 can include an initial ML model section 3136 and an ML model modifying section 3138. Such sections can use training time series sensor data sets of different modalities A, B, C and D to create a model to predict sensor data sets of modality B from sensor data sets of modality A. Initial ML model section 3136 can receive training time series sensor data of modality B 3134-0 and modality A 3134-1. The model (G0) can be trained on M sets of data to predict modality B from modality A. In some embodiments, training data sets A and B are not sufficient to ensure the creation of a model of sufficient accuracy for a desired result. A resulting model (G0) can be used as a baseline model 3136-1.

Within the ML model modifying section 3138, an inverse of model G0 can be used, referred to as inverse model "/G", to estimate time series data analogous to modality A from different modality data 3138-0. In the embodiment shown, a mixture of time series data of modalities C and D 3134-2, can be used on the inverse model /G. Using analogous modality A data generated with the inverse model /G 3138-1, and time series data of modality C 3134-3, the inverse model /G can be trained to estimate linear fitting parameters 3138-2 to generate analogous modality A data from modality C data 3134-3. Using the estimated linear fit parameters, analogous modality A data can be generated that is mapped to modality C data 3138-5.

A model G (of which /G is the inverse) can then be trained using time series of mixed modalities C & D 3134-2 and the analogous modality A data 3138-5. In particular, the model G can be trained to generate time series of mixed modalities C & D from the analogous modality A data from 3138-4.

An error can be calculated for model G on M+N data sets, and based on such error, the model G can be updated 3138-6. Based on the updated model, a method/system can return to 3138-0, to generate a revised inverse model /G. Such a process can continue to iterate 3146 until a model of minimum error is generated 3142.

Time series sensor data of modality A 3106 can be applied to the minimum error model G 3142 to generate time series sensor data of modality B 3144.

In some embodiments, two or more time series sensor data can include a different types of glucose meters generating glucose levels.

While embodiments can include systems and methods for modeling and predicting time series data, embodiments can also include systems and methods for correcting time series data sets that can be subject to error over time.

Figure 32:
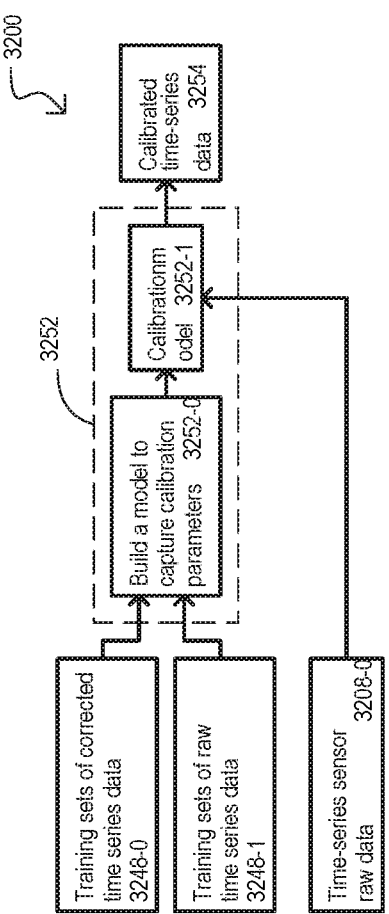
FIG. 32 is a block diagram showing a system and method for creating a model for calibrating time series data.

FIG. 32 is a block diagram of a system 3200 for correcting time series data according to an embodiment. The system 3200 can include a model section 3252 that can create a correcting model by training with correct (or corrected) time series data 3248-0 and raw time series data 3248-1, which may have inherent or introduced error.

The model section 3252 can train a calibration model 3252-1 to generate corrected or calibrated time-series data 3254 from time-series sensor raw data 3208-0. The model can be trained on training sets of raw (3248-1) and corrected (3248-0) time series data. The training sets of raw time series data 3248-1 can be provided as inputs to the untrained or partially trained calibration model 3252-1, and the training sets of corrected time series data 3248-0 can serve as labels. The output produced by the untrained or partially trained calibration model 3252-1 can be compared to the labels, and based on the difference, which may be referred to as an "error" or "loss," the parameters of the calibration model 3252-1 can be updated. This process can be repeated until the error or loss is consistently small. In some cases, the calibration model 3252-1 can be a deep learning neural network.

Trained calibration model 3252-1 can then be deployed to calibrate time series data to compensate for error. In particular, time series sensor raw data 3208-0 can be applied to the model to generate calibrated time-series data 3254. In some embodiments, such an action can include applying time series sensor raw data 3208-0 as input data in an inference operation on a neural network-based calibration model.

While systems and methods as described herein can be utilized to correct any suitable set of time series data, in some embodiments a system and method can correct for drift in glucose level data generated by a glucose meter. Such an embodiment is shown in FIGS. 8A to 8C.

FIG. 33A is a block diagram of a system 3300 for calibrating raw time series glucose data according to an embodiment. The system 3300 can include a model section 3352 for creating a model by training with sets of corrected time series glucose data 3348-0 and raw time series glucose data 3348-1. In some embodiments, raw time series glucose data 3348-1 can be generated by a glucose meter that can drift over time. Such drift can arise from a hysteretic effect in the glucose meter that can introduce a dynamic error into sensor readings. Corrected time series glucose data can be data that has be validated, and so is known to be accurate.

The model section 3352 can train a statistical ML model with the training sets of corrected time series glucose data 3348-0 and raw time series glucose data 3348-1 to infer time-variant drift cancellation parameters 3352-0. Optionally, the model section 3352 can include domain-specific engineering 3356. However, other embodiments can include automatic feature extraction. Parameters derived at 3352-0 can be used to create a drift cancellation model 3352-1.

Drift cancellation model 3352-1 can then be deployed to calibrate time series glucose data 3354 from raw time series glucose data 3308-0. In particular embodiments, raw time series glucose data 3308-0 can be applied as input data in an inference operation to drift-cancellation model 3352-1.

FIG. 33B shows raw time series glucose data 3308-0 which can be applied to a trained drift cancellation model 3352-1. FIG. 33C shows corresponding calibrated time series glucose data 3354 generated by operation of a trained drift cancellation model 3352-1 on the raw time series glucose data 3308-0.

While embodiments can include systems and methods that can calibrate time series data to account for inherent error, embodiments can also include systems and methods for organizing data sets to enable the identification/searching of such data sets for concerted events.

Figure 34:
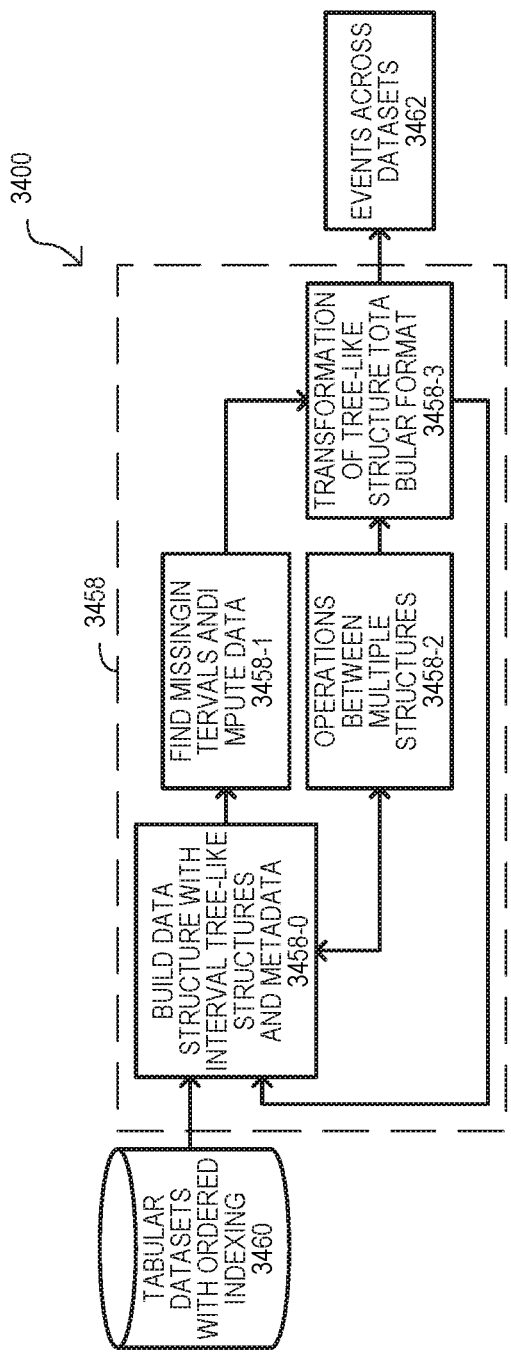
FIGS. 34 and 35 are block diagrams showing systems and methods for creating interval tree like structures from tabular data sets to present data for events across the data sets according to embodiments.

FIG. 34 is a block diagram of a system and method 3400 for organizing data sets according to an embodiment. The system 3400 can include an operational section 3458 and a data set source 3460 and can extract events across multiple data sets. Data set source 3460 can include a data storage system configured to store a number of data sets with ordered indexing. In some embodiments, data sets can represent events occurring according to the ordered index. In some embodiments, data sets can be tabular data sets.

The operational section 3458 can access the data sets to build a data structure with an interval tree-like structure and metadata 3458-0. In some embodiments, such an action can include basing the tree-like structure on the ordered indexing to enable rapid access to, and evaluation of, data values corresponding to the indexed locations. Metadata can provide information for the particular data set and/or relate the particular data set to other data sets. The operational section 3458 can also find any missing intervals for the data structures and impute data for the missing intervals 3458-1 to form fully populated data structures (with respect to the ordering).

With the formation of interval tree-like data structures, the operation section 3458 can execute operations between multiple data structures 3458-2. In some embodiments, such operations can include, but are not limited to: selecting between data structures, searching particular intervals over multiple data structures, combining portions of data structures, or merging portions of data structures. From a data structure having imputed values (3458-1) or operation results (3458-2), the data structure can be transformed into a tabular data format 3458-3. Such a tabular data format 3458-3 can be a representation of events across data sets 3462 in indexed order.

While systems as described herein can be utilized to organize any suitable data sets, in some embodiments, a system and method can organize time series data to enable the generation of a tabular data set representing concerted events over a selected time interval.

Figure 35:
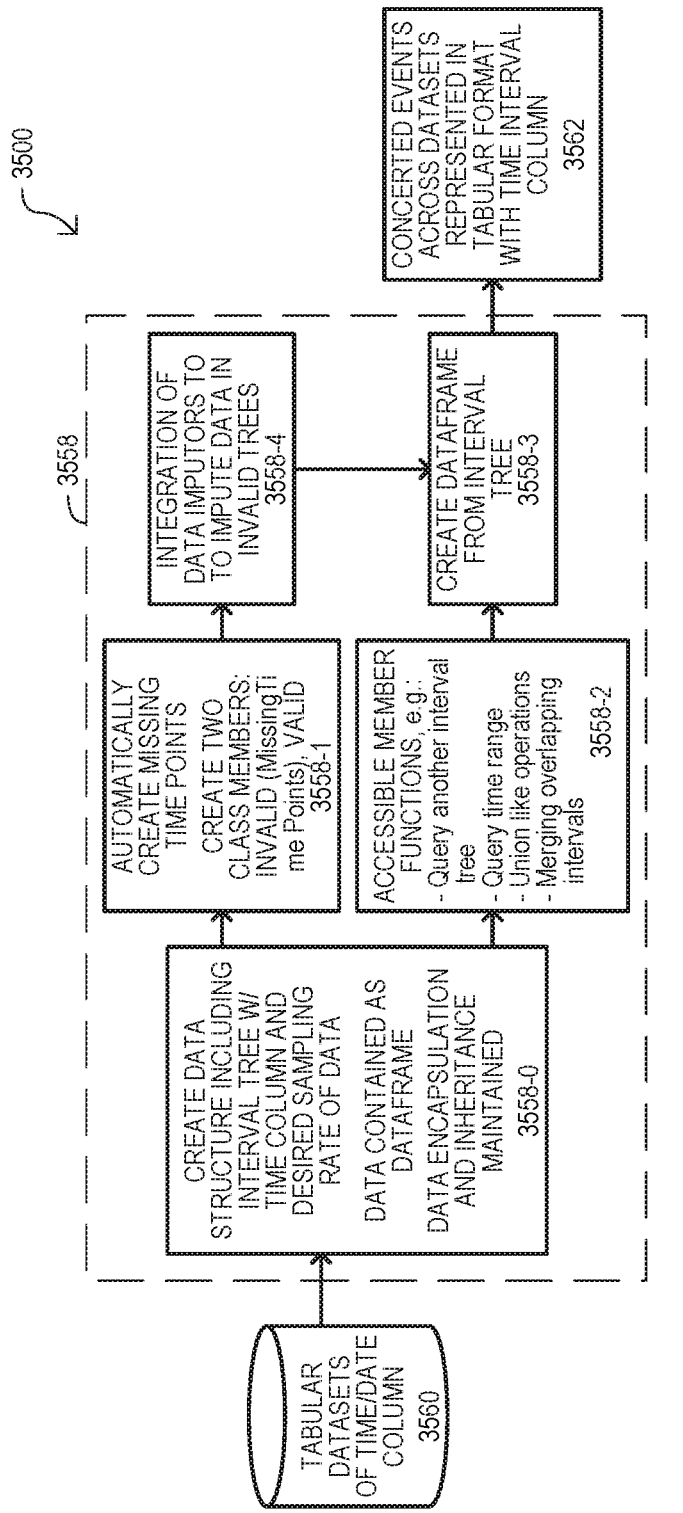

FIG. 35 is a block diagram of a system and method 3500 for representing data sets in tabular form according to another embodiment. The system 3500 can access a storage system that stores tabular data sets with a time and/or date column 3560. In some embodiments, one or more such data sets can be a biophysical sensor reading of a subject.

The operational section 3558 can organize data values of data sets 3560 to enable rapid searching and access to the data values of the data sets. The operational section 3558 can create a data structure including an interval tree using the time column and a desired sample rate 3558-0. In some embodiments, such a data structure can be contained as a dataframe. Data encapsulation and inheritance from the original data set can be maintained (e.g., with metadata of the data set).

Once data structures are created, in the event any data structures do not include time/date points of a desired range, an operational section 3558 can automatically create such time points. In some embodiments, missing time points can be based on a sampling rate, however any other suitable criteria can be used (e.g., force all data sets to have the same or equivalent time/date points). Two class members can be created: INVALID, for those data structures missing time/date points, and VALID, for those data structures having all desired time/date points. For INVALID data structures, data values can be imputed for the missing time/date points 3558-4.

An operational section 3558 can enable any of various accessible member functions 3558-2, including but not limited to: query another interval; query a time range; union like operations; and merging overlapping intervals.

From created data structures, an operational section 3558 can create a dataframe 3558-3. From dataframes, concerted events across datasets can be represented in a tabular format with a time interval column 3562.

FIGS. 36A to 36E show data operations according to an embodiment. It is understood that the data operations are provided by way of example and should not be construed as limiting.

Figure 36A:
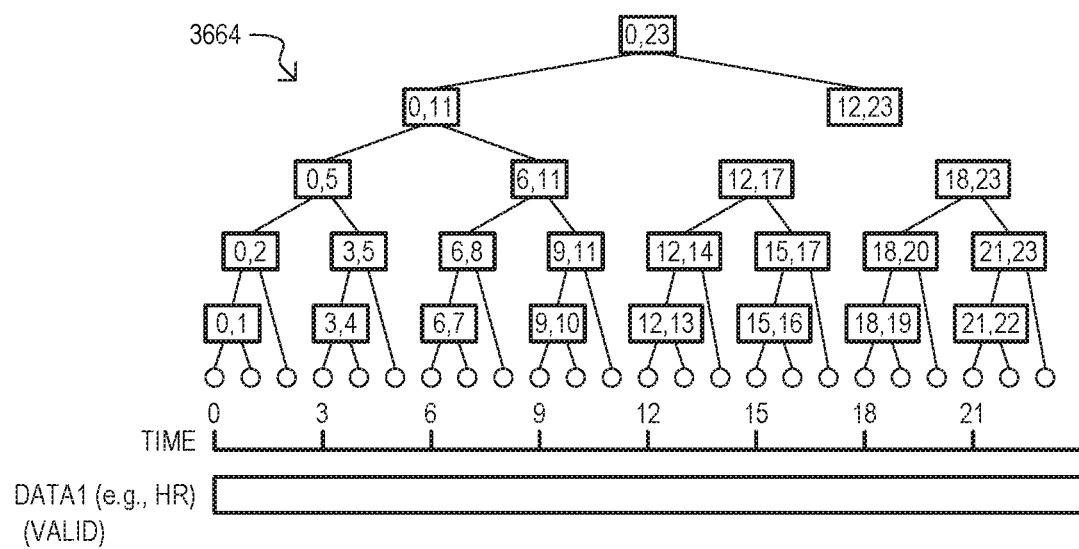
FIGS. 36A to 36E are diagrams showing data sets and outputs for a system like that shown in FIG. 34 or 35.
Figure 36B:
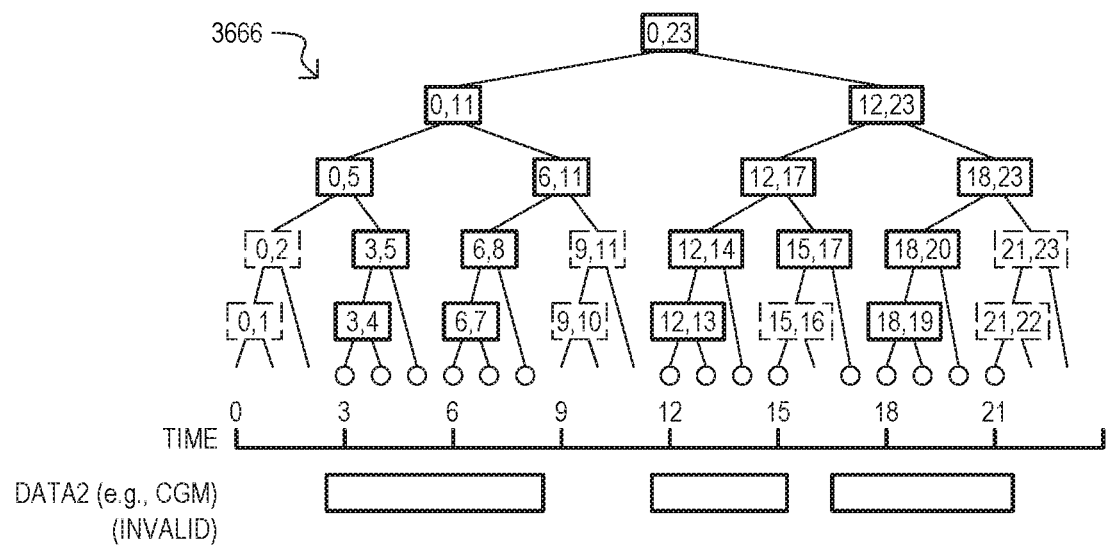

FIG. 36A shows a VALID data structure 3664. The data structure 3664 can include an interval tree corresponding to 24 sampling time periods. Data structure 3664 can be created from a tabular data set having a data value DATA 1 corresponding to each time period. FIG. 36B shows an INVALID data structure 3666. The data structure 3666 can be missing data for sampling time periods. Data structure 3666 can be created from a tabular data set having a data value DATA2 for some, but not all time periods. As a result, there are missing time periods (shown by dashed lines).

Figure 36C:
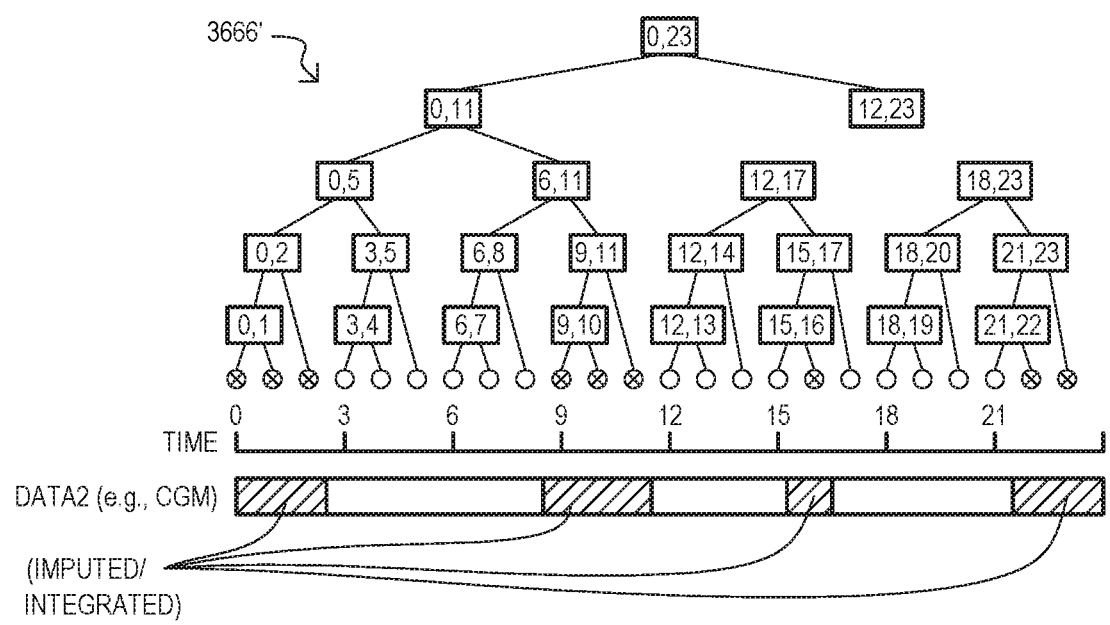
Figures 36D, 36E:
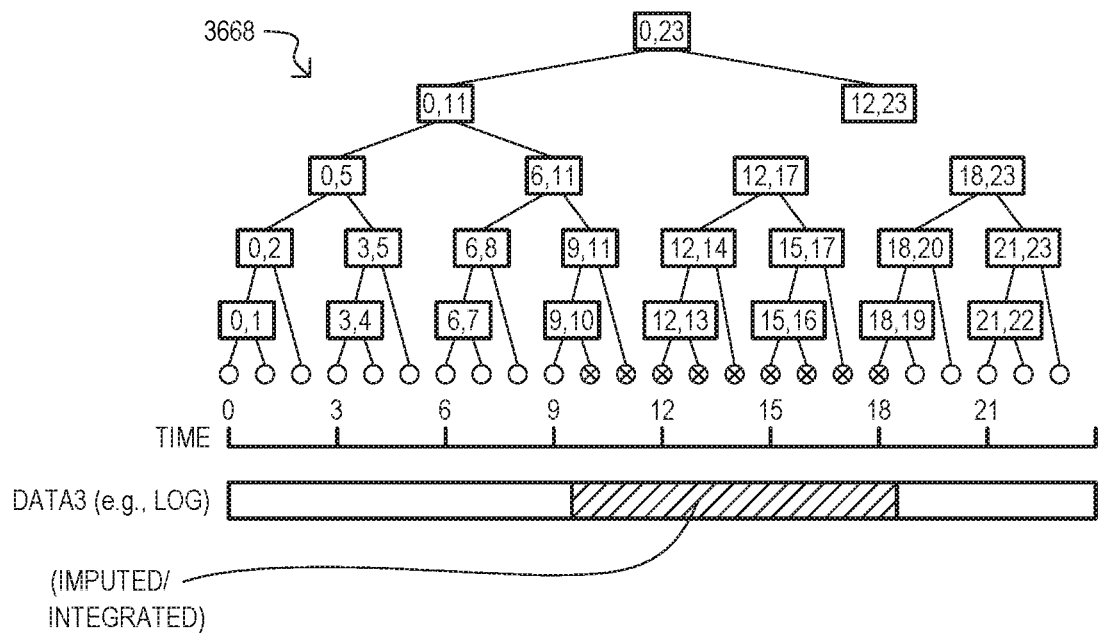

FIG. 36C shows an integrated data structure 3666' created from data structure 3666 shown in FIG. 36B. Missing DATA2 intervals have been created. In addition, data values for missing intervals have been imputed. FIG. 36D shows another integrated data structure 3668 created for another data set composed of data values DATA 3.

FIG. 36E shows a representation across data sets represented in tabular format for times 12-15, generated from data structures of FIGS. 36A, 36C and 36D.

Computer Systems

Figure 37:
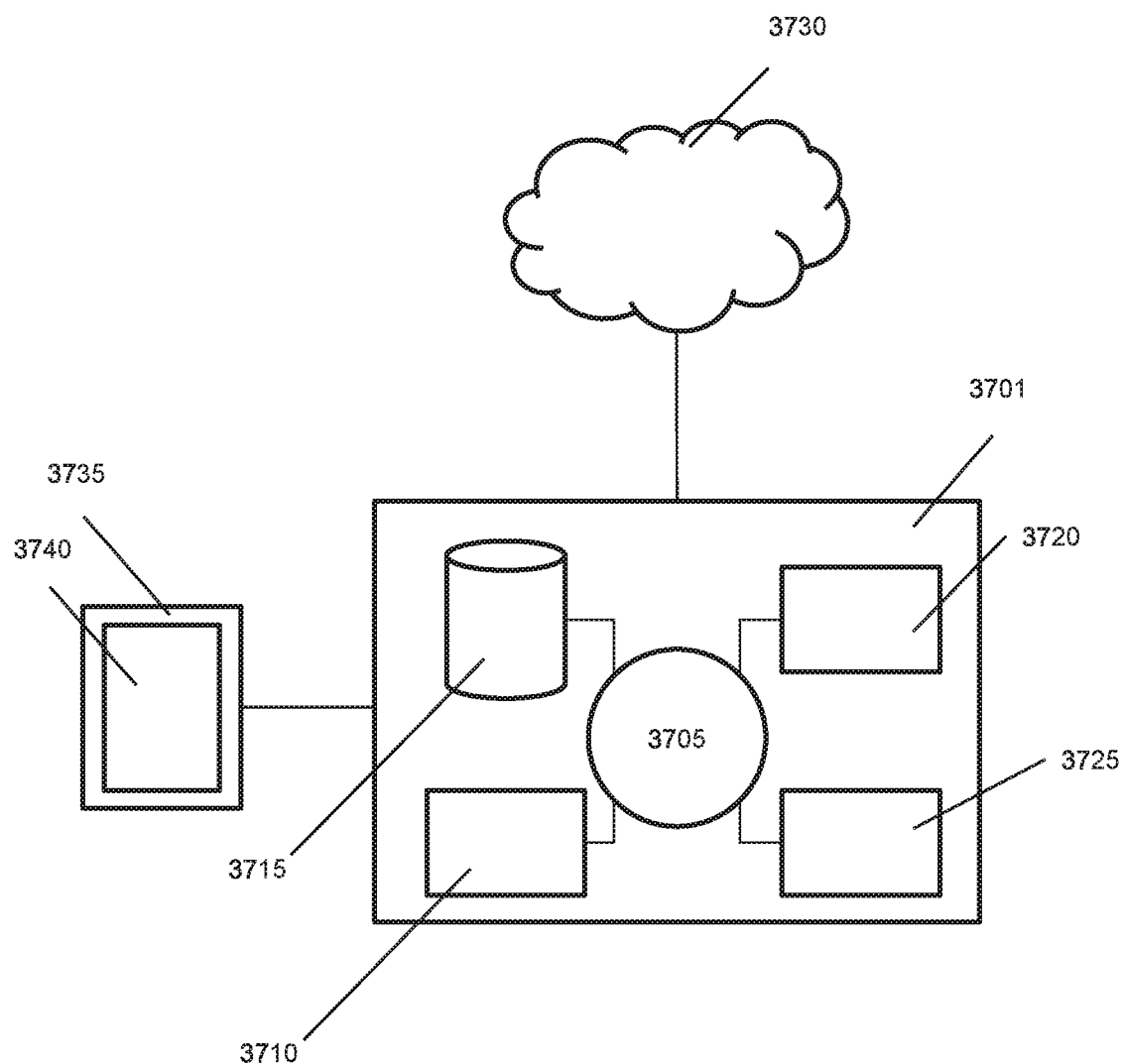
FIG. 37 shows a computer system that is programmed or otherwise configured to implement methods provided herein.

The present disclosure provides computer systems that are programmed to implement methods of the disclosure. FIG. 37 shows a computer system 3701 that is programmed or otherwise configured to implement the machine learning models and methods described herein. The computer system 3701 can be an electronic device of a user or a computer system that is remotely located with respect to the electronic device. The electronic device can be a mobile electronic device.

The computer system 3701 includes a central processing unit (CPU, also "processor" and "computer processor" herein) 3705, which can be a single core or multi core processor, or a plurality of processors for parallel processing. The computer system 3701 also includes memory or memory location 3710 (e.g., random-access memory, read-only memory, flash memory), electronic storage unit 3715 (e.g., hard disk), communication interface 3720 (e.g., network adapter) for communicating with one or more other systems, and peripheral devices 3725, such as cache, other memory, data storage and/or electronic display adapters. The memory 3710, storage unit 3715, interface 3720 and peripheral devices 3725 are in communication with the CPU 3705 through a communication bus (solid lines), such as a motherboard. The storage unit 3715 can be a data storage unit (or data repository) for storing data. The computer system 3701 can be operatively coupled to a computer network ("network") 3730 with the aid of the communication interface 3720. The network 3730 can be the Internet, an internet and/or extranet, or an intranet and/or extranet that is in communication with the Internet. The network 3730 in some cases is a telecommunication and/or data network. The network 3730 can include one or more computer servers, which can enable distributed computing, such as cloud computing. The network 3730, in some cases with the aid of the computer system 3701, can implement a peer-to-peer network, which may enable devices coupled to the computer system 3701 to behave as a client or a server.

The CPU 3705 can execute a sequence of machine-readable instructions, which can be embodied in a program or software. The instructions may be stored in a memory location, such as the memory 3710. The instructions can be directed to the CPU 3705, which can subsequently program or otherwise configure the CPU 3705 to implement methods of the present disclosure. Examples of operations performed by the CPU 3705 can include fetch, decode, execute, and writeback.

The CPU 3705 can be part of a circuit, such as an integrated circuit. One or more other components of the system 3701 can be included in the circuit. In some cases, the circuit is an application specific integrated circuit (ASIC).

The storage unit 3715 can store files, such as drivers, libraries and saved programs. The storage unit 3715 can store user data, e.g., user preferences and user programs. The computer system 3701 in some cases can include one or more additional data storage units that are external to the computer system 3701, such as located on a remote server that is in communication with the computer system 3701 through an intranet or the Internet.

The computer system 3701 can communicate with one or more remote computer systems through the network 3730.

For instance, the computer system 3701 can communicate with a remote computer system of a user (e.g., a mobile device configured to run one of the recommendation applications described herein). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 3701 via the network 3730.

Methods as described herein can be implemented by way of machine (e.g., computer processor) executable code stored on an electronic storage location of the computer system 3701, such as, for example, on the memory 3710 or electronic storage unit 3715. The machine executable or machine-readable code can be provided in the form of software. During use, the code can be executed by the processor 3705. In some cases, the code can be retrieved from the storage unit 3715 and stored on the memory 3710 for ready access by the processor 3705. In some situations, the electronic storage unit 3715 can be precluded, and machine-executable instructions are stored on memory 3710.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 3701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3701 can include or be in communication with an electronic display 3735 that comprises a user interface (UI) 3740 for providing, for example, recommendations to a subject (e.g., diet or physical activity recommendations) that can aid the subject in altering or maintaining a blood glucose level. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3705. The algorithm can, for example, any of the machine learning algorithms or models described herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for training a reinforcement learning algorithm, the method comprising:
   (a) providing a reaction model comprising a personalized learned body model configured to generate a simulated biophysical or behavioral response of a subject responsive to a plurality of inputs;
   (b) until a convergence condition is achieved, iteratively:

(i) generating, using the reinforcement learning algorithm, a recommendation comprising a recommended meal or physical activity, (ii) processing the recommendation using the reaction model to generate a predicted response of the subject to following the recommendation, wherein the predicted response comprises a biophysical or behavioral response, (iii) applying a first reward function to the predicted response to generate a first reward value indicative of a benefit or detriment of the predicted response toward a health measurement of interest; and (iv) training the reinforcement learning algorithm in a first stage using the first reward value;

(c) providing the recommendation to the subject;

(d) measuring the health measurement of interest of the subject responsive to following the recommendation;

(e) applying a second reward function to the measured health measurement of interest to generate a second reward value; and (f) training the reinforcement learning algorithm in a second stage using the second reward value.

2. The method of claim 1, further comprising encoding the measured health measurement of interest of the subject into a low-dimension latent space for providing to the second reward function.

3. The method of claim 1, wherein the first reward function is the same as the second reward function.

4. The method of claim 1, wherein generating the predicted response of the subject further comprises:
processing encoded historical data of the subject using a trained predictor configured to infer the predicted response;
processing the recommendation using an adherence model configured to evaluate an adherence of the subject to the recommendation; and
selectively processing outputs of the trained predictor and the adherence model using the personalized learned body model.

5. The method of claim 4, wherein generating the predicted response further comprises processing the simulated biophysical response using an autoencoder and a generative adversarial network.

6. The method of claim 1, wherein the convergence condition comprises a criterion based at least in part on the magnitude of the first reward.

7. The method of claim 1, wherein the reinforcement learning algorithm comprises a neural network.

8. The method of claim 1, wherein the first reward function generates the first reward at a higher rate than the second reward function generates the second reward.

9. The method of claim 1, wherein the reaction model is trained on historical biophysical or behavioral response data from the subject.

10. The method of claim 9, wherein the reaction model is updated during inference based on new biophysical or behavioral response data of the subject.

11. The method of claim 1, wherein the reaction model comprises a supervised machine learning model.

12. The method of claim 1, wherein the first reward function and the second reward function generate a positive reward when the recommendation results in a beneficial predicted response or measured health measurement of interest of the subject.

13. The method of claim 1, wherein the first reward function and the second reward function generate a negative reward when the recommendation results in a detrimental predicted response or measured health measurement of interest of the subject.

14. The method of claim 1, wherein the predicted response comprises the biophysical response.

15. The method of claim 14, wherein the predicted response comprises a predicted glucose response, and wherein the health measurement of interest comprises a glucose level.

16. The method of claim 15, further comprising measuring the glucose level of the subject using a continuous glucose monitor.

17. The method of claim 1, wherein the predicted response comprises the behavioral response.

18. The method of claim 1, wherein training the reinforcement learning algorithm in the first stage or the second stage comprises adjusting a set of weights or parameters of the reinforcement learning algorithm.

19. The method of claim 1, further comprising using the personalized learned body model to generate the simulated biophysical or behavioral response of the subject in real-time.

20. The method of claim 19, wherein the simulated biophysical or behavioral response of the subject is generated based at least in part on real-time sensor data of the subject.

21. The method of claim 19, further comprising:
determining if the simulated biophysical or behavioral response of the subject is outside of a pre-determined range; and
if the simulated biophysical or behavioral response of the subject is outside of the pre-determined range, providing the recommendation to the subject in real-time, wherein the recommendation is selected to adjust an actual biophysical or behavioral response of the subject to be within the pre-determined range.

22. A system comprising one or more computer processors and one or more storage devices having instructions stored thereon that are operable, when executed by the one or more computers, to cause the one or more computer processors to perform operations comprising:
(a) providing a reaction model comprising a personalized learned body model configured to predict a biophysical or behavioral response of a subject responsive to a plurality of inputs;
(b) until a convergence condition is achieved, iteratively:
(i) generating, using the reinforcement learning algorithm, a recommendation comprising a recommended meal or physical activity,
(ii) processing the recommendation using the reaction model to generate a predicted response of the subject to following the recommendation, wherein the predicted response comprises a biophysical or behavioral response,
(iii) applying a first reward function to the predicted response to generate a first reward value indicative of a benefit or detriment of the predicted response toward a health measurement of interest; and
(iv) training the reinforcement learning algorithm in a first stage using the first reward value;
(c) providing the recommendation to the subject;
(d) measuring the health measurement of interest of the subject responsive to following the recommendation;
(e) applying a second reward function to the measured health measurement of interest to generate a second reward value; and (f) training the reinforcement learning algorithm in a second stage using the second reward value.

23. A non-transitory computer storage medium having instructions stored thereon that are operable, when executed by one or more computer processors, to cause the one or more computer processors to perform operations comprising:
   (a) providing a reaction model comprising a personalized learned body model configured to predict a biophysical or behavioral response of a subject responsive to a plurality of inputs;
   (b) until a convergence condition is achieved, iteratively:
      (i) generating, using the reinforcement learning algorithm, a recommendation comprising a recommended meal or physical activity,
      (ii) processing the recommendation using the reaction model to generate a predicted response of the subject to following the recommendation, wherein the predicted response comprises a biophysical or behavioral response,
      (iii) applying a first reward function to the predicted response to generate a first reward value indicative of a benefit or detriment of the predicted response toward a health measurement of interest; and
      (iv) training the reinforcement learning algorithm in a first stage using the first reward value;
   (c) providing the recommendation to the subject;
   (d) measuring the health measurement of interest of the subject responsive to following the recommendation;
   (e) applying a second reward function to the measured health measurement of interest to generate a second reward value; and
   (f) training the reinforcement learning algorithm in a second stage using the second reward value.

* * * * *